(12) United States Patent
Maltese et al.

(10) Patent No.: US 9,028,796 B2
(45) Date of Patent: May 12, 2015

(54) MATERIALS AND METHODS USEFUL TO INDUCE CELL DEATH VIA METHUOSIS

(75) Inventors: William A. Maltese, Toledo, OH (US); Paul W. Erhardt, Toledo, OH (US); Michael W. Robinson, Toledo, OH (US); Jean H. Overmeyer, Perrysburg, OH (US)

(73) Assignee: The University of Toledo, Toledo, OH (US)

( * ) Notice: Subject to any disclaimer, the term of this patent is extended or adjusted under 35 U.S.C. 154(b) by 23 days.

(21) Appl. No.: 14/001,313

(22) PCT Filed: Feb. 24, 2012

(86) PCT No.: PCT/US2012/026609
§ 371 (c)(1),
(2), (4) Date: Sep. 18, 2013

(87) PCT Pub. No.: WO2012/145069
PCT Pub. Date: Oct. 26, 2012

(65) Prior Publication Data
US 2014/0322128 A1    Oct. 30, 2014

Related U.S. Application Data

(60) Provisional application No. 61/446,354, filed on Feb. 24, 2011.

(51) Int. Cl.
| | | |
|---|---|---|
| C07D 401/06 | (2006.01) |
| A61K 45/06 | (2006.01) |
| A61K 31/4439 | (2006.01) |
| A61K 31/404 | (2006.01) |
| C07D 403/06 | (2006.01) |
| C07D 209/08 | (2006.01) |
| C07D 209/12 | (2006.01) |
| C40B 40/04 | (2006.01) |

(52) U.S. Cl.
CPC ............... *A61K 31/404* (2013.01); *A61K 45/06* (2013.01); *A61K 31/4439* (2013.01); *C07D 401/06* (2013.01); *C07D 403/06* (2013.01); *C07D 209/08* (2013.01); *C07D 209/12* (2013.01); *C40B 40/04* (2013.01)

(58) Field of Classification Search
None
See application file for complete search history.

(56) References Cited

U.S. PATENT DOCUMENTS

| | | |
|---|---|---|
| 7,205,299 B2 | 4/2007 | Gerlach et al. |
| 2006/0019951 A1 | 1/2006 | Kirchhausen et al. |
| 2008/0300291 A1 | 12/2008 | Chen et al. |
| 2009/0042949 A1 | 2/2009 | Pelcman et al. |
| 2010/0298352 A1 | 11/2010 | Prochownik et al. |

OTHER PUBLICATIONS

Bhanot et al., "Induction of Nonapoptotic Cell Death by Activated Ras Requires Inverse Regulation of Rac1 and Arf6", Molecular Cancer Research, 2010, vol. 8, No. 10, pp. 1358-1374.
Cerny et al., "The small chemical vacuolin-1 inhibits Ca2+-dependent lysosomal exocytosis but not cell resealing", EMBO reports, 2004, vol. 5, No. 9, pp. 883-888.
Kroemer et al., "Cell Death Pathways; Apoptosis, Autophagy and Necrosis", 2010 Keystone Symposia Meeting Abstract Book, p. 114.
Overmeyer et al., "Active Ras Triggers Death in Glioblastoma Cells through Hyperstimulation of Macropinocytosis", Molecular Cancer Research, 2008, vol. 6, No. 6, pp. 965-977.
PCT International Search Report and Written Opinion, Application No. PCT/US12/26609, dated Jun. 7, 2012.

*Primary Examiner* — Timothy R Rozof
(74) *Attorney, Agent, or Firm* — MacMillan, Sobanski & Todd, LLC

(57) ABSTRACT

The present invention provides materials and methods to induce cell death by methuosis, a non-apoptotic cell death mechanism. Small molecules herein are useful for treating cell proliferation disorders or anomalies, particularly, but not exclusively, cancer. Methods related to the research and pharmaceutical use of the small molecules are also provided herein.

23 Claims, 28 Drawing Sheets
(4 of 28 Drawing Sheet(s) Filed in Color)

| | Percent Vacuolated Cells |
|---|---|
| H-Ras(G12V) | 74 |
| H-Ras(G12V) + EHT1864 | 20 |
| MIPP | 100 |
| MIPP + EHT1864 | 100 |

Structure-activity relationships for a directed library of MIPP-related compounds

| Cpd. No. | R₁ | R₂ | R₃ | Ar | Viability* (MTT) | Colony Formation** | Vacuoles |
|---|---|---|---|---|---|---|---|
| 2 | H | Me | H | 4-pyridine | 24 ± 3 | 8 ± 4 | Yes |
| 9 | H | H | H | phenyl | 109 ± 7 | 76 ± 7 | No |
| 10 | H | H | H | 2-pyridine | 96 ± 9 | 53 ± 10 | No |
| 11 | H | H | H | 3-pyridine | 72 ± 6 | 71 ± 10 | No |
| 12 | H | H | H | 4-pyridine | 58 ± 7 | 22 ± 2 | Yes |
| 13 | MeO | H | H | 4-pyridine | 58 ± 2 | 2 ± 1 | Yes |
| 14 | BnO | H | H | 4-pyridine | 56 ± 4 | 8 ± 2 | Yes |
| 15 | OH | H | H | 4-pyridine | 107 ± 22 | 72 ± 6 | No |
| 16 | MeO | H | H | 3-pyridine | 90 ± 8 | 99 ± 30 | No |
| 17 | MeO | H | H | pyrazine | 88 ± 8 | 96 ± 22 | No |
| 19 | MeO | Me | H | 4-pyridine | 12 ± 2 | 0 | Yes |
| 20 | MeO | H | Me | 4-pyridine | 73 ± 13 | 52 ± 9 | Yes |
| 21 | OH | Me | H | 4-pyridine | 101 ± 13 | 43 ± 17 | Yes |
| 26 | p-MeBnO | Me | H | 4-pyridine | 79 ± 2 | 76 ± 8 | No |
| 27 | p-CBnO | Me | H | 4-pyridine | 79 ± 9 | 71 ± 11 | No |

* Percent of DMSO control (mean ±SD, n=3); ** Percent of DMSO control (mean±SD, n=3)

Me, methyl; MeO, methoxy; BnO, benyloxyl; p-MeBnO, p-methyl ester benyloxyl; pCBnO, p-COOH benzyloxy

Figure 36

| Colonies per Plate | | |
|---|---|---|
| Cell Line | Control | MOMIPP |
| U87MG | 33 ± 2 | 1 ± 1 |
| LN229 | 179 ± 18 | 0 |
| SF295 | 105 ± 6 | 0 |
| T98G | 34 ± 4 | 0 |
| GBM6 | 37 ± 3 | 2 ± 1 |

MATERIALS AND METHODS USEFUL TO INDUCE CELL DEATH VIA METHUOSIS

CROSS-REFERENCE TO RELATED APPLICATIONS

This is a national stage application filed under 37 C.F.R. §1.371 of international application PCT/US2012/026609, filed under the authority of the Patent Cooperation Treat on Feb. 24, 2012, which claims priority to U.S. Provisional Application Ser. No. 61/446,354 filed under 35 U.S.C. §111 (b) on Feb. 24, 2011. The disclosures of all priority applications are incorporated herein by reference.

STATEMENT REGARDING FEDERALLY SPONSORED RESEARCH

This invention was made with government support under Grant Number R01 CA115495 awarded by the National Institutes of Health. The government has certain rights in the invention.

FIELD OF THE INVENTION

This invention pertains to the field of biology, chemistry and medicine. The invention specifically pertains to materials and methods to induce methuosis, a form of non-apoptotic cell death.

BACKGROUND OF THE INVENTION

Several different forms of non-apoptotic death have, based on specific morphological or molecular criteria. These include death associated with accumulation of autophagosomes, as well as several types of caspase-independent cell death that can represent specialized forms of necrosis; e.g., oncosis, necroptosis and paraptosis. A unique type of non-apoptotic cell death can be induced in glioblastoma and gastric carcinoma cells by constitutive stimulation of Ras signaling pathways. This unique form of cell death is distinct from other kinds of non-apoptotic death noted above. It involves stimulation of macropinocytosis (cell drinking), combined with defects in clathrin-independent endocytic vesicle trafficking, ultimately resulting in accumulation of large vacuoles that disrupt cellular membrane integrity. The unique form of cell death is termed 'methuosis', from the Greek methuo, to drink to intoxication. Mechanistically, the effects of Ras overexpression are related to activation of Rac1 and inactivation of Arf6, two GTPases implicated in macropinocytosis and endosome recycling, respectively.

Cancer cells typically harbor mutations in tumor suppressor genes that control programmed cell death, rendering them relatively insensitive to apoptosis. Moreover, many tumors that initially respond to treatment with chemotherapeutic drugs eventually develop multi-drug resistance due to increases in drug efflux mechanisms or DNA repair capacity. These challenges have stimulated interest in identifying alternative cell death pathways that can be used to kill tumor cells that have ceased to respond to drugs that depend on induction of apoptotic mechanisms.

SUMMARY OF THE INVENTION

Without wishing to be bound by a particular theory, embodiments of compounds, compositions and methods of the invention can act via methuosis to be effective in the treatment of cancer cells.

Disclosed herein is a chalcone-related compound that can rapidly induce cell death with the hallmarks of methuosis in both temozolomide-resistant and non-resistant glioblastoma cells, raising the possibility that it can serve as a prototype for a new class of therapeutic agents that can be used to treat tumors that are resistant to conventional drugs.

In one embodiment there are provided compounds having the structure of Formula I:

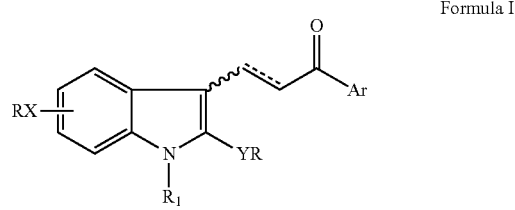

Formula I wherein X and Y are independently absent or halogen; oxygen; azide; nitrogen; (CO)O; O(CO); O(CO)O; (CO)N; NH(CO); NH(CO)N; NH(CO)O; or O(CO)N, wherein if X or Y is halogen or azide, then R is absent, and wherein X or Y is nitrogen, (CO)N, or O(CO)N, or NH(CO)N, then two R groups are present;

wherein R and $R_1$ are independently hydrogen; alkyl, alkenyl, alkynyl, aryl or aralkyl;

wherein Ar is aryl;

wherein the dashed line is an optional double bond;

wherein the wavy line indicates that when said double bond is present, the resulting stereochemistry can be either cis or trans;

wherein when XR is hydrogen and Y is absent, then R is not hydrogen or methyl; and wherein when XR is halide and Y is absent, then R is not hydrogen; or pharmaceutically acceptable salts, hydrates, and optical isomers thereof.

Also provided herein are compounds of Formula I, wherein the wavy line indicates that a trans double bond is present; wherein XR is methoxy bound at the 5 position, YR is methyl, and R1 is hydrogen; wherein Ar is 3,4,5-trimethoxyyphenyl; and wherein Ar is 4-pyridyl.

In yet another embodiment, there are provided herein compounds having the structure of Formula II:

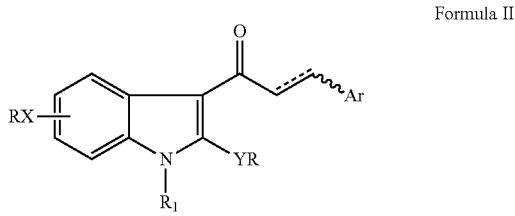

Formula II wherein X and Y are independently absent or halogen; oxygen; azide; nitrogen; (CO)O; O(CO); O(CO)O; (CO)N; NH(CO); NH(CO)N; NH(CO)O; or O(CO)N, wherein if X or Y is halogen or azide, then R is absent, and wherein X or Y is nitrogen, (CO)N, or O(CO)N, or NH(CO)N, then two R groups are present;

wherein R and $R_1$ are independently hydrogen; alkyl, alkenyl, alkynyl, aryl or aralkyl;

wherein Ar is aryl;

wherein the dashed line is an optional double bond;
wherein the wavy line indicates that when said double bond is present, the resulting stereochemistry can be either cis or trans; or pharmaceutically acceptable salts, hydrates, and optical isomers thereof.

Also provided herein are compounds of Formula II wherein the wavy line indicates that a trans double bond is present; wherein XR is methoxy bound at the 5 position, YR is methyl, and R1 is hydrogen; wherein Ar is 3,4,5-trimethoxyphenyl; and wherein Ar is 4-pyridyl.

In yet another embodiment, there are provided methods of inducing cell death in at least one cell, comprising introducing a compound of claim 1 or claim 6 or both, to at least one cell and inducing cell death. Wherein the at least one cell is a mammalian cell; wherein the at least one cell is apoptosis-resistant; wherein the at least one cell is a cancer cell; wherein the at least one cell is in vitro; wherein the at least one cell is an animal research model for cancer; wherein the animal research model is for apoptosis-resistant cancer; and wherein the at least one cell is at least one human cell.

In another embodiment, there are provided methods of inducing cell death in a mammal in need of such induction administering to a subject a pharmacologically effective amount of a compound of Formula I or Formula II, or both. Wherein the mammal is selected from the group consisting of: mouse; rat; guinea pig; rabbit; cat; dog; monkey; goat; cow; horse; and human; and wherein the mammal is a human.

In yet another embodiment, there are provided methods of ameliorating the effects of cancer in a mammal in need of such amelioration, comprising administering to a subject a pharmacologically effective amount of a compound of Formula I or Formula II, or both. Also provided are methods wherein the cancer is selected from the group consisting of: brain, bladder, lung, liver, pancreas, bone, colon, stomach, breast, prostate, ovary, central nervous system, or skin cancer; wherein the mammal is selected from the group consisting of: mouse; rat; guinea pig; rabbit; cat; dog; monkey; goat; cow; horse; and human; wherein the mammal is a human.

Also provided are methods wherein the method further comprises administering a second compound, adjuvant or additional therapeutic to the mammal. Also provided are methods which further comprise physical removal of glioblastoma cells via a method selected from the group consisting of: surgery; aspiration; dissection; ablation; and electromagnetic fluctuations.

In yet another embodiment, there are provided compositions of matter comprising a compound of Formula I or Formula II, or both, and a cancer therapeutic. Also provided are compositions wherein the cancer therapeutic is selected from the group consisting of chemotherapeutic drug; toxin; immunological response modifier; enzyme; gamma radiation, and radioisotope.

In yet another embodiment, there are provided methods of ameliorating the effects of cellular proliferation disorder in a mammal in need of such amelioration, comprising administering to a subject a pharmacologically effective amount of a compound of Formula I or Formula II, or both.

In yet another embodiment, there are provided compounds selected from the group consisting of: trans-3-(5-Methoxy-2-methyl-1H-indol-3-yl)-1-(4-pyridinyl)-2-propen-1-one (MOMIPP); 2-Methylindole-3-carboxaldehyde (compound 2a); trans-3-(2-Methyl-1H-indol-3-yl)-1-(4-pyridinyl)-2-propen-1-one (compound 2); trans-3-(1H-Indol-3-yl)-1-phenyl-2-propen-1-one (compound 9); trans-3-(1H-Indol-3-yl)-1-(2-pyridinyl)-2-propen-1-one (compound 10); trans-3-(1H-Indol-3-yl)-1-(3-pyridinyl)-2-propen-1-one (compound 11); trans-3-(1H-Indol-3-yl)-1-(4-pyridinyl)-2-propen-1-one (compound 12); trans-3-(5-Methoxy-1H-indol-3-yl)-1-(4-pyridinyl)-2-propen-1-one (compound 13); trans-3-(5-Phenylmethoxy-1H-indol-3-yl)-1-(4-pyridinyl)-2-propen-1-one (compound 14); trans-3-(5-Hydroxy-1H-Indol-3-yl)-1-(4-pyridinyl)-2-propen-1-one (compound 15); trans-3-(5-Methoxy-1H-indol-3-yl)-1-(3-pyridinyl)-2-propen-1-one (compound 16); trans-3-(5-Methoxy-1H-indol-3-yl)-1-(pyrazine)-2-propen-1-one (compound 17); 5-Methoxy-2-methyl-1H-indole-3-carboxaldehyde (compound 18); trans-3-(5-Methoxy-2-methyl-1H-indol-3-yl)-1-(4-pyridinyl)-2-propen-1-one (compound 19); trans-3-(5-Methoxy-1-methyl-Indol-3-yl)-1-(4-pyridinyl)-2-propen-1-one (compound 20); trans-3-(5-Hydroxy-1H-Indol-3-yl)-1-(4-pyridinyl)-2-propen-1-one (compound 21); 2-Methyl-1H-indol-5-ol (compound 22); 5-(4-Methylbenzoate)methoxy-2-methyl-1H-indole (compound 23); 5-(4-Methylbenzoate)methoxy-2-methyl-1H-indole-3-carboxaldehyde (compound 24); 5-(4-Benzoate)methoxy-2-methyl-1H-indole-3-carboxaldehyde (compound 25); trans-3-[5-((4-Methylbenzoate)methoxy)-1H-Indol-3-yl)]-1-(4-pyridinyl)-2-propen-1-one (compound 26); trans-3-[5-((4-Carboxyphenyl)-methoxy)-1H-Indol-3-yl)]-1-(4-pyridinyl)-2-propen-1-one (compound 27); 2-Methyl-5-benzoyl-indole-3-carboxaldehyde (compound 28); 2-Methyl-6-benzoyl-indole-3-carboxaldehyde (compound 29); 2-Methyl-5-benzoyl-indole-3-carboxaldehyde (compound 28); 2-Methyl-6-benzoyl-indole-3-carboxaldehyde (compound 29); trans-3-(5-Benzoyl-2-methyl-1H-indol-3-yl)-1-(4-pyridinyl)-2-propen-1-one (compound 30); trans-3-(6-Benzoyl-2-methyl-1H-indol-3-yl)-1-(4-pyridinyl)-2-propen-1-one (compound 31); 2-Methyl-5-nitro-1H-indole (compound 32); 2-Methyl-5-amino-1H-indole (compound 33); 2-Methyl-5-azido-1H-indole (compound 34); 2-Methyl-3-carboxaldehyde-5-azido-1H-indole (compound 35); trans-3-(5-Azido-2-methyl-1H-indol-3-yl)-1-(4-pyridinyl)-2-propen-1-one (compound 36); 2-Methyl-5-methoxy-6-nitro-1H-indole (compound 37); 2-Methyl-5-methoxy-6-amino-1H-indole (compound 38); 2-Methyl-5-methoxy-6-azido-1H-indole (compound 39); 2-Methyl-3-carboxaldehyde-5-methoxy-6-azido-1H-indole (compound 40); and trans-3-(6-Azido-5-methoxy-2-methyl-1H-indol-3-yl)-1-(4-pyridinyl)-2-propen-1-one (compound 41), or pharmaceutically acceptable salts, hydrates, and optical isomers thereof.

Also provided are compounds selected from FIG. 48, or pharmaceutically acceptable salts, hydrates, and optical isomers thereof.

In particular, compound #2 (MIPP) of FIG. 48 is provided, or pharmaceutically acceptable salts, hydrates, and optical isomers thereof.

In particular, compound #2 (MIPP) of FIG. 48 is provided, or pharmaceutically acceptable salts, hydrates, and optical isomers thereof.

In particular, compound #12 of FIG. 48 is provided, or pharmaceutically acceptable salts, hydrates, and optical isomers thereof.

In particular, compound #13 of FIG. 48 is provided, or pharmaceutically acceptable salts, hydrates, and optical isomers thereof.

In particular, compound #14 of FIG. 48 is provided, or pharmaceutically acceptable salts, hydrates, and optical isomers thereof.

In particular, compound #19 (MOMIPP) of FIG. 48 is provided, or pharmaceutically acceptable salts, hydrates, and optical isomers thereof.

Various aspects of this invention will become apparent to those skilled in the art from the following detailed description of the preferred embodiment, when read in light of the accompanying drawings.

BRIEF DESCRIPTION OF THE FIGURES

The patent or application file can contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 2. Time-lapse phase-contrast microscopy of U251 cells treated with MIPP. The small two-headed arrows point to vesicles that have fused in the subsequent frame. FIG. 3. The same field of cells is depicted in the matching phase-contrast and fluorescent images. In the top left panel, the arrows indicate some of the specific vacuoles that have incorporated the Lucifer yellow. FIG. 4. Phase-contrast images of vacuoles induced by MIPP, showing that Filipin blocks the induction of vacuoles. FIG. 5. Phase-contrast images of Bafilomycin A1 (Baf-A) blocking the induction of vacuoles by MIPP.

FIG. 12. MTT assay of U251 cells treated over time with the indicated compounds (refer to FIG. 1 for structures) at a concentration of 10 μM. The arrows point to vacuolated cells that have rounded and detached from the surface of the dish. FIG. 13. ATP levels decline in cells treated with MIPP. FIG. 14. The arrows point to the vacuolated cells that have rounded and detached from the surface of the dish in cultures treated with MIPP. FIG. 15. U251 cells were treated with 10 μM MIPP or an equivalent volume of DMSO (control) for 2 days and colony forming assays were performed. FIG. 16. U251 cells were examined by electron microscopy after two days of treatment with 10 μM MIPP. The arrows point to regions of plasma membrane discontinuity indicative of cell rupture. FIG. 17. Inhibition of caspase activity does not prevent MIPP-induced cell death.

FIG. 18. Cells were treated with the indicated concentrations of temozolomide for 48 h. FIG. 19. Phase-contrast images of cells after treatment for 48 h with 10 μM MIPP or an equivalent volume of DMSO (control). FIG. 20. MTT assays were performed after treatment for 48 h with the indicated concentrations of MIPP or an equivalent volume of DMSO. FIG. 21. U251-TR cells were treated with 10 μM MIPP or an equivalent volume of DMSO (control) for 2 days and colony forming assays were performed.

FIG. 23. U251 cells were incubated with MIPP for 24 h in the presence or absence of 25 μM EHT 1864. FIG. 24. In a separate experiment, U251 cells were incubated with or without EHT 1864 following nucleofection with a vector encoding a constitutively active H-Ras (G12V). FIG. 25. Phase-contrast images were taken 24 h after addition of the Rac inhibitor. The scale bars are 10 microns.

FIG. 26. Phase-contrast images of cells were acquired after two days of treatment with 10 μM MIPP. FIG. 27. MTT assays were performed on cells treated for the indicated number of days with 10 μM MIPP or an equivalent volume of DMSO. FIG. 28. Colony-forming assays for the transformed cell lines.

FIG. 36. Structure-activity relationships of a directed library of compounds related to compound 2 (MIPP). The $R_1$, $R_2$, $R_3$ and Ar groups refer to positions designated in the structures depicted in FIGS. 30-35.

DETAILED DESCRIPTION OF THE INVENTION

Figure 1:
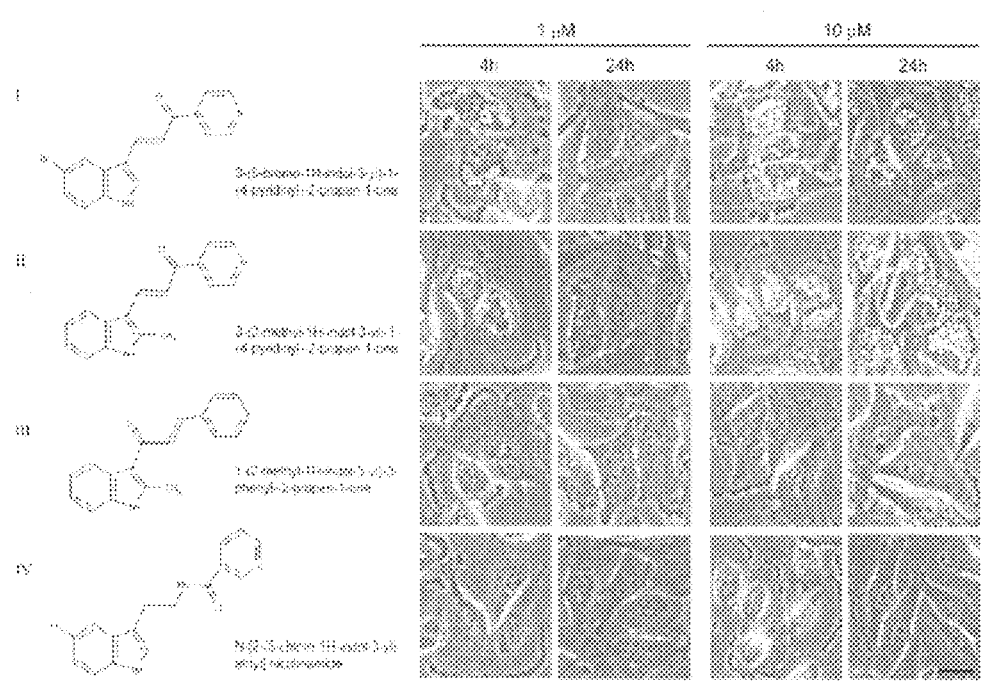
FIG. 1. Compounds, I and II, induce extreme cytoplasmic vacuolization in U251 glioblastoma cells.

Disclosed herein is a specific chalcone-like molecule, 3-(2-methyl-1H-indol-3-yl)-1-(4-pyridinyl)-2-propen-1-one (MIPP) that is shown to induce cell death with the hallmarks of methuosis. MIPP causes rapid accumulation of vacuoles that can be labeled with extracellular fluid phase tracers. Vacuolization can be blocked by an inhibitor of the vacuolar-type Fr-ATPase, bafilomycin A1, and by the cholesterol-interacting compound, filipin, consistent with the endosomal origin of the vacuoles. Although the vacuoles acquire some characteristics of late endosomes, they remain distinct from lysosomal and autophagosomal compartments, showing a block at the late endosome/lysosome boundary.

MIPP targets steps in the endosomal trafficking pathway mediated by Rab5 and Rab7, as shown by changes in the activation states of these GTPases. These effects are specific, as other GTPases (Rac1, Arf6) are unaffected by the compound. Cells treated with MIPP lose viability within 2-3 days, but their nuclei show no apoptotic changes. Inhibition of caspase activity does not protect the cells, consistent with a non-apoptotic death mechanism. A U251 glioblastoma line selected for temozolomide resistance showed sensitivity to MIPP-induced methuosis that was comparable to the parental cell line. MIPP can serve as a prototype for new drugs that can be used to induce non-apoptotic death in cancers that have become refractory to agents that work through DNA damage and apoptotic mechanisms.

Glioblastomas are highly aggressive brain tumors that almost always recur after surgery. Treating these tumors is extremely challenging because the residual cells are highly invasive and they typically harbor genetic mutations that decrease their sensitivity to apoptosis induced by radiation or DNA alkylating agents. Thus, the discovery of cell death mechanisms that do not depend on activation of the classical mitochondrial or death receptor-mediated apoptotic pathways presents new opportunities to treat these devastating tumors. A non-conventional form of cell death termed methuosis can be triggered by ectopic expression of constitutively activated Ras in glioblastoma and other cancer cell lines.

In this disclosure, a small molecule termed MIPP has been identified, which induces the hallmark cytopathological features of methuosis. Shortly after being exposed to MIPP, glioblastoma cells exhibit influx of multiple macropinocytotic vesicles. In the time-lapse studies, the latter can be seen undergoing fusion events to form larger vacuoles. As the vacuoles accumulate, they rapidly acquire some characteristics of late endosomes (Rab7, LAMP1), but they do not merge with lysosomal compartments. Ultimately, the displacement of much of the cytoplasmic space by the vacuoles is accompanied by a decline in metabolic activity and a necrosis-like rupture of the cell. Consistent with a non-apoptotic mechanism, these changes cannot be prevented by caspase inhibitors, and nuclear chromatin condensation typical of apoptosis is not observed. Further, in this disclosure it is shown that glioblastoma cells selected for resistance to the front-line chemotherapeutic drug, temozolomide, were susceptible to MIPP-induced methuosis by comparing doxorubicin-resistant versus non-resistant MCF-7 breast cancer cells treated with a MIPP analog. It is disclosed herein that MIPP can serve as a prototype for development of drugs that can be used to trigger death by methuosis in drug-resistant cancers.

Figure 29:
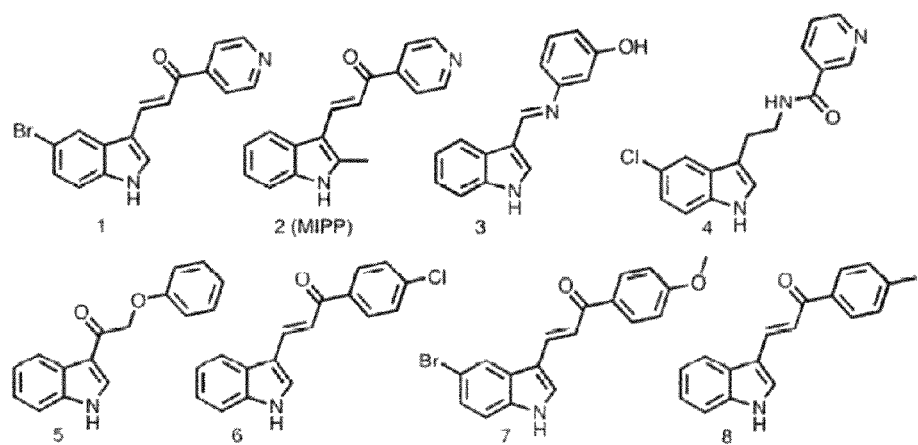
FIG. 29. Compounds related to compound 2 (MIPP) identified from database searches and purchased from commercial suppliers.

Further disclosed herein is the ability of compounds 1 (BIPP) and 2 (MIPP) to induce methuosis. A similarity search of chemical databases was performed using the Chembridge Hit2Lead search engine, which provided compounds 3-8, as shown in FIG. 29, for analysis of whether certain similarly-structured compounds can induce methuosis. When testing these compounds in U251 glioblastoma cells at 10 μM, all compounds were completely inactive in inducing methuosis and limiting cell growth.

In certain embodiments, based on the data of compounds 3-8, the 3-indole-1-pyridinyl-2-propen-1-one scaffold was used to induce methuosis. Compounds 3-8 all possess this core, yet were inactive. The inactivity of compound 8 is most revealing when compared to active compound 1, indicating that addition of a para-methoxy in place of the pyridine nitrogen rendered the compound inactive.

Figure 30:
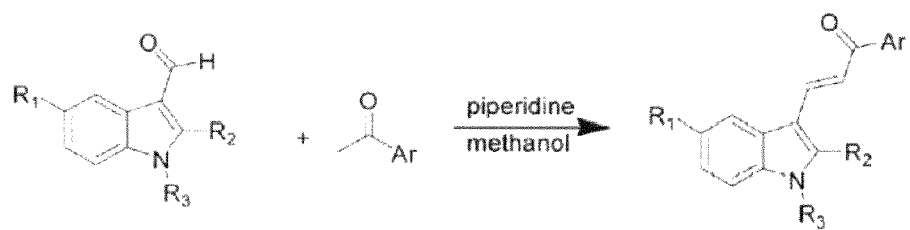
FIG. 30. Reaction scheme for condensation of various acetyl-pyridines or acetophenone with indole-3-carboxaldehyde to obtain compounds 9-12.
Figure 48:
FIG. 48. Table of summary of SAR studies performed on MIPP (compound 2) and related compounds.

Analogs based on the α,β-unsaturated ketone core were designed from Claisen-Schmidt condensations between indole-3-carboxaldehydes and aromatic ketones. Such aldol condensations are known to proceed well employing secondary amines as catalysts. Initially, the orientation of the pyridine nitrogen was investigated. Condensation of various acetyl-pyridines or acetophenone with indole-3-carboxaldehyde (FIG. 30) yielded compounds 9-12 (FIGS. 36 and 48). The activities of these compounds were compared to compound 2 (i.e., MIPP), at a concentration of 10 μM using three criteria: 1) morphological vacuolization of live cells assessed by phase contrast microscopy at 24 h and 48 h, 2) cell viability, assessed at a 48 h end point by MTT assay, with fresh compound added after the first 24 h, and 3) colony forming assays (two week end-point) performed on cells exposed to the compounds for 48 h. The results of this analysis (FIGS. 36 and 48) showed that a para-nitrogen orientation of the pyridine ring is a key feature required for activity. The meta and ortho analogs 10 & 11, as well as the acetophenone analog 9 were all relatively ineffective at inducing methuosis compared with MIPP. In contrast, removal of the 2-methyl from the indole ring of MIPP reduced but did not eliminate activity.

Figure 31:
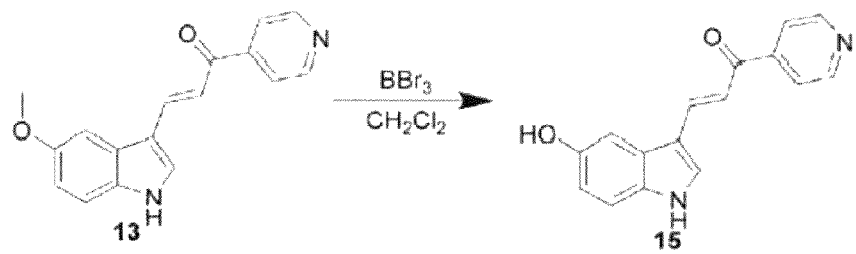
FIG. 31. Reaction scheme for demethylation of compound 13 to produce the 5-OH derivative, compound 15.

Next, the consequences of functionalizing the 5-position of the indole ring with the suitable 5-methoxy and 5-benzyloxy indole-3-carboxaldehydes, compounds 13 and 14 was explored. The 5-methoxy compound 13 was demethylated with BBr$_3$, affording the 5-OH compound 15 (FIG. 31). As shown in FIG. 36 and FIG. 48, the activities of compounds 13 and 14 were similar to compound 2 (MIPP) when compared by colony-forming assay and cell morphology, although they were not as effective in the short-term viability assay. In contrast, addition of the OH to the 5-position greatly reduced activity of the compound in all of the assays. To verify that the location of the pyridine nitrogen was still crucial in the 5-substituted compounds, analogs 16 and 17 were generated. Loss of activity confirmed the necessity of the para-nitrogen (FIGS. 36 and 48).

Figure 32:
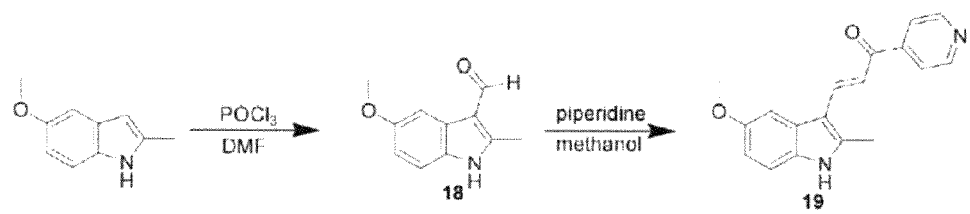
FIG. 32. Reaction scheme for synthesis of compound 19 via Vilsmeier-Haack formylation, followed by coupling with acetyl-pyridine.

After comparing compounds 13 and 14 to MIPP, which showed that modifications at the 5- and 2-positions of the indole ring both affect the activity of these compounds, a 2-methyl-5-methoxy analog was generated from available 2-methyl-5-methoxy-indole. Compound 19 was synthesized by a Vilsmeier-Haack formylation, followed by coupling with 4-acetyl-pyridine (FIG. 32). The activity of this compound exceeded that of compound 2 in both the MTT viability assay and the colony formation assay (FIGS. 36 and 48).

Figure 33:
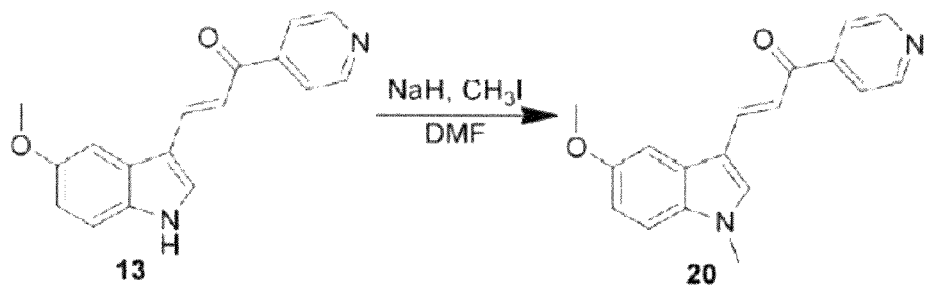
FIG. 33. Reaction scheme for methylation of the indole nitrogen of compound 13 to yield compound 20.
Figure 34:
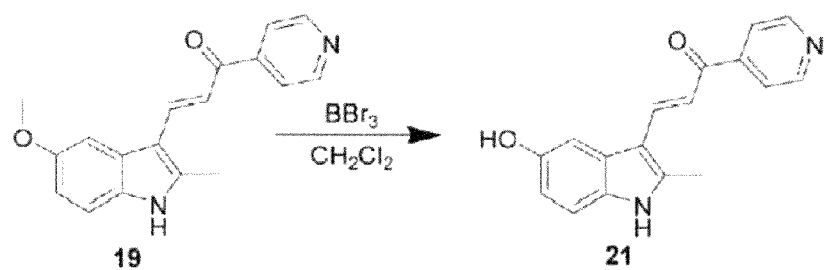
FIG. 34. Reaction scheme for generating compound 21 by demethylation of compound 19.

The addition of the methyl at the indole's 2 position in compound 19 gave added potency versus compound 13, possessing only the 5-methoxy. Methylation of the indole-nitrogen of compound 13 with NaH/CH₃I in DMF (FIG. 33) to yield 20, produced a compound that induced some cytoplasmic vacuolization but had modest effects on cell viability. Thus, after comparing compounds 11, 19 and 20, it is shown that optimal activity is achieved when the 1 and 2 position of the indole are occupied by H and methyl, respectively. The 5-OH compound 21, made by BBr₃ demethylation of compound 19 (FIG. 34), showed a marked reduction in activity compared to the 5-methoxy compound 19, consistent with the detrimental effect of the 5-OH in compound 15.

Further disclosed herein are the effects of modifying the 5-position of the indole with a group that would add polarity at physiological pH. An analog of compound 14 was designed, that added charge and also included a methyl at the indole's 2 position. No appreciable amount of product was produced by direct alkylation of compound 21. Multiple bases were screened with varying pKa's, from $K_2CO_3$ and $Cs_2CO_3$, as well as triethylamine, DBU, TMG and NaH. In all reactions, alkylation at the pyridine nitrogen was observed.

Figure 35:
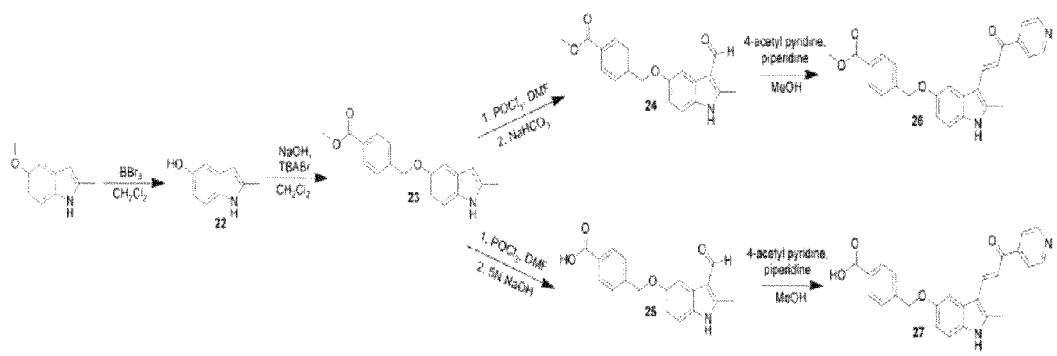
FIG. 35. Reaction scheme for generating polar analogs of compound 19 by functionalizing the indole ring before introduction of the 4-pyridine moiety.
Figure 37:
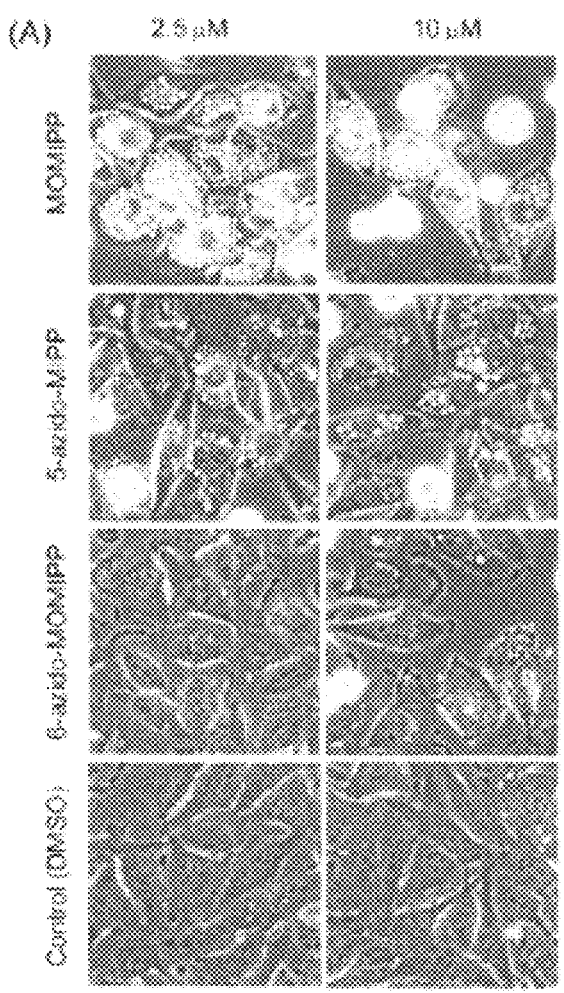
FIG. 37A-37D. Dose-response comparison of the effects of MOMIPP versus MIPP, 5-azido MIPP and 6-azido-MIPP on the morphology and viability of U251 glioblastoma cells.
Figure 37:
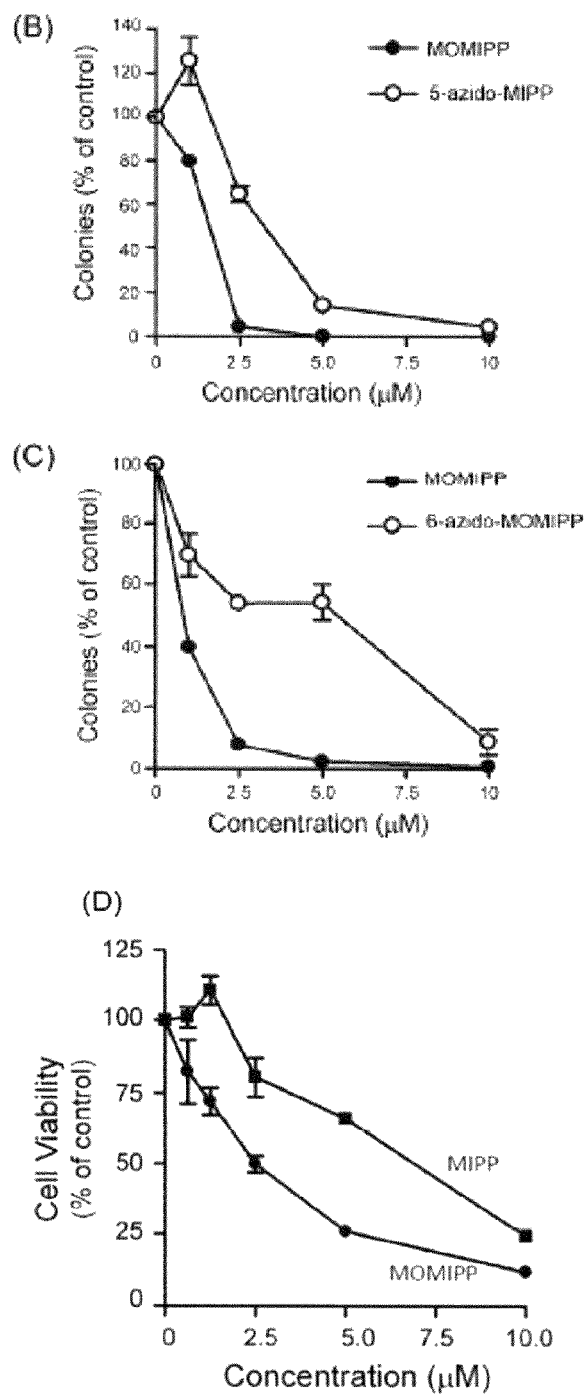

Stronger bases such as TMG and NaH, even using one equivalent, produced appreciable indole-N-alkylation as well as pyridine and indole-OH alkylation. The yield of singly alkylated product at the 5-indole position was negligible. Thus, a new route was designed by functionalizing the indole before introduction of the pyridine moiety (FIG. 35). Available 2-methyl-5-methoxy-indole was demethylated with BBr₃ providing compound 22, followed by alkylation with 4-methyl-(bromomethyl)-benzoate under phase-transfer conditions to afford the singly O-alkylated product compound 23. After formylation with POCl₃/DMF, compounds 24 and 25 were selectively made. Workup in mild base (NaHCO₃) produced the ester compound 24, while workup in 5N NaOH gave acid compound 25. Condensations with 4-acetyl-pyridines provided the corresponding targets compounds 26 and 27. However, neither compound 26 nor compound 27 induced methuosis (FIGS. 36 and 48).

Superior biological activity of MOMIPP versus MIPP was confirmed in studies with U251 glioblastoma cells, using MTT viability assays, cell growth assays, morphological assessment, and colony forming assays to compare the two compounds. FIGS. 37A-37D show the dose-response curves for the effects of the two drugs on cell viability. Each compound was added at the mentioned concentration for two days, with medium and compounds replenished after the first day. The relative $IC_{50}$ for MOMIPP was 1.9 µM, versus 4.8 µM for MIPP.

Figure 38:
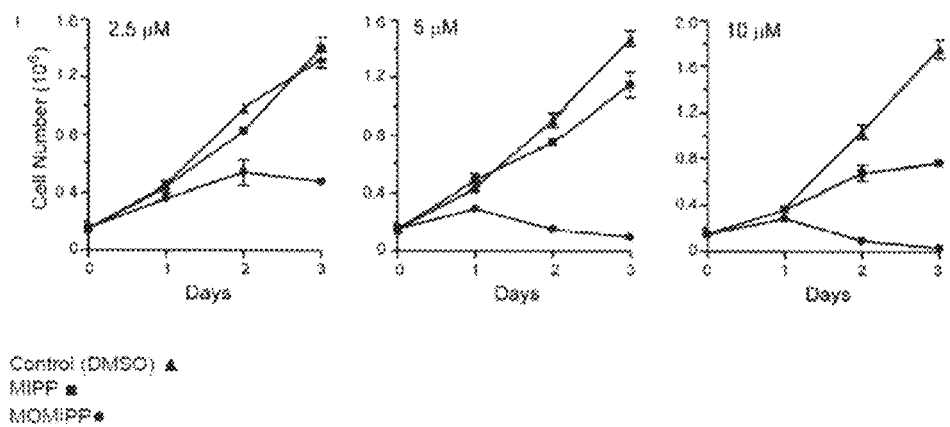
FIG. 38. Effects of MOMIPP versus MIPP on cell proliferation and viability determined by cell number.

To obtain a measure of the comparative duration of activity for each compound, their effects on cell growth and survival were assessed by counting the number of cells in parallel cultures treated for three consecutive days with 2.5 µM, 5 µM, or 10 µM compound (FIG. 38). Unlike the viability studies, in these experiments the compounds were added at the beginning of the study and were not replenished for the duration. Under these conditions, MOMIPP was shown to be more effective than MIPP in reducing cell growth and viability. The reduction of cell number in the cultures treated with MOMIPP coincided with massive early vacuolization of the cells and loss of nonviable cells from the substratum (FIG. 39).

Figure 39:
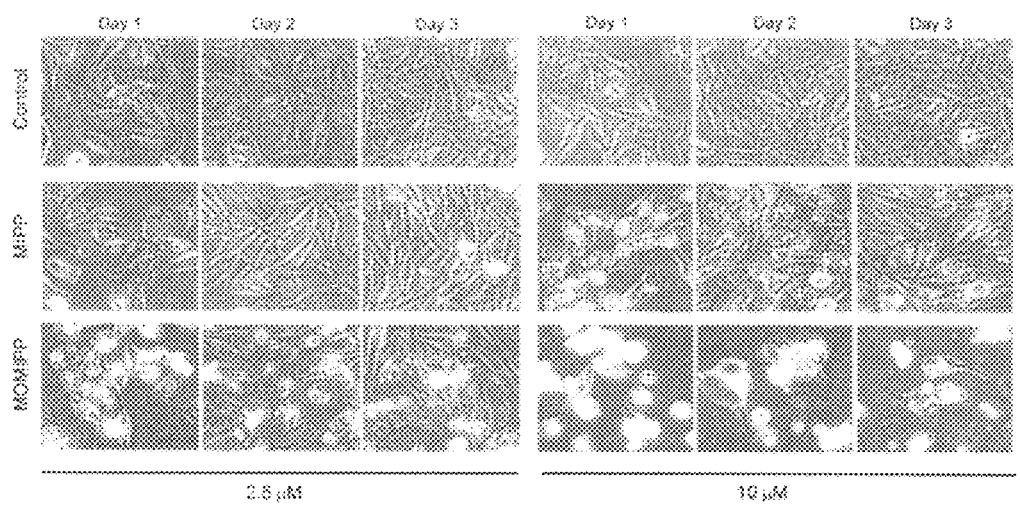
FIG. 39. Comparison of the effects of MIPP versus MOMIPP on the morphology of U251 cells FIG. 40. Comparison of the effects of MOMIPP versus MIPP on colony-forming ability of U251 glioblastoma cells after long term (2 days) or short term (4 hours) treatment.
Figure 40:
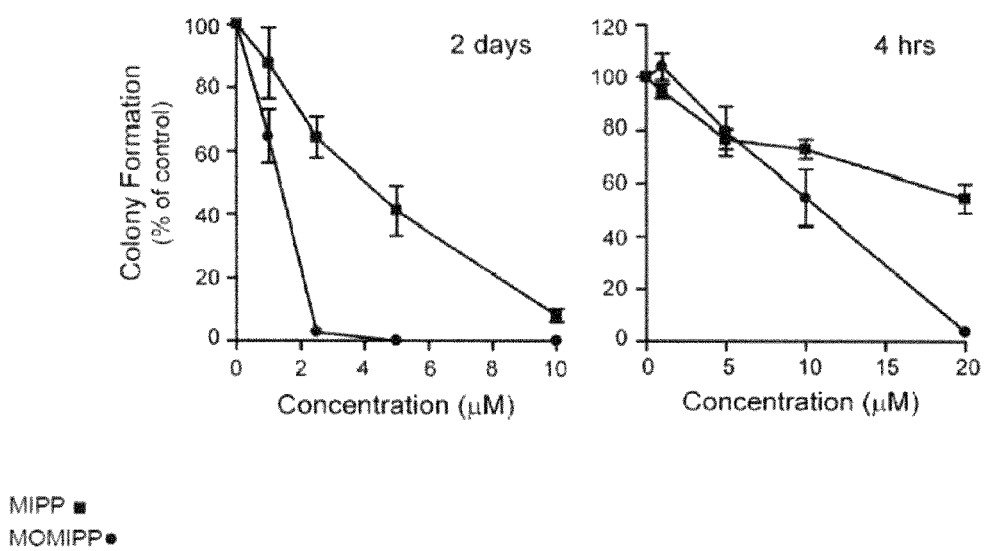

In contrast, the cells treated with MIPP initially underwent vacuolization on days 1 and 2, but tended to recover, especially at the lower concentrations of the compound (FIG. 39). These studies show that a single application of MOMIPP has a more sustained effect than MIPP on cell morphology and cell viability. The difference between the two compounds was underscored when colony-forming assays were used to evaluate proliferative capacity and long-term cell viability (FIG. 40). MOMIPP was shown to be more effective than MIPP in reducing colony formation when cells were treated for 2 days (FIG. 40).

In yet another embodiment, it is shown that when treatment was shortened to just 4 h, MOMIPP was still more effective than MIPP, but higher concentrations of both compounds were required to reduce colony formation (FIG. 40).

Figure 41:
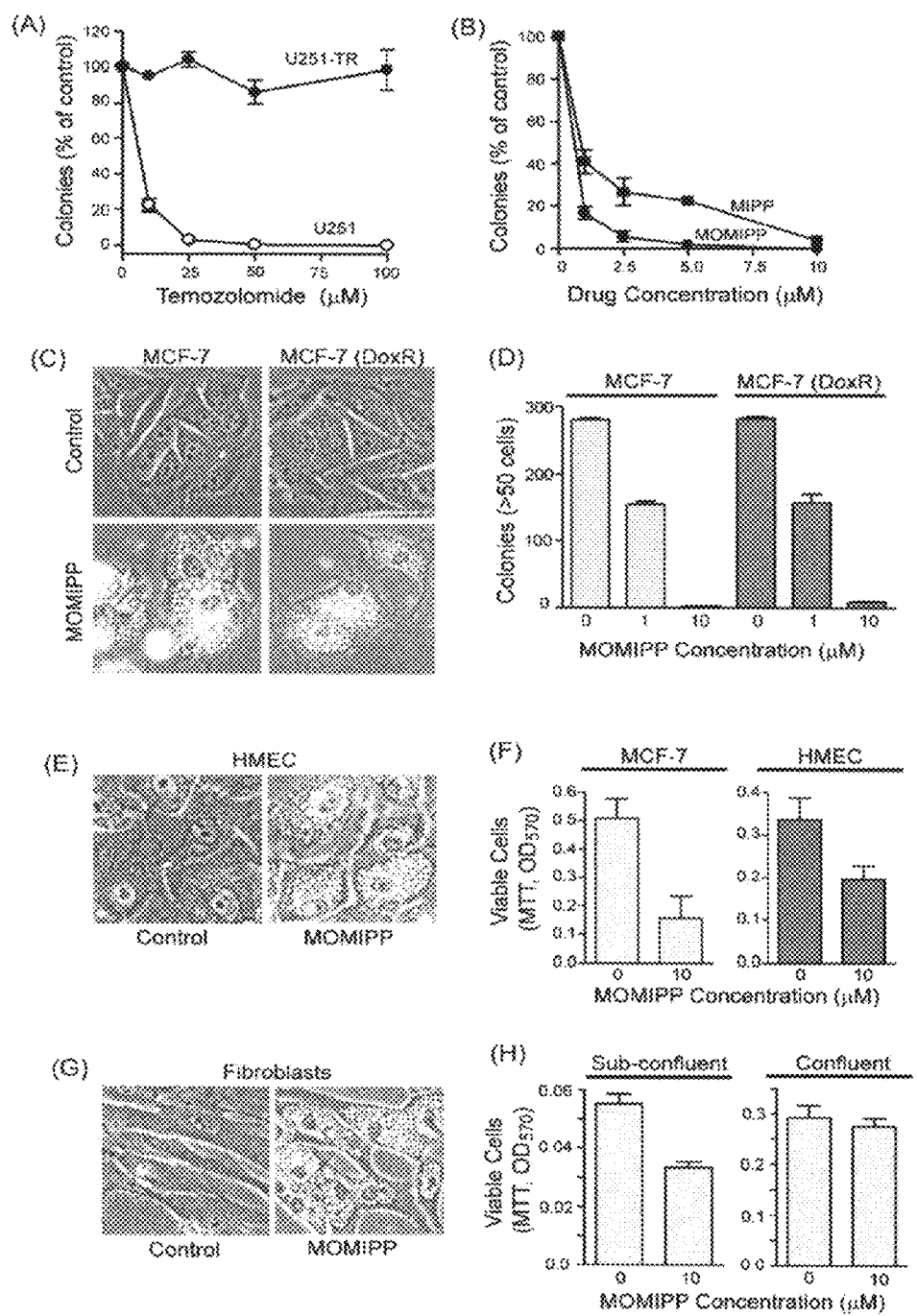
FIGS. 41A-41H. MOMIPP effectively inhibits the viability of drug-resistant GBM cells and breast cancer cells.

The methuosis-inducing compounds are effective for targeting temozolomide (TMZ)-resistant glioblastoma. As shown in FIGS. 41A and 41B, both MIPP and MOMIPP induced methuosis and reduced cell viability in the TMZ-resistant cells, but the efficacy of MOMIPP was shown to be superior to MIPP.

The ability of MOMIPP to kill drug-resistant tumor cells by methuosis extends beyond glioblastoma. For example, comparable levels of MOMIPP-induced methuosis was observed in parental and doxorubicin-resistant MCF-7 breast cancer cells, as shown in FIGS. 41C-41D, 45 and 46.

Figures 42, 43:
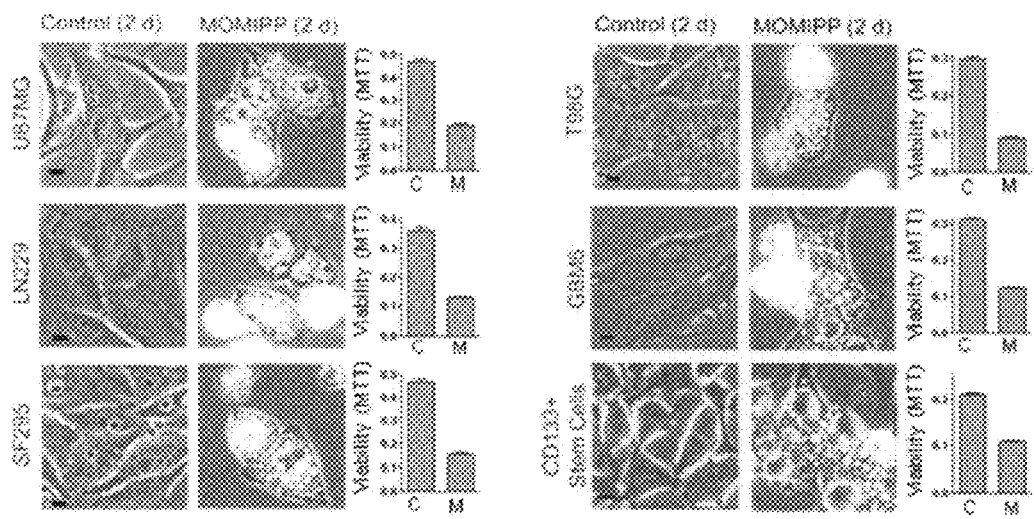
FIG. 42. Effects of MOMIPP on the morphology and viability of multiple human glioblastoma cell lines, including CD133+ GBM stem cells.
FIG. 43. Effects of MOMIPP on colony-forming ability of multiple human GBM cell lines.

The methuosis-inducing activity of MOMIPP was further shown to extend to multiple human GBM cell lines with different genetic backgrounds, as shown in FIGS. 42 and 43.

Figure 44:
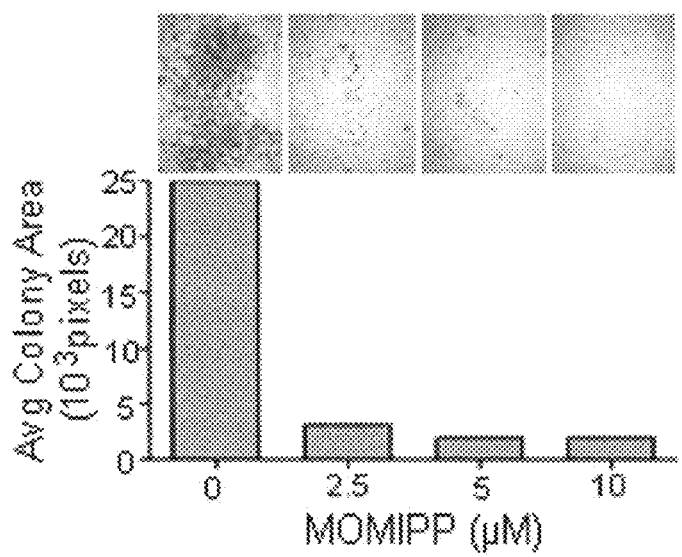
FIG. 44. MOMIPP causes vacuolization and inhibits colony formation in cultured GBM stem cells isolated directly from a human tumor.

The methuosis-inducing activity of MOMIPP was also shown to extend to human $CD133^+$ GBM stem cell populations, as shown in FIGS. 42 and 44.

The mechanism by which MIPP causes cellular vacuolization and death can involve three steps; 1) a transient increase in macropinocytotic activity, 2) rapid homotypic fusion of the macropinosome-derived vesicles to form vacuoles that acquire late endosomal characteristics, and 3) failure of the resulting vacuoles to recycle or fuse with lysosomes, leading to their progressive accumulation. Similar steps can be involved in the death mechanism triggered by MOMIPP, as shown in FIGS. 37-44.

Ras-induced methuosis depends on activation of Rac1 and reciprocal inactivation of Arf6, leading to hyperstimulation of macropinocytosis and defects in macropinosome recycling and downstream trafficking. However, the measurements of the activation states of Rac1 and Arf6 did not reveal any changes in MIPP treated cells. On the other hand, MIPP is shown to have profound effects on the activities of Rab5 and Rab7, decreasing the amount of active Rab5 and increasing the amount of Rab7. This shows that the compound operates directly on the machinery that regulates the trafficking and fusion of endosomal vesicles.

Rab5 controls receptor-mediated (clathrin-dependent) endosome formation, homotypic fusion, and delivery of early endosomes to the sorting/recycling compartment. The latter serves as a "way station" from which early endosomes can either recycle to the cell surface or progress to late endosomes in a multi-step process involving Rab5-Rab7 conversion.

While not wishing to be bound by theory, it is further disclosed herein that the main consequence of the MIPP-induced decrease in active Rab5 can occur after the initial formation of macropinosomes. That is, the nascent vesicles formed during the initial burst of macropinocytotic activity fail to fuse with EEA1-positive early endosomes and thus do not enter the sorting/recycling compartment. Instead they immediately acquire the capability to recruit LAMP1 and Rab7. The resulting vesicles then undergo abnormal homotypic fusions to form progressively larger vacuoles in a manner that requires activity of the $H^+$-ATPase.

Despite their ability to undergo homotypic fusion, the apparent inability of the Rab7-positive vacuoles to merge with lysosomes showing that they can lack some of the key protein components of complexes that are required for heterotypic tethering and fusion of late endosomes with lysosomes and autophagosomes (e.g., HOPS, trans-SNARE). This can explain the progressive accumulation of the vacuoles and the overall increase in the amount of active Rab7, as GAP-mediated GTP-hydrolysis that would normally coincide with endosome-lysosome fusion fails to occur.

Based on the examination of several cancer cell lines, it is shown that the ability of MIPP to induce methuosis extends beyond glioblastoma. It is further disclosed herein that MIPP can also trigger vacuolization and a modest reduction of cell proliferation/viability in normal proliferating cells, which can lead to delivery of such compounds to tumors.

In general, the terms and phrases used herein have their art-recognized meaning, which can be found by reference to texts, journal references and contexts known to those skilled in the art.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

When a group of substituents is disclosed herein, it is understood that all individual members of that group and all subgroups, including any isomers and enantiomers of the group members, are disclosed separately. When a Markush group or other grouping is used herein, all individual members of the group and all combinations and subcombinations possible of the group are intended to be individually included in the disclosure. It is intended that any one or more members of any Markush group or listing provided in the specification can be excluded from the invention if desired. When a compound is described herein such that a particular isomer or enantiomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Specific names of compounds are intended to be exemplary, as it is known that one of ordinary skill in the art can name the same compounds differently.

Every formulation or combination of components described or exemplified herein can be used to practice the invention, unless otherwise stated.

All publications mentioned herein are incorporated herein by reference for the purpose of describing and disclosing components that are described in the publications that might be used in connection with the presently described invention.

The following abbreviations are applicable. Baf-A, bafilomycin A1; DMEM, Dulbecco's modified Eagle medium; DMSO, dimethyl sulfoxide; FBS, fetal bovine serum; GAP, GTPase activating protein; LAMP1, lysosomal-associated membrane protein 1; LC3, microtubule-associated protein light chain 3; MIPP, 3-(2-Methyl-1H indol-3-yl)-1-(4-pyridinyl)-2-propen-1-one; MOMIPP, [trans-3-(5-Methoxy-2-methyl-1H-indol-3-yl)-1-(4-pyridinyl)-2-propene-1-one]; MTT; 3-(4,5-dimethylthiazol-2-yl)-2,5-diphenyl tetrazolium bromide; SAR, structure-activity relationships; and TMZ, temozolomide.

The definitions are provided to clarify their specific use in the context of the invention.

Thus, as used herein, the term "alkyl" includes straight, branched and cyclic alkyl groups, having up to 10 carbon atoms. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

Illustrative aliphatic groups thus include, but are not limited to, for example, methyl, ethyl, n-propyl, isopropyl, cyclopropyl, —$CH_2$-cyclopropyl, allyl, n-butyl, secbutyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl-n, hexyl, sec-hexyl, cyclohexyl, —$CH_2$cyclohexyl moieties and the like, which again, can bear one or more substituents. Illustrative alkynyl groups include, but are not limited to, for example propargyl.

"Aryl" refers to an unsaturated aromatic or heteroaromatic carbocyclic group of from 1 to 15 carbon atoms having a single ring (e.g. phenyl) or multiple condensed rings (e.g., naphthyl or anthryl). Preferred aryls include substituted aromatic C6-12 carbocycle; unsubstituted aromatic C1-10 heterocycle; substituted aromatic C1-10 heterocycle; wherein when substituted, the substitution is —XR.

Aralkyl refers to an alkyl herein connected to an aryl herein.

Unless otherwise constrained by the definition for the aryl substituent, such aryl groups can optionally be substituted with from 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, acylamino, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl) amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic, and the like.

"Halogen" refers to fluoro, chloro, bromo and iodo and preferably is either chloro or bromo.

"Heterocycle" or "heterocyclic" refers to a saturated or unsaturated group having a single ring or multiple condensed rings, from 1 to 8 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, aminoacyl, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsynumetric di-substituted amines having different substituents selected from alkyl, substituted alkyl, aryl, heteroaryl and heterocyclic, and the like. Such heterocyclic groups can have a single ring or multiple condensed rings. Preferred saturated heterocyclics include morpholino, piperidinyl, and the like; and preferred unsaturated heterocycles include pyridyl and the like.

Examples of heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, piperidinyl, pyrrolidine, tetrahydrofuranyl, and the like.

It will be appreciated by one of ordinary skill in the art that asymmetric centers can exist in the compounds of the present invention. Thus, inventive compounds and pharmaceutical compositions thereof can be in the form of an individual enantiomer, diastereomer or geometric isomer, or can be in the form of a mixture of stereoisomers. It is to be understood that the invention encompasses all possible isomers such as geometric isomers, optical isomers, stereoisomers and tautomers based on an asymmetric carbon, which can occur in the structures of the inventive compounds, and mixtures of such isomers and compositions comprising those compounds, and is not limited to the specific stereochemistry shown for the compounds disclosed in the present specification. It will be further appreciated that the absolute stereochemistry of some of the compounds recited in the Exemplification herein cannot have been determined, and that when a stereochemistry was assigned for those compounds it is meant to be tentative and to indicate that a set of diastereomers exists for those compounds and/or that a diastereomer was isolated in pure form. Furthermore, it will be appreciated that certain of the compounds disclosed herein contain one or more double bonds and these double bonds can be either Z or E, unless otherwise indicated. In certain embodiments, the compounds of the invention are enantiopure compounds. In certain other embodiments, mixtures of stereoisomers or diastereomers are provided.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof.

Furthermore, it will be appreciated by one of ordinary skill in the art that the synthetic methods, as described herein, utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction.

For example, oxygen, sulfur, nitrogen and carbon protecting groups can be utilized. Certain exemplary oxygen protecting groups include, but are not limited to methyl ethers, substituted methyl ethers (e.g., MOM (methoxymethyl ether), MTM (methylthiomethyl ether), BOM (benzyloxymethyl ether), PMBM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TB DMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals.

Exemplary nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, inline derivatives, and enamine derivatives, to name a few. As will be appreciated by those of ordinary skill in the art, a variety of additional equivalent protecting groups can be utilized in accordance with the present invention.

It will be appreciated that the compounds, as described herein, can be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure can be substituted with more than one substituent selected from a specified group, the substituent can be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen can have hydrogen substituents and/or any permissible substituents of organic compounds described herein which satisfy the valencies of the heteroatoms.

Furthermore, this invention is not intended to be limited in any manner by the permissible substituents of organic compounds. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

As used herein, the term "patient" is intended to include living organisms in which certain conditions as described herein can occur. Examples include humans, monkeys, cows, sheep, goats, dogs, cats, mice, rats, and transgenic species thereof. In a preferred embodiment, the patient is a primate. In an even more preferred embodiment, the primate is a human. Other examples of subjects include experimental animals such as mice, rats, dogs, guinea pigs, cats, goats, sheep, pigs, and cows. The experimental animal can be an animal model for a disorder, e.g., a transgenic mouse with cancer.

As used herein, the term "$IC_{50}$" refers to an inhibitory dose which is 50% of the Maximum response obtained.

Dosing

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount can vary according to the response of the subject. The practitioner responsible for administration will, in any event, determine the concentration of active ingredient(s) in a composition and appropriate dose(s) for the individual subject.

In certain embodiments, pharmaceutical compositions can comprise, for example, at least about 0.1% of an active compound. In other embodiments, an active compound can comprise between about 2% to about 75% of the weight of the unit, or between about 25% to about 60%, for example, and any range derivable therein. Naturally, the amount of active compound(s) in each therapeutically useful composition can be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens can be desirable.

In other non-limiting examples, a dose can also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Identification of Methuosis-Inducing Molecules

The examples describe the particular assay systems used to identify methuosis-inducing molecules as described herein. As shown in the Examples, and as would be readily appreciated by those of ordinary skill in the art, additional or alternative methuosis-inducing molecules can readily be identified by applying the same screen to other chemical compounds.

For instance, extracts containing natural products are often used as sources of test compounds for biological assays. Alternatively or additionally, synthetic compounds can be utilized. As will be appreciated by those of ordinary skill in the art, the development of combinatorial chemistry and split-pool synthesis techniques have added to the repertoire complex compound libraries, the products of laboratory syntheses, as a source of small molecules to be screened for compounds with biological activity. However, small molecules synthesized by parallel synthesis methods and by traditional methods (one-at-a-time synthesis and modifications of these structures) can also be utilized in the compositions and methods of the present invention, as can naturally occurring compounds, or other collections of compounds.

As will be realized by one of ordinary skill in the art, in split-and-pool techniques, a mixture of related compounds can be made in the same reaction vessel, thus substantially reducing the number of containers required for the synthesis of very large libraries, such as those containing as many as or more than one million library members. As an example, a solid support bound scaffold can be divided into n vessels, where n represents the number of species of reagent A to be reacted with the support bound scaffold. After reaction, the contents from n vessels are combined and then split into m vessels, where m represents the number of species of reagent B to be reacted with the support bound scaffold. This procedure is repeated until the desired numbers of reagents are reacted with the scaffold structures to yield a desired library of compounds.

As mentioned above, the use of parallel synthesis methods are also applicable. Parallel synthesis techniques traditionally involve the separate assembly of products in their own reaction vessels. For example, a microtiter plate containing n rows and m columns of tiny wells which are capable of holding a small volume of solvent in which the reaction can occur, can be utilized. Thus, n variants of reactant type A can be reacted with m variants of reactant type B to obtain a library of n×m compounds.

Preparation of Methuosis-Inducing Molecules

Once identified, methuosis-inducing molecules of the present invention can be prepared by any available means. In some cases, the methuosis-inducing molecules can be compounds that occur naturally and therefore can be prepared from a natural source using known purification and isolation technologies. In other cases, the methuosis-inducing molecules cannot be naturally-occurring, or cannot be readily isolatable from a natural source, and therefore can instead be prepared using synthetic techniques, as is known in the art. Any appropriate synthetic techniques can be employed, including those that utilize only chemical reagents or those that utilize biological reagents such as synthetic enzymes. Alternatively or additionally, synthetic and isolationary techniques can be combined in the preparation of inventive methuosis-inducing molecules. The terms "isolated" or "substantially purified" as used interchangeably herein refer to vacuolin compounds in a non-naturally occurring state. The compounds can be substantially free of cellular material or culture medium when naturally produced, or chemical precursors or other chemicals when chemically synthesized.

Therapeutic Uses

As described herein, inventive methuosis-inducing molecules induce cell death. In this regard, the present invention is useful in a number of pathological applications. Certain applications are mentioned below; others will be apparent to those of ordinary skill in the art.

Therefore, according to the present invention, methuosis-inducing molecules can be used to induce cell death of cancer cells. For example, the present invention is useful in treating cancers of the brain, lung, bladder, liver, spleen, pancreas, bone, colon, stomach, breast, prostate, ovary, central nervous system and skin. For example, glioblastoma and breast carcinoma can be treated according to the present invention.

Research Uses

In addition to the various pharmaceutical uses described above, methuosis-inducing compounds of the present invention have utility in a variety of research applications, e.g., in vitro assays, including, for example, as chemical probes. Those of ordinary skill in the art will appreciate that the field of chemical genetics attempts to identify chemical agents with definable effects on biological events, pathways, or products so that these agents can be used as tools to analyze the relevant biological events, pathways, or products. Methuosis-inducing molecules of the present invention are particularly well suited for such studies. Accordingly, the present invention also includes assays, e.g., in vitro assays, utilizing the methuosis-inducing molecules of the present invention to analyze vacuolization, intracellular trafficking, antigen presentation, membrane fusion events, and related cellular processes. Furthermore, the methuosis-inducing molecules of the present invention can also be used in screening assays to identify second generation methuosis-inducing molecules, e.g., molecules having modified chemical structures which function as methuosis-inducing molecules. Azide, propargyl or other forms of the methuosis-inducing molecules of the present invention can be used in a variety of cell-based or molecular screening assays to identify specific protein targets that bind to such molecules.

Formulations

As described herein, inventive methuosis-inducing compounds can be utilized in any of a variety of contexts, and can be formulated appropriately according to known principles and technologies.

For example, the methuosis-inducing molecules can be provided in substantially pure form, in an organic solvent such as DMSO. Alternatively or additionally, methuosis-inducing molecules can be formulated as a pharmaceutical composition, for example being combined with a pharmaceutically acceptable carrier. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals with little or no undue toxicity, irritation, allergic response and the like, and are commensurate with a reasonable benefit/risk ratio. Pharmaceutically acceptable salts of amines, carboxylic acids, and other types of compounds, are well known in the art (see, for example, Berge, et 3.1. J. Pharmaceutical Sciences, 66:1-19, 1977, incorporated herein by reference).

The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof can, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The methuosis-inducing molecules disclosed herein can be formulated or administered together with any other known agent having a complementary biological effect. For example, methuosis-inducing molecules can be combined with steroids or other immunomodulating agents in order to regulate immunological events as described herein.

It will be appreciated that the compounds and compositions, according to the method of the present invention, can be administered using any effective amount and any effective route of administration. Thus, the expression "effective amount" as used herein, refers to a sufficient amount of agent to result in vacuolization and/or inhibition of compartment trafficking as described herein. The exact amount required can vary from subject to subject, depending on the species, age, and general condition of the subject, the severity of the infection, the particular therapeutic agent, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment.

The specific therapeutically effective dose level for any particular patient or organism can depend upon a variety of factors including the disorder being treated and the severity of the disorder; the activity of the specific compound employed; the specific composition employed; the age, body weight, general health, gender and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention can be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.R and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension or crystalline or amorphous material with poor water solubility. The rate of absorption of the drug then depends upon its rate of dissolution that, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable nonirritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art.

In such solid dosage forms the active compound can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as can be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In other embodiments of the invention, methuosis-inducing compounds, or compositions containing them are packaged into a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and can also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EXAMPLES

Example 1

Methods and Materials

Test Compounds and Reagents

Compounds I, II (MIPP), and IV were purchased from Chembridge Corporation. Compound III was purchased from TimTec, LLC. Each of these compounds was stored at −20° C. as a 5 mg/ml stock solution in DMSO, and then diluted to the mentioned final concentration in cell culture medium. Filipin and bafilomycin A1 were obtained from Sigma-Aldrich. Filipin was stored at −20° C. as a 50 mg/ml stock in DMSO and bafilomycin A1 was stored at −20° C. as a 10 µM stock in DMSO. EHT 1864 was provided by Exonhit Therapeutics. z-VAD-fmk was purchased from Bachem.

Library Compounds

Compounds 1-8 used for initial screening of methuosis-inducing activity (FIG. 1) have identification numbers as follows: 1, 5224450; 2, 5224466; 3, 5312531; 4, 7995005; 5, 7916760; 6, 6161388; 7, 5267766; and 8, 6155359. All compounds are certified by the vendor to be at least 90% pure with NMR confirmation of structure.

General Methods

Reagents and starting materials were obtained from commercial suppliers without further purification. Thin layer chromatography (TLC) was done on 250 µm fluorescent silica gel 1B-F plates and visualized with UV light. Flash column chromatography was performed using silica gel 230-400 µm mesh size. Melting points (MP) are uncorrected. Nuclear magnetic resonance (NMR) spectra were recorded on, either, a 600, 400 or 200 MHz instrument. Peak locations were referenced using the residual solvent peak (7.26 and 77.16 for CDCl3 1H and 13C, respectively, and 2.50 and 39.51 for DMSO 1H and 13C). Proton coupling constants (J values) and signals are expressed in hertz using the following designations: s (singlet), d (doublet), br s (broad singlet), m (multiplet), t (triplet), dd (doublet of doublets) and qd (quintet of doublets). NMR spectra are available in the supplementary information.

Cell Culture

U251 human glioblastoma cells were purchased from the DCT Tumor Repository. All other cell lines were obtained from the American Type Culture Collection. Cell lines were passaged for fewer than six months prior to use. Normal human skin fibroblasts were derived from a skin biopsy. Unless stated otherwise, cell lines were maintained in Dulbecco's modified Eagle medium (DMEM) with 10% (v/v) fetal bovine serum (FBS) at 37° C. with 5% $CO_2$/95% air. MCF-10A cells were maintained in DMEM+Ham's F12 (1:1) containing 5.0% horse serum, 20 ng/ml EGF, 0.5 µg/ml hydrocortisone, 100 ng/ml cholera toxin, and 10 µg/ml insulin, as described. Colonies of temozolomide-resistant U251 cells were selected by maintaining the parental U251 cells in medium containing 100 µM temozolomide for 24 days, with replenishment of the medium and drug every three days. Colonies were then picked and plated into a 12-well dish and exposed to escalating concentrations of temozolomide. The clone used in the present study (U251-TR) is maintained routinely in medium with 300 µM temozolomide. To generate cell growth curves, U251 cells were plated in 35 mm dishes (100,000 cells/dish, FIG. 4B) and allowed to attach for 24 h. Thereafter, cells were treated with the mentioned compounds dissolved in DMSO or with vehicle alone. At daily intervals, three parallel cultures were harvested from each group by trypsinization and aliquots of cell suspension were counted in a Coulter Z1 particle counter. Phase-contrast images of live cells were obtained using an Olympus IX70 inverted microscope equipped with a digital camera and SPOT imaging software.

Live Cell Imaging with Fluorescent Tracers

Lucifer yellow (LY) was purchased from Invitrogen/Molecular Probes. Labeling of endocytic compartments with this fluid-phase tracer was performed as previously described. Labeling of intracellular acidic compartments with Lysotracker Red DND-99 and staining for cathepsin B activity with Magic Red RR were performed as described previously. ER-Tracker Blue-White DPX was used to label the endoplasmic reticulum following the directions supplied by the manufacturer. Phase-contrast and fluorescent images of the living cells were acquired on an Olympus IX70 inverted microscope equipped with a digital camera and SPOT imaging software or on a Nikon Eclipse TE2000U fluorescence microscope with a digital camera and NIS-Elements AR software.

Time-Lapse Microscopy 200,000 U251 cells were plated in a 35 mm glass-bottom microwell culture dish. The day after plating, the cells were treated with 10 µM MIPP in phenol red-free DMEM supplemented with 10% FBS. The dish was immediately placed in a humidified Live Cell chamber equilibrated with 5% $CO_2$ at 37° C. The chamber was placed on the stage of an Olympus IX80 inverted microscope, equipped with a digital camera and Slidebook software. The software was set to automatically acquire phase-contrast images every 30 sec for the designated period of time.

Treatment of Cells with Filipin, Bafilomycin A1 or EHT 1864.

To inhibit clathrin-independent endocytosis, U251 cells were washed twice with serum-free DMEM, then pretreated for 30 min with DMEM+0.5% BSA in the presence or absence of 12 µg/ml filipin. Following the pretreatment, MIPP was added to the dishes at a final concentration of 10 µM and phase-contrast images were acquired 100 min later.

To inhibit the vacuolar-type $H^+$ ATPase, U251 cells were pretreated for 1 h with 0.1 µM bafilomycin A1 or an equivalent volume of DMSO. At the end of the hour, 10 µM MIPP, or an equivalent volume of DMSO, was added without a medium change. Phase-contrast images of the cells were acquired 1 h after the addition of MIPP.

To determine if inhibition of the Rac1 GTPase would block the accumulation of vacuoles, U251 cells were treated for 24 h with 10 µM MIPP in the presence or absence of 25 µM EHT 1864. The percentage of vacuolated cells in the population was determined by scoring at least 100 cells in multiple phase-contrast photomicrographs for each condition. Cells containing three or more phase-lucent vacuoles with diameters ≥0.5 µm or >10 smaller vacuoles (0.1-0.5 µm) were scored as positive. For comparison, the effect of EHT 1864 on Ras-induced vacuolization was also determined. U251 cells were nucleofected with pCMV5-Myc-H-Ras (G12V), then immediately plated into medium with or without 25 µM EHT 1864. After 24 h, phase-contrast images were taken and the number of vacuolated cells was scored as described above.

Pull-Down Assays to Measure the Activation States of GTPases

Assays for activated Rac1 and Arf6 were performed using EZ-Detect Rac1 or Arf6 activation kits. These assays employ either a GST-fusion protein containing the p21-binding domain of p21-activated protein kinase 1 (PAK1) to selectively bind active Rac1 in whole cell lysates, or GST-GGA3 (Golgi-associated gamma adaptin ear-containing Arf binding protein 3) to pull down active Arf6. The active Rac1 or Arf6 collected on the glutathione beads were subjected to western blot analysis and the chemiluminescence signals were quantified using Alpha Innotech Fluor Chem HD2 imaging system. The values for active protein in each sample were normalized to α-tubulin. Results were expressed as either the total active Rac1 or Arf6, or the ratio of the active GTPase to the total Rac1 or Arf6 measured in aliquots of the cell lysate.

GST-fusion proteins were produced in *E. coli* BL21 (DE3) pLysS and the fusion proteins were bound to glutathione-sepharose 4B beads. Pull-down assays for active Rab5 using the GST-Rabaptin-5 beads were performed. Assays for active Rab7 were performed. For each determination cell lysates were prepared from ten pooled 10 cm cultures. Monoclonal antibodies against Rab5 or Rab7 were used to probe western blots of the proteins collected on the beads. Results were quantified and normalized as described above for Rac1 and Arf6.

Confocal Fluorescence Microscopy

U251 cells were nucleofected with pEGFP-Rab7 or pEGFP-Rab5, then plated onto coverslips in 60 mm dishes. The day after nucleofection, the cells were treated with 10 µM MIPP. For colocalization experiments, cells that had been treated with MIPP for 24 h were prepared for immunofluorescence microscopy. All primary antibodies were detected by incubation with goat anti-mouse IgG conjugated to Alexa Fluor 568. Cells were examined by confocal microscopy using a Leica TCS SP5 system with 488- and 561-nm laser excitation. Images were acquired with the LASAF software on the system.

Electron Microscopy

U251 cells were exposed to 10 µM MIPP for 48 h, then prepared for electron microscopy. The cells were examined under a Philips CM 10 transmission electron microscope.

Western Blot Analysis

The antibody for PARP was purchased from BD Biosciences. Analysis methods sued were protein determination, SDS-PAGE and western blot analysis.

Cell Viability

Cell viability was measured using a 3-(4,5-dimethylthi-azol-2-yl)-2,5-diphenyl tetrazolium bromide (MTT)-based assay. A 5 mg/ml MTT stock solution was prepared in phenol-red free RPMI 1640. Cells were seeded in 96-well plates, with four replicate wells for each culture condition. On the day of the assay, 10 µl of the MTT solution was added directly to 10

µl in each well and the cells were incubated for 3-4 h at 37° C., with 5% $CO_2$. At the end of the incubation, 100 µl of MTT solvent (0.1N HCl in isopropanol, containing 0.1% NP-40) was added to each well. The plates were incubated for an additional 5 min at 37° C., 5% $CO_2$, then quantified for absorbance at 570 nm on a SpectraMax Plus 384 plate reader.

For colony-forming assays, cells were plated in 100 mm dishes at 2,500 (U251 and U251-TR) or 1,500 (all other cell lines) cells per dish. Beginning on the day after plating, the cells were exposed to 10 µM MIPP for 2 days, with the medium and drug replenished after 1 day. The cells were fed fresh medium without drug every 2 to 3 d for a period of 10-21 days. To visualize the colonies, the dishes were washed with PBS, fixed for 10 min with ice-cold 100% methanol, and stained with 1% crystal violet in 35% methanol. After 2-3 washes with water, colonies containing at least 50 cells were counted using a dissecting microscope or a Protocol 2 colony counter.

To compare the levels of ATP in MIPP-treated glioblastoma cells versus controls treated with an equivalent volume of DMSO, the cells were harvested by trypsinization and assayed using the CellTiter Glo kit from Promega according to the manufacturer's instructions.

Statistical Significance

Statistical significance of differences in colony formation or other parameters (e.g., GTPase activation) involving comparisons between control and MIPP-treated cells were evaluated by Student's two tailed t-test.

Example 2

Small Molecules that Induce Cytoplasmic Vacuolization

Disclosed herein is Compound I which caused a striking accumulation of numerous phase-lucent cytoplasmic vacuoles within 4 h when applied to U251 glioblastoma cells (FIG. 1). When added at a concentration of 1 µM, the morphological effects of Compound I were transient, with most of the vacuoles dissipating by 24 h (FIG. 1). However, at 10 µM, the morphological effects of Compound I persisted for 24 h and beyond. A search of the broader 700,000 compound Chembridge collection yielded several additional compounds with >75% similarity to Compound I. Of these, 3(2-methyl-1H-indol-3-yl)-1-(4-pyridinyl)-2-propen-1-one (FIG. 1, Compound II), behaved similarly to Compound I when tested at 1 µM, but induced vacuoles that were larger and more numerous than those induced by Compound I when tested at a concentration of 10 µM (FIG. 1).

Closely related compounds with similar or identical indole ring structures, but with variations in the second aryl ring (Compound III) or the enone linker (Compound IV), showed no vacuole-inducing activity (FIG. 1). This showed that the effects of Compounds I and II were due to their interactions with specific intracellular targets, rather than non-specific effects on cellular membranes or intracellular pH. Compound III had no vacuole-inducing activity despite the fact that it shared the characteristics of a Michael acceptor with Compounds I and II. Based on these initial data, Compound II was selected for further study as a small molecule inducer of methuosis. The same compound is compound 2 in FIG. 29 and FIGS. 36 and 48. Hereafter it will be referred to by the acronym MIPP: i.e., 3-(2-methyl-1H indol-3-yl)-1-(4-pyridinyl)-2-propen-1-one.

Example 3

The Origin of the Vacuoles Induced by MIPP is Consistent with Methuosis

Figure 2:
FIGS. 2-5. Vacuoles induced by MIPP are derived from macropinosomes that undergo progressive fusion events and accumulate at a pre-lysosomal stage.

It is further disclosed herein that the vacuoles induced by MIPP were derived from macropinosomes, since this is a hallmark feature of methuosis. Macropinocytosis is a form of clathrin-independent endocytosis wherein intracellular vesicles are initially generated from projections of the plasma membrane termed ruffles or lamellipodia, which surround and trap extracellular fluid. Time lapse phase-contrast microscopy covering the period between 13-80 min after addition of MIPP revealed waves of macropinocytotic vesicles entering the U251 cells from regions of active membrane ruffling. The nascent vesicles can be seen coalescing with each other to form progressively larger vacuoles within the cytoplasm as shown in FIG. 1. Time lapse studies performed after the first 95 min showed a decline in the initial burst of macropinocytotic activity, although the vesicles already formed within the cell continued to enlarge by undergoing occasional fusion events as shown in FIG. 2.

Figure 3:
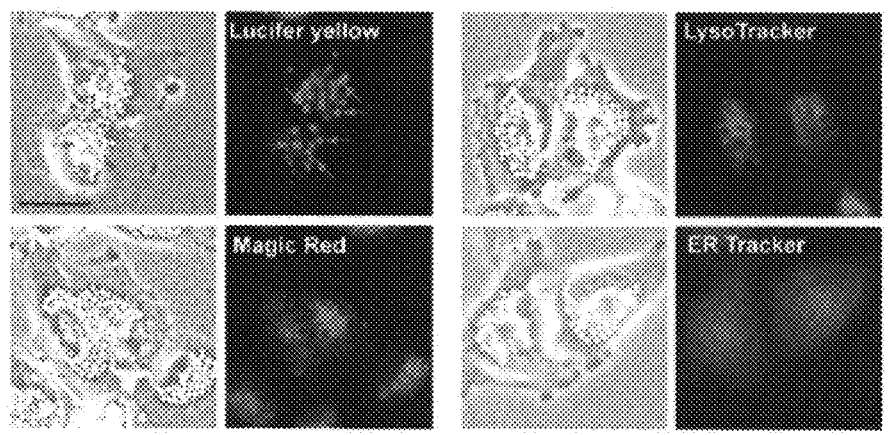

One of the features of methuosis is the incorporation of fluid-phase tracers like Lucifer yellow (LY) into large vacuoles that eventually fill the cytoplasm and disrupt the cells. Therefore, U251 cells were incubated with LY during the first 4 h after addition of the compound to show that the MIPP-induced vacuoles observed by phase-contrast microscopy were derived from macropinosomes. As shown in FIG. 3, LY was incorporated into most of the phase-lucent vacuoles.

Figure 4:
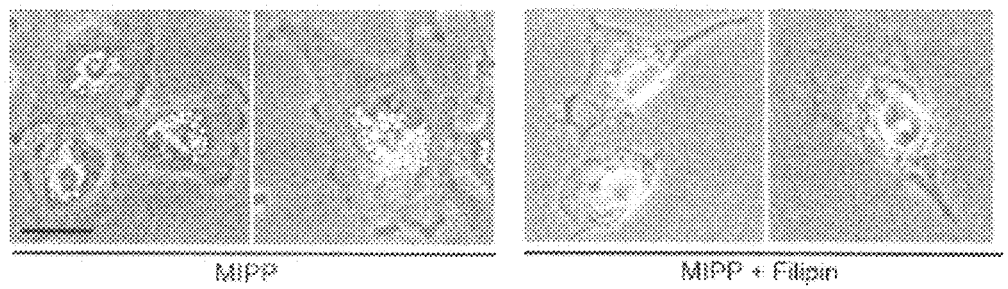

Macropinocytosis, which is a clathrin-independent form of endocytosis, is dependent on cholesterol-rich membrane microdomains. U251 cells were pre-incubated with or without filipin for 30 min prior to adding MIPP in order to establish that the MIPP-induced vacuoles were derived from clathrin-independent compartments. As shown in FIG. 4, cells treated with MIPP in the absence of filipin formed numerous vacuoles within the first 100 min after addition of the compound. In contrast, the cells treated with filipin failed to show the typical morphological response to MIPP. Thus, the majority of the vacuoles induced by MIPP are shown to originate from clathrin-independent macropinosomes, consistent with the mechanism of methuosis.

Example 4

Relationship of MIPP-Induced Vacuoles to Other Subcellular Compartments

In Ras-induced methuosis, the accumulated vacuoles eventually acquire some characteristics of late endosomes, but remain separate from the endoplasmic reticulum and the lysosomal or autophagosomal degradative compartments. The data disclosed herein show that the vacuoles induced by MIPP fit this profile. Live cell imaging of the phase-lucent vacuoles induced by MIPP showed no overlap with compartments labeled with LysoTracker Red, which identifies lysosomes based on their acidic pH, or Magic Red (RR), a cell permeable substrate that fluoresces when cleaved by the lysosomal protease, cathepsin B, as shown in FIG. 3. Nor did the vacuoles incorporate ER-Tracker, a marker for the endoplasmic reticulum, as shown in FIG. 3.

Bafilomycin A1 (Baf-A) is a specific inhibitor of the vacuolar-type $H^+$-ATPase, which plays an important role in the maintenance of endosomal membrane potential and luminal pH. Inhibition of $H^+$-ATPase with Baf-A impedes the formation of vesicular intermediates between early and late endosomes. Moreover, Baf-A strongly inhibits homotypic endosome fusion in vitro.

Figure 5:
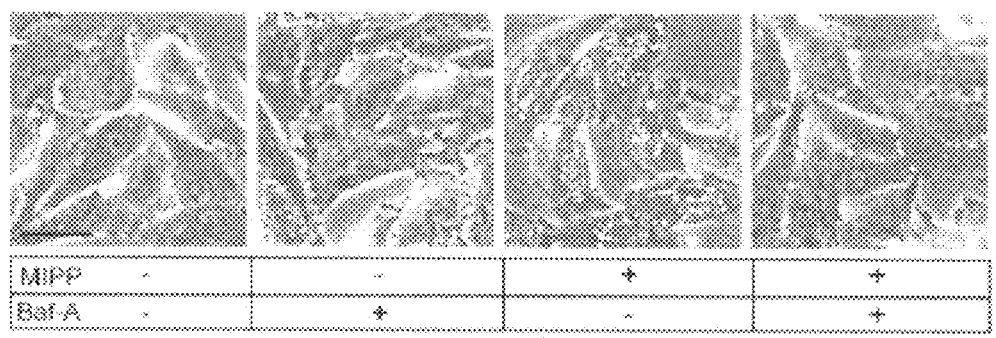

As shown in FIG. 5, short-term incubation of U251 cells with Baf-A by itself had no morphological effect on the cells, but the inhibitor completely abrogated the ability of the cells to generate vacuoles when they were exposed to MIPP. The effect of Baf-A is shown to be specifically related to its inhibition of the proton pump and the maintenance of endosomal membrane potential rather than general alkalinization of the endosomal compartment, since incubating cells with 1-5 mM ammonium chloride did not replicate the effects of Baf-A (data not shown).

Figure 6:
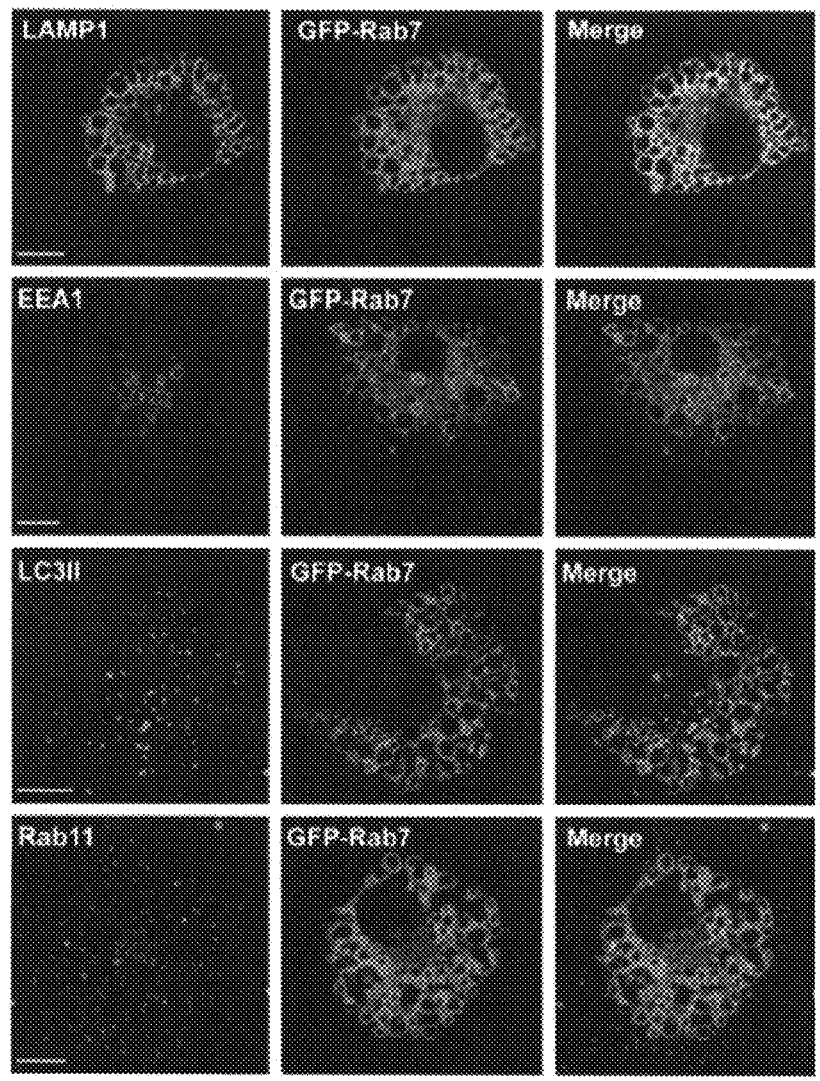
FIG. 6. Vacuoles induced by MIPP acquire characteristics of late endosomes, but remain distinct from autophagosomes.
Figure 22:
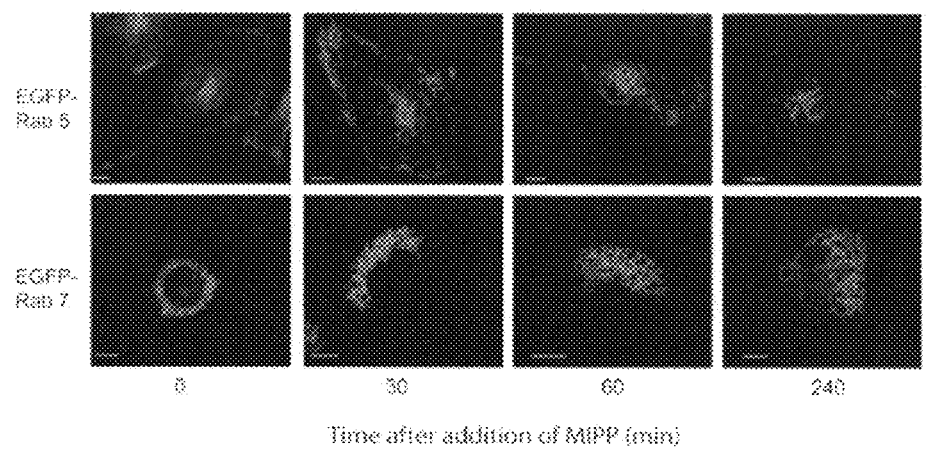
FIG. 22. U251 cells were transfected with expression vectors encoding EGFP-Rab5 or EGFP-Rab7.

Further disclosed herein is an analysis of distribution of markers for early and late endosomes and autophagosomes in cells treated with MIPP. Confocal microscopy demonstrated that by 24 h almost all of the vacuoles contained late endosomal markers, GFP-Rab7 and LAMP1, but showed little or no overlap with early endosomes (EEA1), recycling endosomes (Rab11), or autophagosomes (LC3II), as shown in FIG. 6. The presence of the late endosome marker, Rab7, can be detected in membranes of the vacuoles as soon as 30 min after the addition of MIPP, whereas the early endosome marker, Rab5, is generally absent from the majority of the vacuoles, as shown in FIG. 22. These data show that cellular vacuolization induced by MIPP involves fusion of nascent macropinosomes to form large vacuoles that can rapidly mature to acquire some characteristics of late endosomes, but cannot merge with lysosomes or autophagosomes.

Example 5

MIPP Affects the Activities of Endosomal Rab GTPases, but not Rac1 or Arf6

Figure 7:
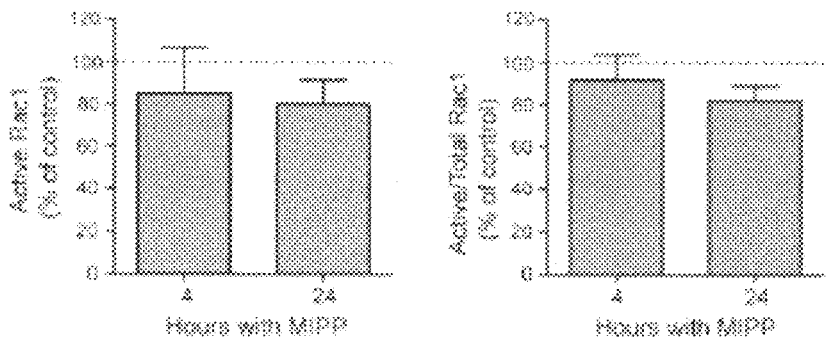
FIGS. 7-11. MIPP affects the activation states of Rab5 and Rab7, but not Rac1 or Arf6. In separate experiments U251 cells were treated with 10 μM MIPP for the indicated periods of time and then harvested for pull down assays to measure the relative amounts of active Rac1 (FIG. 7), Arf6 (FIG. 8), Rab5 (FIG. 9) or Rab7 (FIG. 10). As an additional control, the studies of Rab7 were conducted with cells treated with the inactive compound III instead of MIPP (FIG. 11).
Figure 8:
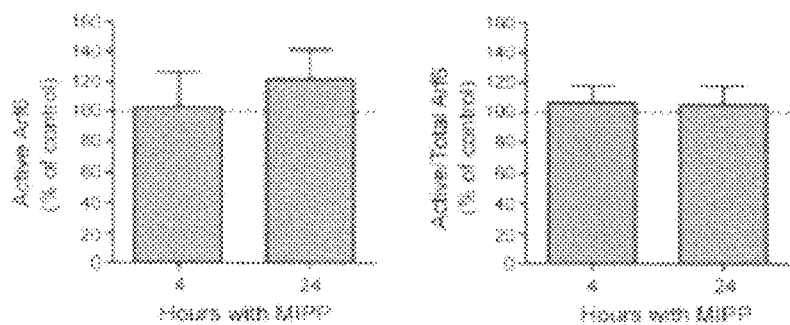
Figure 23:
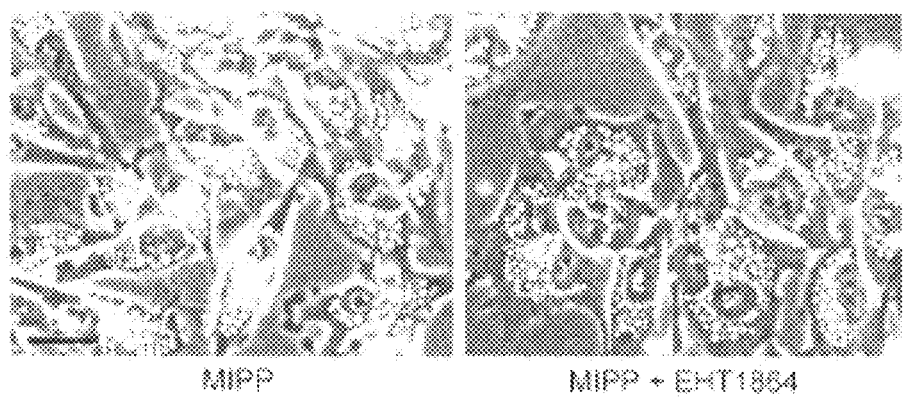
FIGS. 23-25. The Rac inhibitor, EHT 1864, does not block the induction of vacuoles by MIPP.
Figures 24, 25:
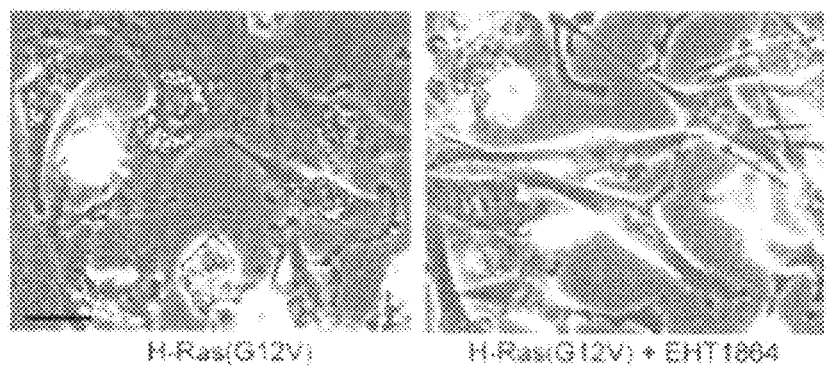

To begin to explore the molecular mechanism(s) through which MIPP causes endosomal vacuolization, the inventors considered possible parallels with the mechanism of methuosis triggered by over-expression of activated H-Ras. In the latter case, it is shown that development of the vacuolar phenotype requires activation of the Rac1 GTPase, with a concomitant reduction in the activation state of another GTPase, Arf6. However, when fusion proteins that bind specifically to the activated forms of Rac1 or Arf6 were used in pull-down assays to measure the activation states of these GTPases, it was shown that treatment of cells with MIPP had no significant effects on the amounts of active Rac1 (FIG. 7) or Arf6 (FIG. 8) at either 4 h or 24 h after addition of the compound. When U251 cells were incubated with MIPP in the presence of EHT 1864, a highly specific Rac inhibitor, there was no detectable effect on vacuole formation (FIG. 23). These data show that the mechanism of vacuolization induced by MIPP is different from that induced by Ras, in that it does not depend on activation of the Rac1 signaling pathway.

Figure 9:
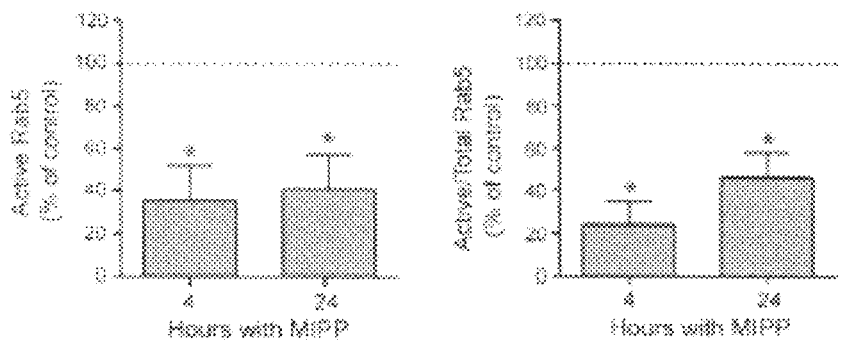
Figure 10:
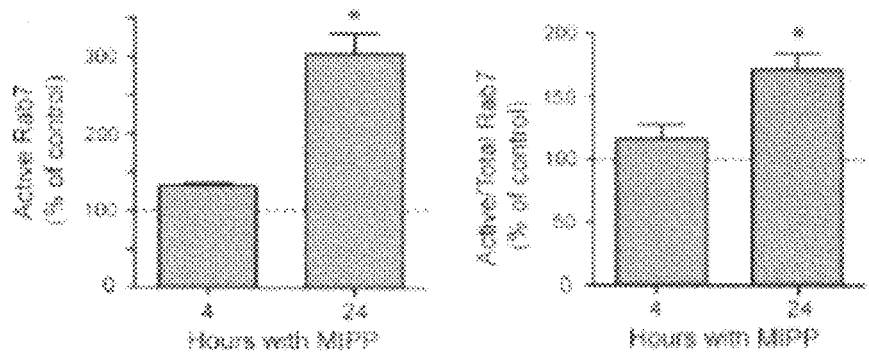

In light of the striking effects of MIPP on the clathrin-independent endosomal compartment, the inventors next focused on the Rab5 and Rab7 GTPases, which are known to function in early and late endosomal trafficking steps, respectively. The active GTP-bound forms of these proteins were measured in pull-down assays using GST-fusion constructs containing the Rab binding domains of rabaptin-5, for Rab5, or RILP, for Rab7. As shown in FIG. 9, MIPP caused a striking decline in the amount of active Rab5 at both 4 h and 24 h after treatment. In contrast, MIPP had the opposite effect on Rab7, with the amount of active Rab7 more than doubling by 24 h, as shown in FIG. 10.

Figure 11:
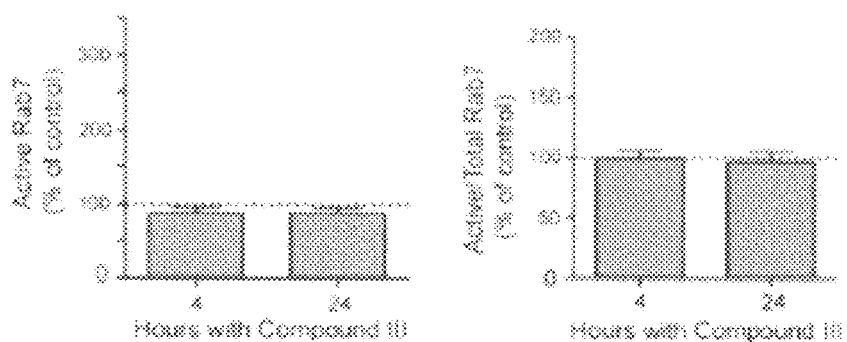

The changes in active Rab5 and Rab7 at 24 h were moderated somewhat (but still significant) when the results were normalized to the total Rab5 or Rab7 pools. This is due to the fact that the total amounts of Rab5 and Rab7 in the MIPP treated cells increased substantially by 24 h. It is important to note that the changes in the Rab activity were observed only in cells treated with the vacuole-inducing compound, MIPP. For example, in cells treated with the related but inactive Compound III (see FIG. 1), there was no change in the activation state of Rab7 (FIG. 11). This data shows that the vacuolization of macropinosome-derived endocytic compartments in MIPP-treated cells is related to opposite changes in the pools of active Rab5 and Rab7.

Example 6

MIPP Induces Non-Apoptotic Cell Death with the Characteristics of Methuosis

Further disclosed herein are a series of studies conducted to determine how closely the sequelae of MIPP treatment match the cell death phenotype associated with methuosis. The initial accumulation of vacuoles in glioblastoma cells undergoing Ras-induced methuosis is followed by a decline in cellular ATP levels, cell rounding, and detachment of cells from the substratum. Cell death ensues as the vacuoles expand to fill most of the cytoplasmic space and cell membrane integrity is disrupted. Characteristically, these alterations are not accompanied by morphological changes typical of apoptosis, such as nuclear chromatin condensation, nuclear fragmentation or cell shrinkage. Although caspase activation can be detected by examining PARP cleavage, cell death by methuosis cannot be prevented by treatment with caspase inhibitors. The data shown in FIGS. 12-17 show that the form of cell death induced by MIPP in U251 glioblastoma cells shares all of these characteristics.

Figure 12:
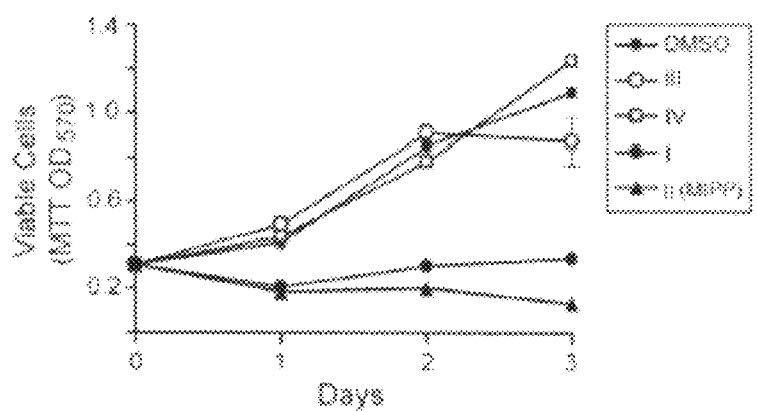
FIGS. 12-17. MIPP induced vacuolation leads to non-apoptotic cell death in glioblastoma cells.
Figure 13:
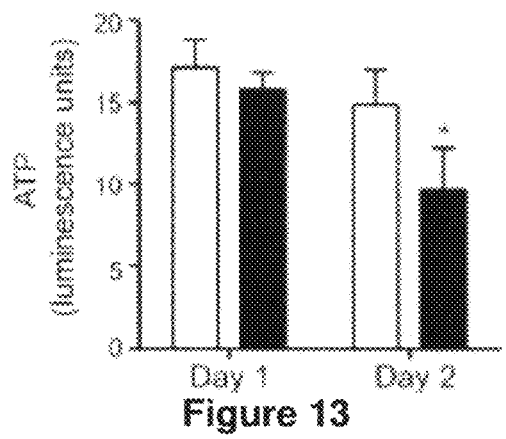
Figure 14:
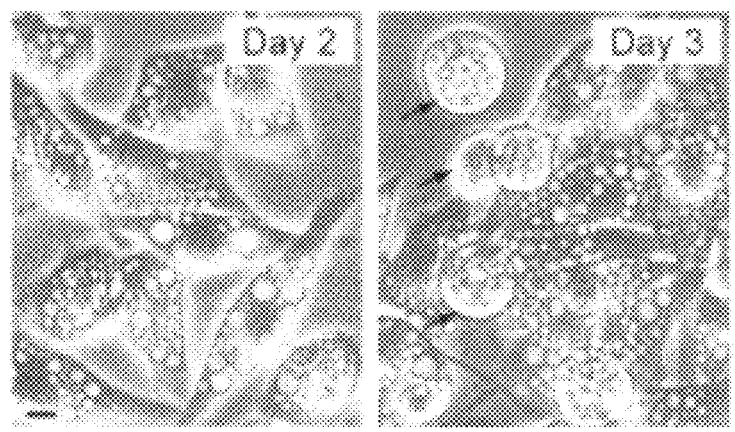
Figure 15:
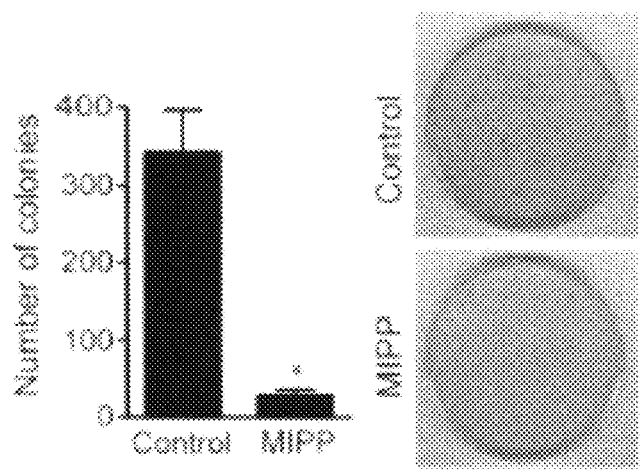

As shown in FIG. 12, both of the vacuole-inducing compounds, MIPP and Compound I, caused a marked decrease in the relative cell viability, measured by MTT assay, during the first two days of treatment. In contrast, the structurally related compounds III and IV that did not cause cellular vacuolization (FIG. 1) had little effect on cell growth/viability during the same period (FIG. 12). By the second day after addition of MIPP, the cells exhibited a significant decrease in ATP, indicative of metabolic compromise (FIG. 13). Further, there was a substantial increase in the number of rounded and detached cells in the MIPP-treated cultures between days 2 and 3 as shown in FIG. 14. Cells that had been treated with 10 µM MIPP for 2 days were non-viable in colony-forming assays, as shown in FIG. 15.

Figure 16:
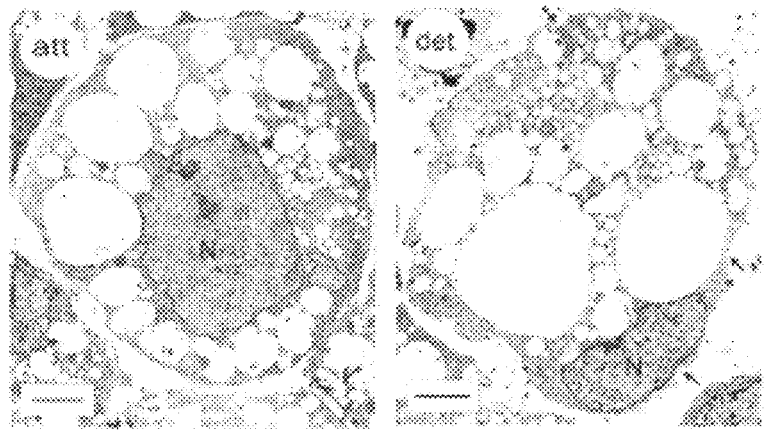
Figure 17:
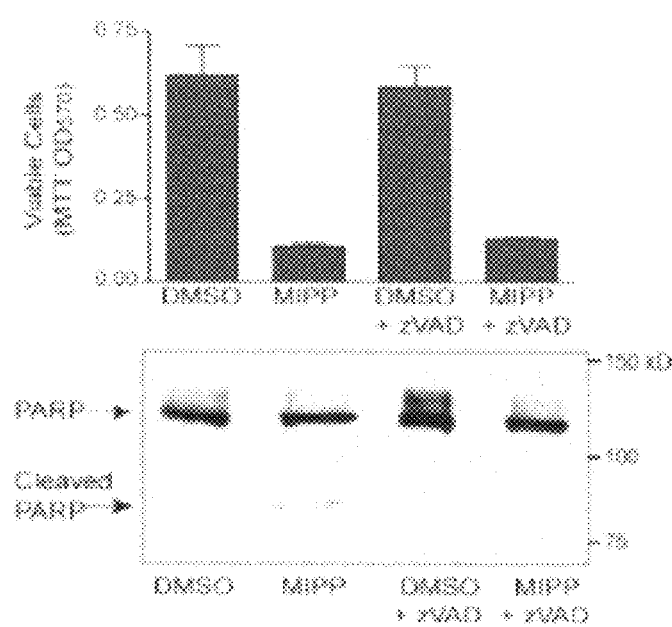

Further evaluation of the MIPP-treated cells by electron microscopy revealed that both the attached and detached cells contained numerous large, mostly empty, vacuoles bounded by a single membrane (FIG. 16). These structures were indistinguishable morphologically from the vacuoles induced by activated Ras. In the detached cells, the vacuoles had expanded to the point where they displaced much of the cytoplasmic volume and, in many cases, the plasma membrane was disrupted (FIG. 16, arrows). Even in highly vacuolated cells that were on the verge of lysis, the nuclear chromatin remained diffuse and the nuclear membrane was intact (FIG. 16). This was showing of a non-apoptotic death mechanism. The dying cells treated with MIPP showed caspase activation (i.e., cleavage of full-length PARP to an 82 kDa fragment). However, even though zVAD-fmk was able to block this cleavage, it did not prevent the loss of viability in the MIPP-treated cells. When combined with the lack of a morphological signature for apoptosis, this data shows that MIPP-induced cell death is independent of caspase activation and is due to physical disruption of the highly vacuolated cells.

Example 7

Figure 26:
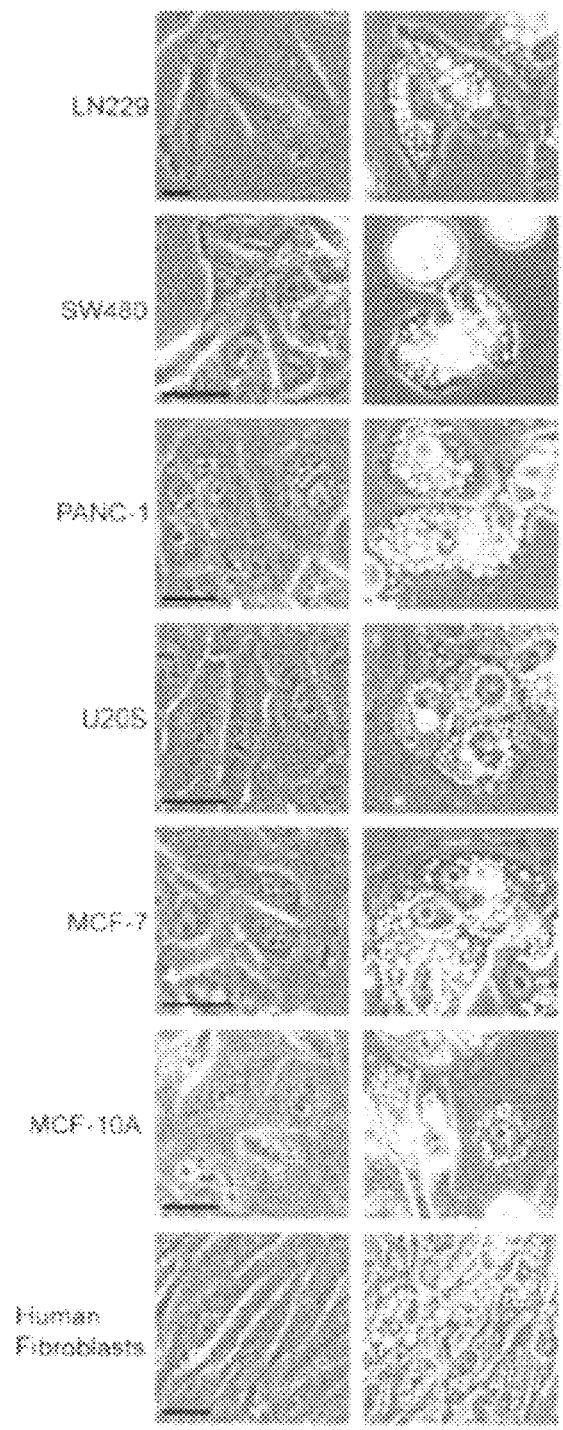
FIGS. 26-28. MIPP induces vacuoles and inhibits growth and viability in multiple human cell lines.
Figure 27:
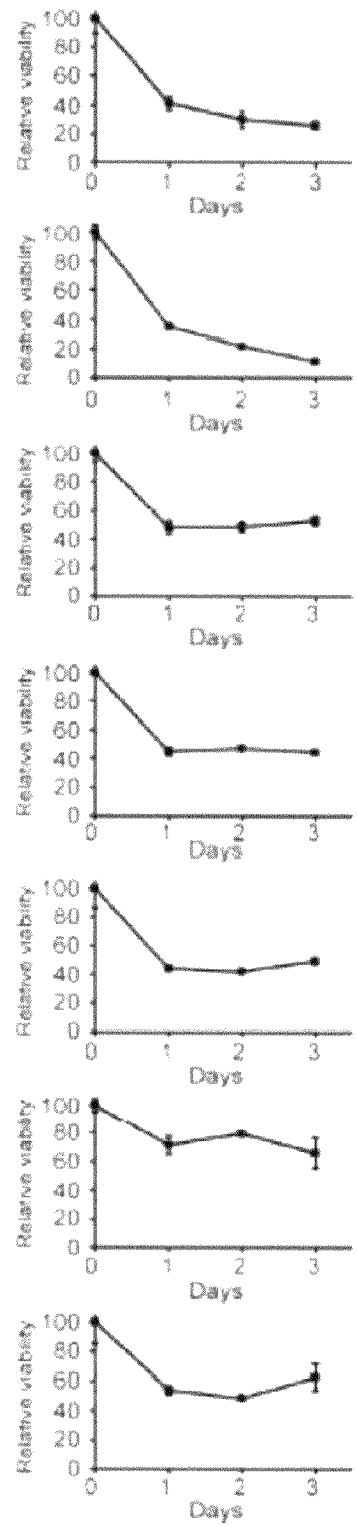
Figure 28:
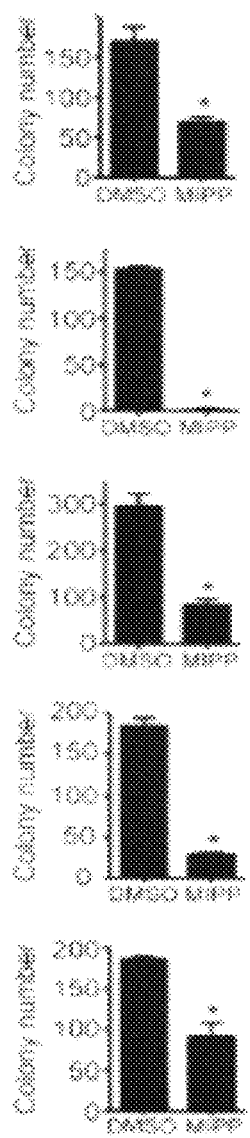

MIPP Produces Similar Effects in a Broad Spectrum of Cancer Cells, Including Drug-Resistant Glioblastoma Also disclosed herein is an analysis of the effects of the compound in several other cell lines. These include an additional glioma cell line (LN229), osteosarcoma cells (U2OS), and breast (MCF7), colon (SW480) and pancreatic (PANC-1) carcinoma cells. Similar to the results with U251 cells, 10 µM MIPP induced dramatic cytoplasmic vacuolization in all of the cell lines, as shown in FIG. 26. Although there were some differences in sensitivity, relative cell viability determined by MTT assays was generally reduced by 50-90% in all of the cancer cell lines treated with MIPP, as shown in FIG. 27. Colony forming assays confirmed that exposure to MIPP for 2 days significantly reduced long-term cell survival in all cases, as shown in FIG. 28.

Further disclosed herein is an examination of the effects of MIPP on normal human skin fibroblasts and an established mammary epithelial cell line (MCF-10A). Although these cell lines also underwent extensive cytoplasmic vacuolization, the reductions in cell viability (30% for MCF-10A and 40% for fibroblasts) were more moderate than what the inventors observed for the cancer cell lines, as shown in FIG. 27.

Figure 18:
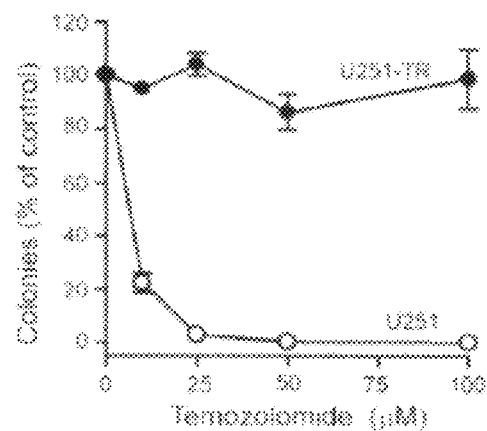
FIGS. 18-21. MIPP has similar effects on cell morphology and viability in temozolomide-resistant (U251-TR) and parental (U251) glioblastoma cells.
Figure 19:
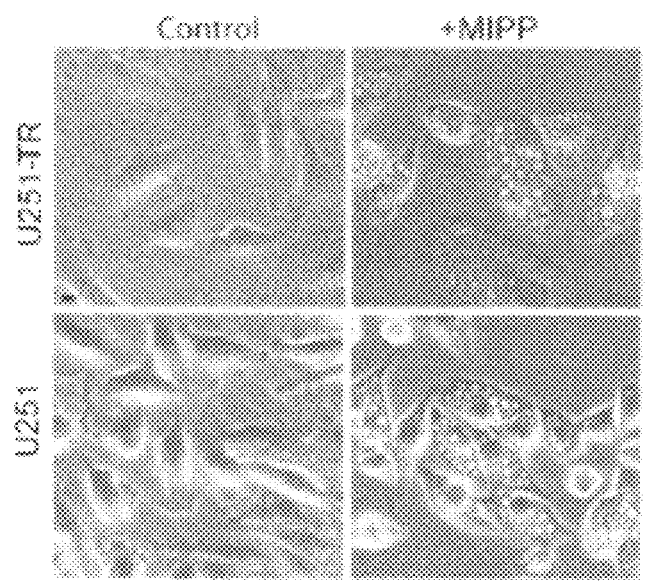

Further disclosed herein are derived temozolomide-resistant clones from the U251 glioblastoma cell line. The survival study depicted in FIG. 18 shows an example of one such clone (U251-TR), which was highly resistant to temozolomide in comparison to the parental U251 cell line. When U251-TR cells were treated with 10 µM MIPP, they underwent extensive vacuolization identical to that observed in the parental U251 cells, as shown in FIG. 19. MTT dose-response curves showed that both the parental and temozolomide-resistant cells were sensitive to MIPP over a 2-day period (FIG. 20), although the $IC_{50}$ value for the resistant cells (6.0 µM) was higher than for the parental cells (3.5 µM). As in the case of the parental U251 cells (FIG. 15), treatment of the U251-TR cells resulted in a significant decline in survival, assessed by colony forming assays (FIG. 21). Similar results were obtained with additional temozolomide-resistant clones (not shown).

Example 8

Comparisons of MIPP and MOMIPP

The foregoing SAR studies identified compound 19 as the most potent in the series for inducing methuosis. Hereinafter this new lead compound is referred to as MOMIPP; 3-(5-methoxy, 2-methyl-1H-indol-3-yl)-1-(4-pyridinyl)-2-propen-1-one. Enhanced activity of MOMIPP versus MIPP was confirmed in studies with U251 glioblastoma cells, using MTT viability assays, cell growth assays, morphological assessment, and colony forming assays to compare the two compounds. FIG. 37D shows the dose-response curves for the effects of the two drugs on cell viability.

Each compound was added at the designated concentration for two days, with medium and compound replenished after the first day. The $IC_{50}$ for MOMIPP was 1.9 µM, versus 4.8 µM for MIPP. To obtain a measure of the relative stability and duration of the effects of each compound, their effects on cell growth and survival was tested by counting the number of cells in parallel cultures treated for three days with 2.5 µM, 5 µM, or 10 µM compound, as shown in FIG. 38. Unlike the viability studies in FIGS. 36, 37D and 48, in this instance each compound was added at the beginning of the experiment and the medium was not replenished for the duration. Under these conditions, MOMIPP was clearly more effective than MIPP in reducing cell growth. The reduction of cell number in the cultures treated with MOMIPP coincided with massive early vacuolization of the cells and loss of nonviable cells from the substratum (FIG. 39). In contrast, the cells treated with MIPP initially underwent vacuolization on days 1 and 2, but tended to recover, especially at the lower concentrations of the compound (FIG. 39).

The data from these studies demonstrate that MOMIPP has a much more sustained effect than MIPP on cell morphology and cell viability. Further, dose-response comparisons of MIPP versus MOMIPP using colony forming assays was performed to assess effects on long-term cell survival. As shown in FIG. 40, both MIPP and MOMIPP reduced colony formation of U251 glioblastoma cells when the cells were treated for 2 days, although MOMIPP was much more potent than MIPP. Both compounds also reduced colony formation when cells were treated for only 4 hours, although higher concentrations of compound were required. Again, MOMIPP was more effective than MIPP (FIG. 40).

Example 9

MOMIPP Kills Drug Resistant Glioblastoma Cells

Figure 20:
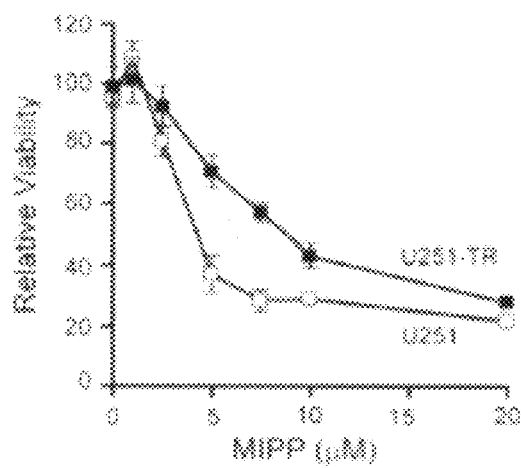
Figure 21:
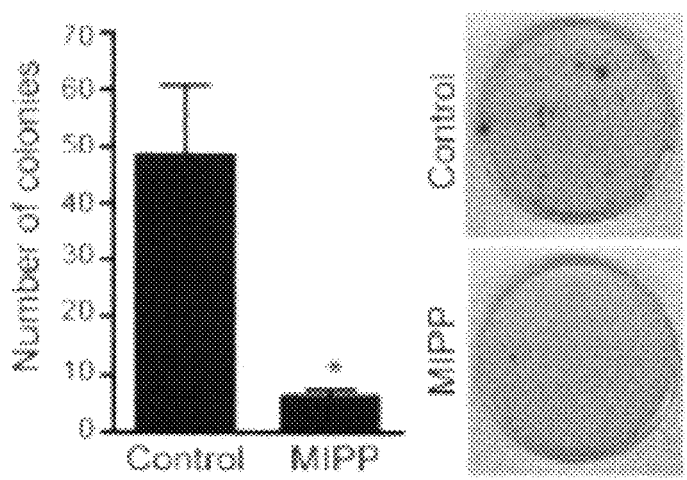

Further disclosed herein is data showing that MIPP can effectively induce methuosis and kill temozolomide-resistant U251 glioblastoma cells (FIGS. 19-21). MOMIPP can induce methuosis and reduce the viability of temozolomide-resistant glioblastoma cells (FIGS. 41A-41B) and doxorubicin-resistant breast cancer cells (FIGS. 41C, 41D, 45 and 46). MOMIPP and structurally-related compounds are shown to be useful therapeutic agents for inducing non-apoptotic cell death (i.e., methuosis) in drug-resistant glioblastoma cells.

Example 10

MOMIPP Kills a Broad Spectrum of Glioblastoma Cells, Including Glioblastoma Stem Cells The ability of MOMIPP to induce methuosis in GBM cells is not restricted to the U251 cell line. The compound induced characteristic cytoplasmic vacuolization in several additional GBM cell lines: U87MG, LN229, SF295 and T98G, as shown in FIG. 42. In all cases, 10 µM MOMIPP caused significant (p<0.005) loss of cell viability detected by MTT assay after 2 d, with no replenishment of the drug (FIG. 42). Long term survival, measured by colony forming assays, was severely attenuated in GBM cells treated with 10 µM MOMIPP for 2 d. (FIG. 43). The affected cell lines have different genetic profiles. For example, U87MG is wt for p53, while the others have mutations in p53. LN229 is wt for PTEN, while the others are null or mutant at the PTEN locus. None of the cell lines harbor Ras mutations. Thus, it is shown that the ability of MOMIPP to induce methuosis in these GBM cell lines is consistent the compound acting at the level of the endosomal trafficking machinery, independent of variations in tumor-suppressor or oncogenic signaling pathways. GMB6 was chosen because it retains amplification of EGFRvIII and exhibits invasive behavior in vivo. The acute response of GBM6 to MOMIPP was the same as the established cell lines, as shown in FIG. 42, and colony formation was strongly inhibited (FIG. 43). Studies with CD133+ stem cells isolated from xenografts of primary human GBM were carried out. When treated with MOMIPP, these cells exhibited the typical vacuolar morphology of methuosis, with reduced viability after 2 d (FIG. 42). When CD133+ stem cells isolated directly from a primary GBM specimen were treated with MOMIPP, the compound significantly inhibited colony formation at concentrations as low as 2.5 μM (FIG. 44).

Example 11

MOMIPP Kills Drug Resistant Breast Cancer Cells

Figure 45:
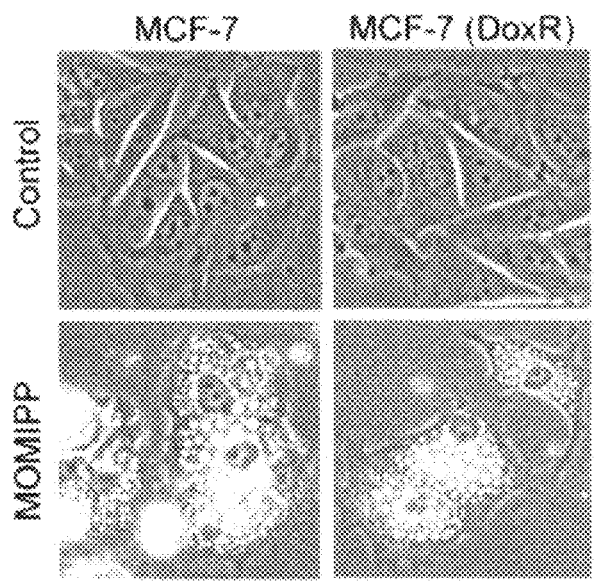
FIG. 45. Effects of MOMIPP on the morphology of wild-type MCF-7 and doxorubicin-resistant (MCF-7$_{DOX}$) mammary carcinoma cells.
Figure 46:
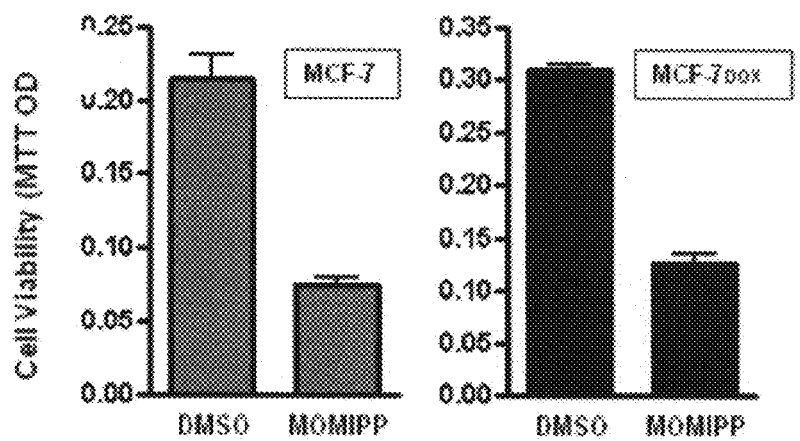
FIG. 46. Effects of MOMIPP on the short-term viability of wild-type MCF-7 and doxorubicin-resistant (MCF-7$_{DOX}$) mammary carcinoma cells.
Figure 47:
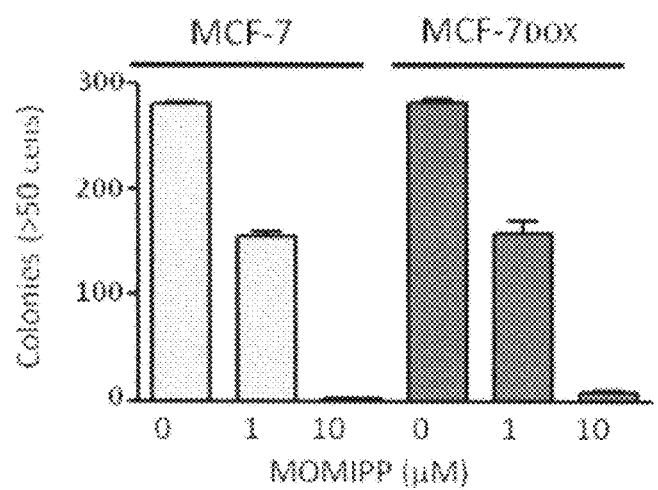
FIG. 47. Effects of MOMIPP on the colony-forming ability of wild-type MCF-7 and doxorubicin-resistant (MCF-7$_{DOX}$) mammary carcinoma cells.

MOMIPP can induce methuosis and reduce the viability of doxorubicin-resistant breast cancer cells, as is shown by severe cytoplasmic vacuolization in FIG. 45, reduced metabolic viability in FIG. 46 and decreased ability to form colonies in FIG. 47. Sensitivity of the drug resistant breast cancer cells to MOMIPP was comparable to the parental MCF7 cell line. MOMIPP and structurally-related compounds are shown to be useful therapeutic agents for inducing non-apoptotic cell death (i.e., methuosis) in drug-resistant breast cancer cells.

Example 12

MOMIPP Synthesis

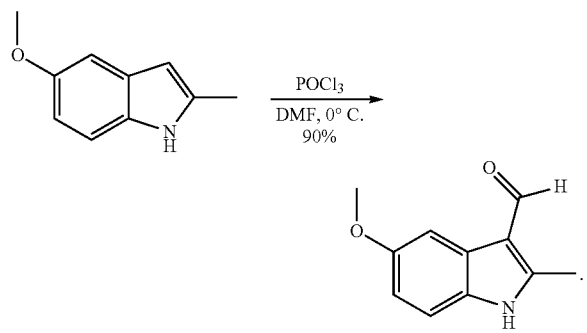

5-Methoxy-2-methyl-1H-Indole-3-carboxaldehyde

To an oven dried 25 mL round bottom flask kept under a nitrogen atmosphere and maintained at 0° C., 0.069 mL (0.744 mmol, 1.2 equiv.) of phosphorous oxychloride (POCl$_3$) was added to 0.25 mL dimethylformamide (DMF). After stirring for ten minutes, 100 mg of 5-methoxy-2-methyl-indole (0.620 mmol, 1.0 equiv.) dissolved in 0.75 mL DMF was added dropwise. After 45 minutes of stirring at 0° C., 1N NaOH was added (5 mL), forming a white precipitate which was extracted with ethyl acetate (3×10 mL). The extracts were washed with brine, dried with Na$_2$SO$_4$, filtered, concentrated, and dried under vacuum, affording 105 mg of white solid (90%). $^1$H NMR (600 MHz, d$_6$-DMSO): δ 11.875 (s, 1H), 10.009 (s, 1H), 7.570-7.566 (d, J=2.4, 1H), 7.282-7.268 (d, J=8.4, 1H), 6.797-6.778 (dd, J$_1$=9.0, J$_2$=2.4, 1H), 3.764 (s, 3H), 2.646 (s, 3H). $^{13}$C NMR (150 MHz, d$_6$-DMSO): δ 184.1, 155.5, 148.6, 130.0, 126.4, 113.7, 112.1, 111.8, 102.3, 55.3, 11.6. Melting point: 187-193° C. TLC (in 4:1 ethyl acetate:hexanes) R$_f$=0.37. Elemental analysis calculated for C$_{11}$H$_{11}$NO$_2$: C, 69.83; H, 5.86; N, 7.40. found: C, 69.95; H, 5.95; N, 7.25.

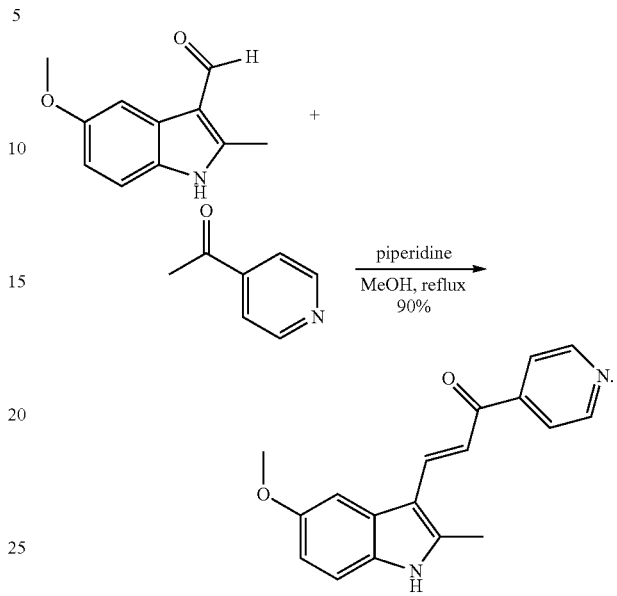

MOMIPP, trans-3-(5-Methoxy-2-methyl-1H-indol-3-yl)-1-(4-pyridinyl)-2-propen-1-one To an oven dried 25 mL round bottom flask kept under a nitrogen atmosphere, 80 mg of 5-methoxy-2-methyl-1H-Indole-3-carboxaldehyde (0.42 mmol, 1.0 equiv.) was added, followed by 2 mL anhydrous methanol, 59 μL of 4-acetylpyridine (0.53 mmol, 1.25 equiv.) and 47 μL of piperidine (0.46 mmol, 1.1 equiv.) and refluxed for 16 hours. Upon cooling the reaction to room temperature, an orange precipitate formed, which was filtered under vacuum and washed with cold methanol. The orange solid was dried under vacuum, yielding 110 mg (90%) of an orange solid. $^1$H NMR (600 MHz, d$_6$-DMSO): δ 11.909 (s, 1H), 8.812-8.802 (dd, J=4.2, J$_2$=1.8, 2H), 8.097-8.072 (d, J=15, 1H), 7.947-7.937 (dd, J=4.2, J$_2$=1.8, 2H), 7.434-7.430 (d, J=2.4, 1H), 7.374-7.349 (d, J=15, 1H), 7.315-7.304 (d, J=8.4, 1H), 6.851-6.833 (dd, J$_1$=8.4, J2=2.4, 1H), 3.860 (s, 3H), 2.572 (s, 3H). $^{13}$C NMR (150 MHz, d$_6$-DMSO): δ 188.0, 155.2, 150.6, 145.8, 145.1, 136.6, 131.0, 126.6, 121.4, 112.8, 112.3, 110.9, 109.3, 103.5, 55.6, 12.2. Melting point: 255-257° C. TLC (in 4:1 ethyl acetate:hexanes) R$_F$=0.16. Elemental analysis calculated for C$_{18}$H$_{16}$N$_2$O$_2$: C, 73.95; H, 5.52; N, 9.58. found: C, 73.76; H, 5.46; N, 9.47.

Example 13

Structure Activity Relationship Compound Synthesis

2-Methylindole-3-carboxaldehyde (compound 2a)

To a dried 300 mL two-neck round bottom flask under argon at 0° C., N,N-dimethylformamide (3 mL) was added, followed by POCl3 (1.05 mL, 11.3 mmol). After stirring for ten minutes, 2-methylindole (1.23 g, 9.37 mmol) dissolved in DMF (6 mL) was added dropwise via an addition funnel under argon. After two hours, 1N NaOH (70 mL) was added slowly, upon which a white precipitate formed. The solid was filtered and dried under vacuum, yielding 1.32 g (89%) of white solid. $^1$H NMR (600 MHz, d6-DMSO): δ 11.998 (s, 1H, N—H), 10.050 (s, 1H, CHO), 8.044-8.032 (d, J=7.2, 1H, indole-4H), 7.388-7.375 (d, J=7.8, 1H, indole-7H), 7.183-7.135 (m, 2H, indole-5,6H), 2.679 (s, 3H, methyl). 13CNMR (150 MHz, d6-DMSO): δ 184.3, 148.6, 135.4, 125.6, 122.7, 121.9, 120.0, 113.7, 111.4, 11.5. Melting Point: 195-200° C. TLC (ethyl acetate:hexanes 4:1) Rf=0.39. Elemental analysis calculated for C10H9NO: C, 75.45; H, 5.70; N, 8.80. found: C, 75.23; H, 5.70; N, 8.93.

trans-3-(2-Methyl-1H-indol-3-yl)-1-(4-pyridinyl)-2-propen-1-one (compound 2)

To a dried 500 mL round bottom flask under argon, 2-methylindole-3-carboxaldehyde (400 mg, 2.51 mmol) was dissolved in anhydrous MeOH (10 mL). 4-Acetyl-pyridine (305 μL, 2.76 mmol, 1.1 equiv.) and piperidine (82 μL, 0.83 mmol) were added and the reaction was stirred under reflux. A red-orange precipitate gradually formed, and after twelve hours this solid was isolated by filtration, rinsed with chilled methanol and dried under vacuum, producing 458 mg (69%) of yellow solid. NMR: 1H NMR (600 MHz, d6-DMSO): δ 12.017 (s, 1H, N—H), 8.816-8.806 (dd, J1=4.5, J2=2.1, 2H, pyr-2,6H), 8.121-8.095 (d, J=15.6, 1H, C=CH), 8.077-8.063 (m, 1H, indole-4H), 7.975-7.965 (dd, J1=4.5, J2=1.5, 2H, pyr-3,5H), 7.489-7.464 (d, J=15.6, 1H, C=CH), 7.415-7.400 (m, 1H, indole-7H), 7.220-7.200 (m, 2H, indole-5,6H), 2.596 (s, 3H, methyl). 13C NMR (150 MHz, d6-DMSO): δ 188.0, 150.7, 145.6, 144.9, 139.5, 136.3, 125.8, 122.4, 121.50, 121.46, 120.4, 113.1, 111.7, 109.4, 11.9. Melting Point: 268-272° C. TLC (ethyl acetate:hexanes 4:1) Rf=0.18. Elemental analysis calculated for C17H14N2O: C, 77.84; H, 5.38; N, 10.68. found: C, 77.96; H, 5.28; N, 10.59.

trans-3-(1H-Indol-3-yl)-1-phenyl-2-propen-1-one (compound 9)

In a dried, 25 mL round bottom flask under argon, indole-3-carboxaldehyde (300 mg, 2.07 mmol) was dissolved in anhydrous methanol (8 mL). Acetophenone (240 μL, 2.07 mmol) and piperidine (100 μL, 1.00 mmol) was added. The reaction was stirred under reflux for 18 hours. 10% Acetic acid was added (10 mL), precipitating 248 mg of a crude yellow solid. This was recrystallized in 100% EtOH, filtered, and dried under vacuum, yielding a pure, yellow solid (198 mg, 39%, 247.29 MW). 1H NMR (600 MHz, d6-DMSO): δ 8.133-8.114 (m, 3H, phenyl-2,6H, indole-2H), 8.095-8.081 (m, 1H, indole-4H), 8.075-8.049 (d, J=15.6, 1H, C=CH), 7.668-7.642 (d, J=15.6, 1H, C=CH), 7.655-7.629 (m, 1H, phenyl-4H), 7.581-7.556 (t, J=1.5, 2H, phenyl-3,5H), 7.504-7.490 (m, 1H, indole-7H), 7.254-7.231 (m, 2H, indole-5,6H). $^{13}$C NMR (150 MHz, d6-DMSO): δ 188.8, 139.1, 138.5, 137.5, 133.4, 132.4, 128.7, 128.2, 125.1, 122.8, 121.2, 120.4, 115.3, 112.8, 112.5. Melting point: 167-170° C. TLC (in 2:1 ethyl acetate:hexanes) Rf=0.48. Elemental analysis calculated for C17H13NO: C, 82.57; H, 5.30; N, 5.66. found: C, 82.19; H, 5.35; N, 5.63.

trans-3-(1H-Indol-3-yl)-1-(2-pyridinyl)-2-propen-1-one (compound 10)

Indole-3-carboxaldehyde (200 mg, 1.38 mmol) was added to a dried 100 mL round bottom flask under argon and anhydrous methanol (8 mL) was added. 2-Acetyl-pyridine (232 μL, 2.07 mmol) and piperidine (69 μL, 0.7 mmol) were added and the reaction was stirred under reflux for 24 hours, after which still no precipitate had formed (AcOH did not lead to precipitation). The crude reaction mixture was concentrated and directly applied to a silica column for chromatography (ethyl acetate:hexanes 1:1). The product was partially separated from the aldehyde starting material (some product coeluted with aldehyde and was discarded), and 80 mg (23%) of purified product was isolated. NMR: 1H NMR (600 MHz, d6-DMSO): δ 11.989 (s, 1H, N—H), 8.831-8.819 (m, pyr-H2), 8.220-8.194 (d, J=15.6, 1H, C=CH), 8.154-8.105 (m, 3H, C=CH, indole-H2, pyr-H3), 8.052-8.027 (m, 1H, pyr-H4), 7.976-7.962 (m, 1H, indole-H4), 7.679-7.656 (m, 1H, pyr-H5), 7.522-7.508 (m, 1H, indole-H7), 7.285-7.262 (m, 2H, indole-H5,6). 13C NMR (150 MHz, d6-DMSO): δ 188.2, 154.3, 149.1, 139.3, 137.7, 137.6, 134.2, 127.1, 125.1, 122.3, 122.2, 121.4, 120.1, 114.3, 113.1, 112.7. Melting Point: 141-145° C. TLC: (ethyl acetate:hexanes 4:1) Rf=0.40. Elemental analysis calculated for C16H12N2O.0.1C4H8O2: C, 76.62; H, 5.02; N, 10.90. found: C, 76.41; H, 5.03; N, 10.80.

trans-3-(1H-Indol-3-yl)-1-(3-pyridinyl)-2-propen-1-one (compound 11)

Indole-3-carboxaldehyde (100 mg, 0.69 mmol) was added to a dried 100 mL round bottom flask and dissolved in anhydrous methanol (5 mL). 3-Acetyl-pyridine (113 μL, 1.03 mmol, 1.5 equiv.) and piperidine (69 μL, 0.7 mmol) were added and the reaction stirred under reflux. After twelve hours, the reaction was cooled to room temperature, upon which a precipitate formed. The solid was filtered, yielding 54 mg. However, there was significant aldehyde present on a crude NMR. This mixture was dry-loaded onto silica and purified by column chromatography (methylene chloride:methanol 9:1), producing 33 mg pure, yellow solid (19%). NMR: 1H NMR (600 MHz, d6-DMSO): δ 12.004 (s, 1H, N—H), 9.292-9.289 (d, J=1.8, 1H, pyr-H2), 8.808-8.797 (dd, J1=4.8, J2=1.8, 1H, pyr-H6), 8.467-8.447 (dt, J1=7.8, J2=2.1, 1H, pyr-H4), 8.174 (s, 1H, indole-H2), 8.154-8.140 (dd, J1=6.6, J2=1.8, 1H, indole-H4), 8.120-8.095 (d, J=15.0, 1H, C=CH), 7.665-7.639 (d, J=15.6, 1H, C=CH), 7.607-7.585 (m, 1H, pyr-H5), 7.506-7.492 (dd, J1=6.9, J2=1.5, 1H, indole-H7), 7.268-7.223 (qd, J1=6.6, J2=1.5, 1H, indole-H5, 6). 13C NMR (150 MHz, d6-DMSO): δ 187.9, 152.7, 149.3, 139.9, 137.6, 135.7, 134.1, 133.7, 125.1, 123.9, 122.9, 121.3, 120.7, 115.0, 112.9, 112.5. Melting Point: 192-194° C. TLC (methylene chloride:methanol 9:1) Rf=0.26. Elemental analysis calculated for C16H12N2O: C, 77.40; H, 4.87; N, 11.28. found: C, 77.00; H, 4.80; N, 11.12.

trans-3-(1H-Indol-3-yl)-1-(4-pyridinyl)-2-propen-1-one (compound 12)

In a dried, 25 mL round bottom flask under argon, indole-3-carboxaldehyde (300 mg, 2.07 mmol) was dissolved in anhydrous methanol (8 mL). 4-Acetyl-pyridine (229 μL, 2.07 mmol) and piperidine (100 μL, 1.00 mmol) were added. The reaction was stirred under reflux; gradually, yellow product recipitated during the reaction. After 14 hours, the reaction was cooled to room temperature, filtered and washed with chilled methanol and hexanes. Drying under vacuum for two hours yielded a pure, yellow solid (343 mg, 67%). 1H NMR (600 MHz, d6-DMSO): δ 8.826-8.816 (dd, J1=4.2, J2=1.8, 2H, pyr-H2,6), 8.186-8.182 (d, J=2.4, 1H, indole-H2), 8.128-8.117 (m, 1H, indole-H4), 8.121-8.095 (d, J=15.6, 1H, C=CH), 7.978-7.968 (dd, J1=4.2, J2=1.8, 2H, pyr-H3,5), 7.592-7.566 (d, J=15.6, 1H, C=CH), 7.512-7.498 (m, 1H, indole-H7), 7.267-7.243 (m, 2H, indole H-5,6). 13C NMR (150 MHz, d6-DMSO): δ 188.4, 150.7, 144.7, 140.9, 137.6, 134.6, 125.0, 123.0, 121.5, 121.4, 120.6, 114.6, 112.9, 112.6. Melting point: 266-268'C. TLC (in 4:1 ethyl acetate:hexanes) Rf=0.23. Elemental analysis calculated for C16H12N2O: C, 77.40; H, 4.87; N, 11.28. found: C, 77.35; H, 4.84; N, 11.23.

trans-3-(5-Methoxy-1H-indol-3-yl)-1-(4-pyridinyl)-2-propen-1-one (compound 13)

In a dried, 25 mL round bottom flask under argon, 5-methoxyindole-3-carboxaldehyde (100 mg, 0.57 mmol) was dissolved in anhydrous methanol (3 mL). 4-Acetyl-pyridine (63 µL, 0.57 mmol) and piperidine (30 µL, 0.3 mmol) were added. The reaction was stirred under reflux, during which a crude yellow solid precipitated. After 15 hours, 10% acetic acid (10 mL) was added to further the precipitation. The solid was filtered and dried under vacuum, yielding a pure, yellow solid (121 mg, 76%). 1H NMR (600 MHz, d6-DMSO): δ 8.821-8.811 (dd, J1=4.5, J2=1.5, 2H, pyr-H2,6), 8.163-8.159 (d, J=2.4, 1H, indole-H2), 8.117-8.091 (d, J=15.6, 1H, C=CH), 7.953-7.943 (dd, J1=4.5, J2=1.5, 2H, pyr-H3,5), 7.532-7.506 (d, J=15.6, 1H, C=CH), 7.489-7.485 (d, J=2.4, 1H, indole-H4), 7.405-7.391 (d, J=8.4, 1H, indole-H7), 6.902-6.883 (dd, J1=9.0, J2=2.4, 1H, indole-H6), 3.866 (s, 3H, methyl). 13C NMR (150 MHz, d6-DMSO): δ 188.4, 155.2, 150.7, 144.9, 140.9, 134.2, 132.4, 126.0, 121.5, 114.3, 113.3, 112.7, 112.4, 102.4, 55.6. Melting point: 235-237° C. TLC (in 4:1 ethyl acetate:hexanes) Rf=0.20. Elemental analysis calculated for C17H14N2O2: C, 73.37; H, 5.07; N, 10.07. found: C, 73.55; H, 5.00; N, 10.04.

trans-3-(5-Phenylmethoxy-1H-indol-3-yl)-1-(4-pyridinyl)-2-propen-1-one (compound 14)

In a dried, 25 mL round bottom flask under argon, 5-benzyloxyindole-3-carboxaldehyde (100 mg, 0.40 mmol) was dissolved in anhydrous methanol (3 mL). 4-Acetyl-pyridine (75 µL, 0.68 mmol) and piperidine (20 µL, 0.2 mmol) were added. The reaction was stirred under reflux, during which a crude yellow solid precipitated. The solid was filtered, rinsed with cold methanol and dried under vacuum. This crude product (107 mg) was purified from residual aldehyde by column chromatography in ethyl acetate:hexanes (1:1-3:1 gradient), yielding pure, yellow solid (70 mg, 49%). 1H NMR (600 MHz, d6-DMSO): δ 8.837-8.827 (dd, J1=4.5, J2=1.5, 2H, pyr-2,6H), 8.148-8.143 (d, J=3.0, 1H, indole-2H), 8.095-8.069 (d, J=15.6, 1H, C=CH), 7.932-7.922 (dd, J1=4.5, J2=1.5, 2H, pyr-3,5H), 7.556-7.553 (d, J=1.8, 1H, indole-4H), 7.523-7.511 (d, J=7.2, 2H, phenyl-2,6H), 7.460-7.434 (d, J=15.6, 1H, C=CH), 7.411-7.370 (m, 3H, phenyl-3,5H, indole-7H), 7.330-7.306 (t, J=7.2, 1H, phenyl-4H), 6.979-6.961 (dd, J1=8.4, J2=2.4, 1H, indole-6H), 5.252 (s, 2H, methylene). 13C NMR (150 MHz, d6-DMSO): 188.4, 154.1, 150.7, 144.9, 140.9, 137.7, 134.6, 132.5, 128.4, 127.7, 127.6, 125.8, 121.5, 114.2, 113.3, 113.1, 112.7, 104.1, 69.8. Melting point: 218-221° C. TLC (in 4:1 ethyl acetate:hexanes) Rf=0.26. Elemental analysis calculated (for C23H19N2O2.0.2 C6H14.0.05 H2O): C, 78.02; H, 5.93; N, 7.52. found: C, 77.69; H, 5.62; N, 7.24.

trans-3-(5-Hydroxy-1H-Indol-3-yl)-1-(4-pyridinyl)-2-propen-1-one (compound 15)

To a dried two-neck 250 mL round bottom flask under argon at −40° C., compound 13 (352 mg, 0.99 mmol) was partially dissolved in CH2Cl2 (30 mL). BBr3 (10 mL, 1.0 M in CH2Cl2, 10 mmol) was added dropwise via an addition funnel under argon. After four hours the reaction was poured onto ice and treated with 5 N NaOH until pH≈12. The aqueous solution was isolated and treated with 5 N HCl until pH 7, forming a brown precipitate which was extracted with ethyl acetate (3×40 mL). Extracts were combined, dried with Na2SO4, filtered, concentrated and dried under vacuum to yield 158 mg of an orange solid (61%). NMR: 1H NMR (600 MHz, d6-DMSO): 11.840 (s, 1H, N—H), 9.109 (s, 1H, O—H), 8.826-8.816 (dd, J1=4.5, J2=1.5, 2H, pyr-2,6H), 8.063-8.058 (d, J=3.0, 1H, indole-2H), 8.048-8.022 (d, J=15.6, 1H, C=CH), 7.902-7.892 (dd, J1=4.5, J2=1.5, 2H, pyr-3,5H), 7.349-7.346 (d, J=1.8, 1H, indole-4H), 7.307-7.293 (d, J=8.4, 1H, indole-H7), 6.762-6.744 (dd, J1=8.4, J2=2.4, 1H, indole-H6). 13C NMR (150 MHz, d6-DMSO): 188.2, 152.9, 150.6, 145.0, 141.4, 134.8, 131.7, 126.0, 121.3, 113.6, 113.1, 112.7, 112.3, 104.9. Melting Point: 262-268° C. TLC (in ethyl acetate:hexane 4:1) Rf=0.35. Elemental analysis calculated for C16H12N2O2.0.1H2O: C, 72.22; H, 4.62; N, 10.53. found: C, 72.21; H, 4.42; N, 10.26.

trans-3-(5-Methoxy-1H-indol-3-yl)-1-(3-pyridinyl)-2-propen-1-one (compound 16)

In a dried, 50 mL round bottom flask under argon, 5-methoxyindole-3-carboxaldehyde (100 mg, 0.57 mmol) was dissolved in anhydrous methanol (4 mL). 3-Acetyl-pyridine 63 µL, 0.57 mmol) and piperidine (30 µL, 0.30 mmol) were added. The reaction was stirred under reflux, during which a crude orange solid precipitated. After twenty hours, the solid was isolated by vacuum filtration, rinsed with chilled methanol and dried under vacuum, yielding a pure, orange solid (98 mg, 60%). 1H NMR (600 MHz, d6-DMSO): δ 11.891 (s, 1H, N—H), 9.276-9.273 (d, J=1.8, 1H, pyr-2H), 8.798-8.790 (m, 1H, pyr-6H), 8.440-8.421 (m, 1H, pyr-4H), 8.155-8.150 (d, J=3.0, 1H, indole-2H), 8.113-8.088 (d, J=15.0, 1H, C=CH), 7.607-7.582 (d, J=15.0, 1H, C=CH), 7.598-7.584 (m, 1H, pyr-5H), 7.500-7.497 (d, J=1.8, 1H, indole-4H), 7.397-7.383 (d, J=8.4, 1H, indole-7H), 6.892-6.874 (dd, J1=8.4, J2=2.4, 1H, indole-6H), 3.867 (s, 3H, methyl). 13C NMR (150 MHz, d6-DMSO): δ 187.9, 155.1, 152.6, 149.3, 139.9, 135.7, 133.8, 133.7, 132.3, 126.1, 123.9, 114.7, 113.2, 112.7, 112.4, 102.6, 55.6. Melting point: 169-173° C. TLC (in 4:1 ethyl acetate:hexanes) Rf=0.17. Elemental analysis calculated C17H14N2O2: C, 73.37; H, 5.07; N, 10.07. found: C, 73.09; H, 5.10; N, 10.01.

trans-3-(5-Methoxy-1H-indol-3-yl)-1-(pyrazine)-2-propen-1-one (compound 17)

In a dried, 25 mL round bottom flask under argon, 5-methoxyindole-3-carboxaldehyde (75 mg, 0.43 mmol) was dissolved in anhydrous methanol (4 mL). Acetyl-pyrazine (52 mg, 0.43 mmol) and piperidine (23 µL, 0.23 mmol) were added. The reaction was stirred under reflux, during which a crude, yellow solid precipitated. After three hours, the solid was isolated by vacuum filtration, rinsed with chilled methanol and dried under vacuum. This crude product was recrystallized in EtOH (8 mL) to remove residual aldehyde, yielding a pure, yellow solid (28 mg, 24%). 1H NMR (600 MHz, d6-DMSO): δ 11.960 (s, 1H, N—H), 9.244 (s, 1H, pyr-2H), 8.905-8.873 (m, 2H, pyr-4,5H), 8.204-8.178 (d, J=15.6, 1H, C=CH), 8.155 (s, 1H, indole-2H), 7.987-7.961 (d, J=15.6, 1H, C=CH), 7.427-7.412 (m, 2H, indole-4,7H), 6.934-6.915 (dd, J1=9.0, J2=2.4, 1H, indole-6H), 3.853 (s, 3H, methyl). 13C NMR (150 MHz, d6-DMSO): δ 187.3, 155.1, 148.8, 147.6, 144.0, 143.7, 140.2, 134.6, 132.5, 126.0, 113.4, 113.2, 112.8, 111.9, 102.9, 55.6. Melting point: 176-180° C. TLC (in 4:1 ethyl acetate:hexanes) Rf=0.30. Elemental analysis calculated C16H13N3O2: C, 68.81; H, 4.69; N, 15.05. found: 68.76; H, 4.64; N, 14.99.

5-Methoxy-2-methyl-1H-indole-3-carboxaldehyde (compound 18)

To a dried two-neck 25 mL round bottom flask at 0° C., POCl3 (1.00 mL, 10.8 mmol) was added to N,N-dimethylformamide (2.5 mL). After ten minutes of stirring, 2-methyl-5-methoxyindole (1.45 mg, 9.00 mmol) dissolved in DMF (5 mL) was added dropwise. After 45 minutes, 1N NaOH (50 mL) was slowly added, forming a white precipitate. The solid was isolated by filtration, washed with cold H2O and dried under vacuum, yielding 1.52 g of white solid (90%). 1H NMR (600 MHz, d6-DMSO): δ 11.875 (s, 1H, N—H), 10.009 (s, 1H, CHO), 7.570-7.566 (d, J=2.4, 1H, indole-4H), 7.282-7.268 (d, J=8.4, 1H, indole-7H), 6.797-6.778 (dd, J1=9.0, J2=2.4, 1H, indole-6H), 3.764 (s, 3H, o-methyl), 2.646 (s, 3H, c-methyl). 13C NMR (150 MHz, d6-DMSO): δ 184.1, 155.5, 148.6, 130.0, 126.4, 113.7, 112.1, 111.8, 102.3, 55.2, 11.5. Melting Point: 188-192° C. TLC (ethyl acetate:hexane 4:1) Rf=0.37. Elemental analysis calculated for C11H11NO2: C, 69.83; H, 5.86; N, 7.40. found: C, 69.65; H, 5.95; N, 7.25.

trans-3-(5-Methoxy-2-methyl-1H-indol-3-yl)-1-(4-pyridinyl)-2-propen-1-one (compound 19)

To a dried 250 mL two-neck round bottom flask under argon, 2-methyl-5-methoxy-1H-indole-3-carboxaldehyde (1.51 g, 7.98 mmol) was dissolved in anhydrous MeOH (30 mL). 4-Acetylpyridine (1.32 mL, 11.97 mmol, 1.5 equiv.) and piperidine (0.788 mL, 7.98 mmol) were added and the reaction was stirred under reflux. An orange solid gradually precipitated, and this was isolated by filtration, rinsed with chilled MeOH and dried under vacuum, yielding 2.08 g of orange solid (89%). 1H NMR (600 MHz, d6-DMSO): δ 11.909 (s, 1H, N—H), 8.812-8.802 (dd, J1=4.2, J2=1.8, 2H, pyr-2,6H), 8.097-8.072 (d, J=15.0, 1H, C=CH), 7.947-7.937 (dd, J1=4.2, J2=1.8, 2H pyr-3,5H), 7.434-7.430 (d, J=2.4, 1H, indole-4H), 7.374-7.349 (d, J=15.0, 1H, C=CH), 7.315-7.301 (d, J=8.4, 1H, indole-7H), 6.851-6.833 (dd, J1=8.4, J2=2.4, 1H, indole-6H), 3.860) (s, 3H, o-methyl), 2.572 (s, 3H, c-methyl). 13C NMR (150 MHz, d6-DMSO): δ 188.1, 155.2, 150.6, 145.8, 145.1, 136.6, 131.0, 126.6, 121.5, 112.8, 112.3, 110.9, 109.3, 103.5, 55.6, 12.2. Melting Point: 252-256° C. TLC (ethyl acetate:hexane 4:1) Rf=0.16. Elemental analysis calculated for C18H16N2O2: C, 73.95; H, 5.52; N, 9.58. found: C, 73.76; H, 5.46; N, 9.47.

trans-3-(5-Methoxy-1-methyl-Indol-3-yl)-1-(4-pyridinyl)-2-propen-1-one (compound 20)

N,Ndimethylformamide (3 mL) was added to a dried 100 mL two-neck round bottom flask under argon containing NaH (21 mg, 0.52 mmol, 60% in mineral oil, 1.2 equiv., unwashed). After stirring for five minutes, the starting material (120 mg, 0.43 mmol) dissolved in DMF (1 mL) was added slowly and stirred for five minutes until a homogenous red-solution was formed. Methyl iodide (40 µL, 0.65 mmol, 1.5 equiv.) was added slowly. After two hours, sat. NH4Cl (20 mL) and H2O (20 mL) was added; this was extracted with ethyl acetate (3×30 mL), dried with Na2SO4, filtered and concentrated. The crude product was purified by column chromatography (methylene chloride:methanol 95:5) providing 103 mg (82%) of solid. NMR: 1H NMR (400 MHz, d6-DMSO): δ 8.821-8.806 (dd, J1=4.4, J2=1.6, 2H, pyr-2, 6H), 8.143 (s, 1H, indole-2H), 8.081-8.042 (d, J=15.6, 1H, C=CH), 7.950-7.935 (dd, J1=4.4, J2=1.6, 2H, pyr-3,5H), 7.517-7.473 (m, 3H, C=CH, indole-4,7H), 6.971-6.942 (dd, J1=9.2, J2=2.4, 1H, indole-6H), 3.875 (s, 3H, o-methyl), 3.838 (s, 3H, n-methyl). 13C NMR (100 MHz, d6-DMSO): δ 188.2, 155.5, 150.6, 144.9, 140.2, 137.3, 133.1, 126.5, 121.5, 114.2, 112.3, 111.9, 111.5, 102.9, 55.7, 33.4. Melting Point: 178-182° C. TLC (in methylene chloride:methanol 95:5) Rf=0.35. Elemental analysis calculated for C18H16N2O2.0.1H2O: C, 73.50; H, 5.55; N, 9.52. found: C, 73.34; H, 5.77; N, 9.25.

trans-3-(5-Hydroxy-1H-Indol-3-yl)-1-(4-pyridinyl)-2-propen-1-one (compound 21)

In a dried 250 mL two-neck round bottom flask under argon, compound 19 (500 mg, 1.71 mmol) was partially dissolved in anhydrous CH2Cl2 (35 mL) and placed at −78° C. BBr3 (17 mL, 1.0 M in CH2Cl2, 17 mmol) was added dropwise via an addition funnel under argon. After addition, the reaction was warmed to room temperature and stirring continued for one hour. Ice-water (50 mL) was added, followed by 1N NaOH until the pH≈12 (~60 mL). The CH2Cl2 was further extracted with 1N NaOH (3×20 mL). The basic extracts were neutralized with 8N HCl to a neutral pH (~8 mL), upon which the product precipitated. The precipitate was filtered and dried under vacuum, providing 454 mg (95%) of a yellow solid. NMR: 1H NMR (600 MHz, d6-DMSO): δ 11.833 (s, 1H, N—H), 9.072 (s, 1H, O—H), 8.818 (s, 2H, pyr-2,6H), 8.064-8.039 (d, J=15.0, 1H, C=CH), 7.897 (s, 2H, pyr-3,5H), 7.342 (s, 1H, indole-4H), 7.282-7.257 (d, J=15.0, 1H, C=CH), 7.209-7.195 (d, J=8.4, 1H, indole-7H), 6.687-6.674 (d, J=7.8, 1H, indole-6H), 2.542 (s, 3H, methyl). 13C NMR (150 MHz, d6-DMSO): δ 187.7, 153.0, 150.7, 145.9, 145.4, 140.0, 130.2, 126.8, 121.3, 112.2, 112.0, 111.6, 109.1, 105.2, 12.0. Melting Point: 296-299° C. TLC (in ethyl acetate:hexane 4:1) Rf=0.19. Elemental analysis calculated for C17H14N2O2.0.1 CH2Cl2: C, 71.55; H, 4.99; N, 9.79. found: C, 71.89; H, 5.02; N, 9.67.

2-Methyl-1H-indol-5-ol (compound 22)

A dried 250 mL two-neck round bottom flask was charged with 2-methyl-5-methoxyindole (1.00 g, 6.20 mmol), purged with argon, and CH2Cl2 (30 mL) was added and stirred vigorously until the indole was dissolved. After placing the reaction at −78° C., BBr3 (37.2 mL, 1.0 M in $CH_2Cl_2$, 37.2 mmol, 6 equiv.) was added dropwise via an addition funnel under argon. After addition, the reaction was allowed to slowly warm to room temperature. Thirty minutes after removing the cooling bath, the reaction was poured into ice-water (~50 mL) and sat. NaHCO3 (50 mL), to a neutral pH. This was extracted with CH2Cl2 (3×50 mL); the aqueous phase retained a yellow color and was acidified to pH~3 (with 5N HCl) and extracted with ethyl acetate (2×50 mL). The combined organic extracts were washed with brine, dried with Na2SO4, filtered and concentrated to a brown oil. After drying under vacuum for 6 hours, 845 mg of a pure brown solid was isolated (93%, 147.17 MW). 1H NMR (600 MHz, d6-DMSO): 10.538 (s, 1H, N—H), 8.476 (s, 1H, O—H), 7.028-7.014 (d, J=8.4, 1H, indole-7H), 6.701-6.698 (d, J=1.8, 1H, indole-4H), 6.487-6.468 (dd, J1=9.0, J2=2.4, 1H, indole-6H), 5.906 (s, 1H, indole-3H), 2.305 (s, 3H, methyl). 13C NMR (150 MHz, d6-DMSO): δ 150.4, 135.8, 130.6, 129.4, 110.6, 109.8, 103.3, 98.5, 13.5. Melting point: 131-134° C. TLC (in 1:1 ethyl acetate:hexanes) Rf=0.28. Elemental analysis calculated for C9H8NO: C, 73.45; H, 6.16; N, 9.52. found: C, 73.09; H, 6.29; N, 9.28.

5-(4-Methylbenzoate)methoxy-2-methyl-1H-indole (compound 23)

In a 250 mL round bottom flask, 2-methyl-1H-indole-5-ol (670 mg, 4.55 mmol) was partially dissolved in CH2Cl2 (50 mL). Tetran-butylammonium bromide (808 mg, 2.5 mmol) was added, followed by NaOH (50 mL of a 5 N solution, 250 mmol), and methyl 4-(bromomethyl)benzoate (1.15 g, 5.01 mmol, 1.1 equiv.). After 8 hours, the organic layer was removed, and the aqueous phase was extracted with CH2Cl2 (1×30 mL). The combined extracts were washed with brine, dried with Na2SO4, filtered and concentrated to an oil. Purification by column chromatography (1:3 ethyl acetate:hexane) provided 839 mg of pure product (63%, 295.33 MW) [followed by the 3,5-doubly alkylated product (115 mg, 5%)]. 1H NMR (600 MHz, d6-DMSO): δ 10.755 (s, 1H, N—H), 7.980-7.966 (d, J=8.4, 2H, phenyl-3,5H), 7.602-7.588 (d, J=8.4, 2H, phenyl-2,6H), 7.150-7.136 (d, J=8.4, 1H, indole-7H), 6.982-6.978 (d, J=2.4, 1H, indole-4H) 6.717-6.699 (dd, J1=8.4, J2=2.4, 1H, indole-6H), 6.005 (s, 1H, indole-3H), 5.157 (s, 2H, methylene), 3.849 (s, 3H, o-methyl), 2.331 (s, 3H, c-methyl). 13C NMR (150 MHz, d6-DMSO): δ 166.1, 151.9, 143.6, 136.3, 131.4, 129.3, 129.0, 128.7, 127.4, 111.0, 110.1, 102.8, 99.0, 69.0, 52.1, 13.4. Melting point: 151-154° C. TLC (in 1:1 ethyl acetate:hexanes) Rf=0.49 (doubly alkylated product Rf=0.42). Elemental analysis calculated for C19H17NO3: C, 73.20; H, 5.80; N, 4.74. found: C, 73.02; H, 5.82; N, 4.55.

5-(4-Methylbenzoate)methoxy-2-methyl-1H-indole-3-carboxaldehyde (compound 24)

To a dried two-neck 250 mL round bottom flask under argon, POCl3 (325 μL, 3.5 mmol) was added to N.Ndimethylformamide (8 mL) at 0° C. After stirring for five minutes, compound 23 (320 mg, 1.08 mmol) dissolved in DMF (4 mL) was added dropwise. The yellow solution was slowly warmed to room temperature and after one hour sat. NaHCO3 was added (50 mL), producing a white precipitate, followed by 1N NaOH (20 mL) to complete precipitation (direct workup with NaOH resulted in roughly 1:1 mixture of ester product to ester-hydrolyzed analog). The solid was filtered, rinsed with cold H2O and dried under vacuum, yielding 315 mg of white solid (90%). 1H NMR (600 MHz, d6-DMSO): δ 11.902 (s, 1H, N—H), 10.000 (s, 1H, CHO), 7.991-7.977 (d, J=8.4, 2H, phenyl-3,5H), 7.664-7.660 (d, J=2.4, 1H, indole-4H), 7.633-7.619 (d, J=8.4, 2H, phenyl-2,6H), 7.304-7.290 (d, J=8.4, 1H, indole-7H), 6.906-6.887 (dd, J1=9.0, J2=2.4, 1H, indole-6H), 5.211 (s, 2H, methylene), 3.854 (s, 3H, o-methyl), 2.646 (s, 3H, c-methyl). 13C NMR (150 MHz, d6-DMSO): δ 184.0, 166.1, 154.3, 148.7, 143.2, 130.4, 129.3, 128.8, 127.4, 126.4, 113.6, 112.3, 112.2, 104.0, 69.0, 52.1, 11.5. Melting point: 224-227° C. TLC: (in ethyl acetate:hexanes 4:1) Rf=0.35. Elemental analysis calculated for C19H17NO4: C, 70.58; H, 5.30; N, 4.33. found: C, 70.45; H, 5.41; N, 4.51.

5-(4-Benzoate)methoxy-2-methyl-1H-indole-3-carboxaldehyde (compound 25)

To a dried two-neck 250 mL round bottom flask under argon, POCl3 (565 μL, 6.1 mmol) was added to N.Ndimethylformamide (12 mL) at 0° C. After stirring for five minutes, compound 23 (600 mg, 2.03 mmol) dissolved in DMF (9 mL) was added dropwise. The yellow solution was slowly warmed to room temperature. After one hour, the reaction was cooled to 0° C. and 5N NaOH (90 mL) was added. After stirring for 30 minutes, 5N HCl (95 mL) was added to precipitate the product, which was filtered and dried overnight under vacuum, yielding 626 mg (99%) of white solid. 1H NMR (600 MHz, d6-DMSO): δ 11.944 (s, 1H, N—H), 10.001 (s, 1H, CHO), 7.961-7.947 (d, J=8.4, 2H, phenyl-3,5H), 7.664-7.660 (d, J=2.4, 1H, indole-4H), 7.590-7.576 (d, J=8.4, 2H, phenyl-2,6H), 7.304-7.290 (d, J=8.4, 1H, indole-7H), 6.902-6.884 (dd, J1=8.4, J2=2.4, 1H, indole-6H), 5.194 (s, 2H, methylene), 2.647 (s, 3H, methyl). 13C NMR (150 MHz, d6-DMSO): δ 184.0, 167.3, 154.4, 148.8, 142.5, 130.4, 129.4, 127.3, 127.2, 126.4, 113.6, 112.3, 112.2, 104.0, 69.1, 11.5. Melting point: 267-270° C. TLC: (in ethyl acetate: hexanes 4:1) Rf=0.25.

trans-3-[5-((4-Methylbenzoate)methoxy)-1H-Indol-3-yl)]-1-(4-pyridinyl)-2-propen-1-one (compound 26)

In a dried 100 mL two-neck round bottom flask under argon, compound 24 (50 mg, 0.15 mmol) was partially dissolved in anhydrous methanol (2 mL). 4-Acetyl-pyridine (26 μL, 0.23 mmol) and piperidine (7 μL, 0.075 mmol) were added and the reaction was refluxed. A yellow precipitate gradually formed, and after 24 hours the reaction was brought to room temperature and the solid was isolated by filtration, rinsed with cold methanol and dried under vacuum, yielding 36 mg. However, crude NMR showed 1:0.15 product:aldehyde. This mixture was dry loaded onto silica and purified by column chromatography (ethyl acetate:hexanes 2:1), providing 22 mg pure product (34%). 1H NMR (600 MHz, d6-DMSO): δ 11.937 (s, 1H, N—H), 8.829-8.819 (d, J=6.0, 2H, pyr-2,6H), 8.069-8.044 (d, J=15.0, 1H, C═CH), 7.971-7.957 (d, J=8.4, 2H, phenyl-3,5H), 7.905-7.896 (d, J=5.4, 2H, pyr-3,5H), 7.662-7.649 (d, J=7.8, 2H, phenyl-2,6H), 7.479-7.475 (d, J=2.4, 1H, indole-4H), 7.326-7.312 (d, J=8.4, 1H, indole-7H), 7.284-7.259 (d, J=15.0, 1H, C═CH), 6.938-6.920 (dd, J1=8.7, J2=2.1, 1H, indole-6H), 5.358 (s, 2H, methylene), 3.838 (s, 3H, o-methyl), 2.561 (s, 3H, c-methyl). 13C NMR (150 MHz, d6-DMSO): δ 188.1, 166.0, 153.9, 150.6, 146.0, 145.1, 143.5, 139.5, 131.3, 129.3, 128.8, 127.4, 126.4, 121.4, 112.8, 112.4, 111.9, 109.3, 104.8, 69.2, 52.2, 12.1. Melting Point: 236-239° C. TLC (ethyl acetate:hexanes4:1) Rf=0.26. Elemental analysis calculated for C26H22N2O4.0.25 C4H8O2: C, 72.31; H, 5.39; N, 6.25. found: C, 72.62; H, 5.64; N, 5.95.

trans-3-[5-((4-Carboxyphenyl)-methoxy)-1H-Indol-3-yl)]-1-(4-pyridinyl)-2-propen-1-one (compound 27)

In a dried 100 mL round bottom flask under argon, compound 25 (200 mg, 0.65 mmol) was partially dissolved in anhydrous methanol (15 mL). 4-Acetyl-pyridine (107 μL, 0.97 mmol, 1.5 equiv.) and piperidine (256 μL, 0.65 mmol) were added and the reaction was refluxed. After 24 hours, the solid precipitate was isolated by filtration, yielding 75 mg of product contaminated with aldehyde. Due to both solubility and poor filtration, plenty of product remained in the filtrate; thus, the filtrate was dry loaded onto silica and purified by column chromatography (methylene chloride:methanol 9:1), yielding 85 mg of purified acid product (21%). 1H NMR (600 MHz, d6-DMSO): δ 11.947 (s, 1H, N—H), 8.831-8.821 (dd, J1=4.2, J2=1.8, 2H, pyr-2,6H), 8.073-8.047 (d, J=15.6, 1H, C═CH), 7.954-7.941 (d, J=7.8, 2H, phenyl-3,5H), 7.904-7.894 (dd, J1=4.2, J2=1.8, 2H, pyr-3,5H), 7.630-7.616 (d, J=8.4, 2H, phenyl-2,6H), 7.479-7.476 (d, J=1.8, 1H, indole-4H), 7.326-7.312 (d, J=8.4, 1H, indole-7H), 7.289-7.264 (d, J=15.0, 1H, C=CH), 6.939-6.920 (dd, J1=9.0, J2=2.4, 1H, indole-6H), 5.349 (s, 2H, methylene), 2.562 (s, 3H, methyl). 13C NMR (150 MHz, d6-DMSO): δ 188.1, 167.3, 154.0, 150.6, 146.0, 145.1, 142.8, 139.6, 131.2, 130.3, 129.5, 127.2, 126.4, 121.4, 112.8, 112.4, 111.9, 109.3, 104.8, 69.3, 12.1. Melting point: 269-273° C. TLC (methylene chloride:methanol 9:1) Rf=0.41. Elemental analysis calculated for C25H20N2O4.0.25 CH2Cl2.0.25 CH3OH: C, 69.34; H, 4.91; N, 6.34. found: 69.28; H, 5.22; N, 6.72.

2-Methyl-5-benzoyl-indole-3-carboxaldehyde and 2-Methyl-6-benzoyl-indole-3-carboxaldehyde (compounds 28 and 29)

In a dried two-neck 250 mL round bottom flask under argon, N,Ndimethylformamide (339 μL, 4.4 mmol) was added to 1,2-dichloroethane (8 mL). The reaction was cooled to 0° C. and oxalyl chloride (377 μL, 4.4 mmol) dissolved in 1,2-DCE (8 mL) was slowly added, forming a white heterogeneous mixture. The mixture was allowed to warm to room temperature while stirring. After fifteen minutes, the reaction was cooled to 0° C. and 2-methylindole (577 mg, 4.0 mmol) dissolved in 1,2-DCE (8 mL) was slowly added, forming a dark red solution. After one hour, AlCl3 (1.96 g, 14.7 mmol) was added and stirred vigorously. Benzoyl chloride (510 μL, 4.4 mmol) dissolved in 1,2-DCE (4 mL) was slowly added and the reaction was warmed to room temperature and stirred overnight. After 24 hours, cold H2O (50 mL) was added, followed by 5N NaOH (10 mL), and the mixture was stirred. After one hour, 5N HCl (18 mL) was added and this was extracted with methylene chloride (3×50 mL). The combined 1,2-DCE and methylene chloride extracts were combined, dried with Na2SO4, filtered and concentrated. The crude product mixture was purified by column chromatography (ethyl acetate:hexanes 1:1-4:1), yielding 5-benzoyl product 28 (142 mg, 13%) and 6-benzoyl product 29 (429 mg, 41%) (1:3 regioselectivity for 5 vs. 6 benzoylation).

2-Methyl-5-benzoyl-indole-3-carboxaldehyde (compound 28)

1H NMR (600 MHz, d6-DMSO): δ 12.371 (s, 1H, N—H), 10.073 (s, 1H), CHO, 8.462 (s, 1H, indole-4H), 7.723-7.711 (m, 2H, phenyl-2,6H), 7.673-7.656 (m, 2H, indole-6H, phenyl-4H), 7.587-7.561 (t, J=7.8, 2H, phenyl-3,5H), 7.553-7.539 (d, J=8.4, 1H, indole-7H), 2.728 (s, 3H, methyl). 13C NMR (150 MHz, d6-DMSO): δ 196.1, 184.8, 150.8, 138.3, 138.0, 132.1, 130.9, 129.5, 128.5, 124.9, 124.7, 123.4, 114.4, 111.6, 11.6. 1-D nOe: irradiation of peak at δ 12.371 (N—H): nOe signal enhancement seen at δ 7.549 (C—H) and 2.728 (CH3). The H peak at 7.549 has ortho coupling (J=8.4), proving the benzoyl group inserted at the 5 position, not 6. Separately, irradiation of peak at δ 7.540 (C—H with ortho coupling): nOe signal enhancement seen at δ 12.370 (N—H), again proving the proximity of N—H to an ortho-coupled C7-H; signal enhancement also seen at δ 7.66 for C6-H (the benzoyl 2H triplet peak at δ 7.574 was also irradiated by proximity, thus signal enhancement was seen for the other benzoyl C—H peaks at δ 7.72 and δ 7.67). Melting point: 227-230° C. TLC (ethyl acetate:hexanes 4:1) Rf=0.32. Elemental analysis calculated for C17H13NO2_0.2 C4H8O2 (trace ethyl acetate): C, 76.11: H, 5.24; N, 4.99. found: C, 75.74; H, 4.94; N, 5.06.

2-Methyl-6-benzoyl-indole-3-carboxaldehyde (compound 29)

1H NMR (600 MHz, d6-DMSO): δ 12.323 (s, 1H, N—H), 10.116 (s, 1H, CHO), 8.173-8.159 (d, J=8.4, 1H, indole-4H), 7.776-7.774 (d, J=1.2, 1H, indole-7H), 7.741-7.729 (m, 2H, phenyl-2,6H), 7.683-7.659 (t, J=7.2, 1H, phenyl-4H), 7.627-7.611 (dd, J1=7.8, J2=1.8, 1H, indole-5H), 7.583-7.558 (t, J=7.5, 2H, phenyl-3,5H), 2.744 (s, 3H, methyl). 13C NMR (150 MHz, d6-DMSO): δ 196.3, 185.4, 152.2, 138.7, 135.3, 132.8, 131.8, 130.1, 129.8, 129.1, 124.4, 120.3, 114.7, 114.4, 12.5. 1-D nOe: irradiation of peak at δ 12.323 (N—H): nOe signal enhancement seen at δ 7.775 (C—H with meta coupling, thus proving benzoyl addition to position 6 of indole) and δ 2.744 (CH3). Separately, irradiation of the peak at δ 7.775 (C—H with meta coupling: J=1.2) led to signal enhancement at δ 12.323 (N—H peak), thus proving proximity of meta-coupled C—H to N—H (the benzoyl 2,6 2H peak at 7.73 was also irradiated by proximity, leading to signal enhancement of benzoyl 3,5 2H peak at δ 7.57). Melting point: 192-196° C. TLC (ethyl acetate:hexanes 4:1) Rf=0.40. Elemental analysis calculated for C17H13NO2: C, 77.55; H, 4.98; N, 5.32. found: C, 77.28; H, 4.97; N, 5.15.

trans-3-(5-Benzoyl-2-methyl-1H-indol-3-yl)-1-(4-pyridinyl)-2-propen-1-one (compound 30)

In a dried 100 mL round bottom flask under argon, compound 28 (50 mg, 0.19 mmol) was dissolved in anhydrous methanol (3 mL). 4-Acetyl-pyridine (21 μL, 0.19 mmol) and piperidine (4 μL, 0.04 mmol) were added and the reaction was refluxed. After twelve hours, 0.3 equivalents of 4-acetylpyridine (6.3 μL, 0.06 mmol) was added. After a total of 24 hours reaction time, the reaction was cooled and the precipitate was isolated by filtration and rinsed with cold methanol, providing 37 mg of yellow solid. A crude 1H NMR showed a 1:3.5 ratio of product to aldehyde. The filtrate was concentrated and added to the product/aldehyde mixture, and 0.8 equivalents of both 4-acetyl-pyridine (17 μL, 0.15 mmol) and piperidine (15 μL, 0.15 mmol) were added to the reaction. This was refluxed for another 24 hours, after which the reaction was cooled, filtered and rinsed with cold methanol, providing 9 mg (13%) pure, yellow product. 1H NMR (600 MHz, d6-DMSO): δ 12.397 (s, 1H, N—H), 8.815-8.805 (m, 2H, pyr-2.6H), 8.321 (s, 1H, indole-4H), 8.081-8.056 (d, J=15.0, 1H, C=CH), 7.820-7.808 (d, J=7.2, 2H, phenyl-2,6H), 7.761-7.728 (m, 4H, phenyl-4H, indole-6H, pyr-3,5H), 7.644-7.619 (t, J=7.5, 2H, phenyl-3,5H), 7.587-7.573 (d, J=8.4, 1H, indole-7H), 7.347-7.321 (d, J=15.6, 1H, C=CH), 2.639 (s, 3H, methyl). 13C NMR (150 MHz, d6-DMSO): δ 195.7, 187.9, 150.6, 146.9, 144.7, 138.8, 138.5, 138.4, 131.9, 130.1, 129.4, 128.4, 125.2, 123.9, 123.6, 121.1, 114.6, 111.9, 110.1, 12.1. Melting point: 258-262° C. TLC (ethyl acetate:hexanes 4:1) Rf=0.24. Elemental analysis calculated for C24H18N2O2_0.65 H2O: C, 76.24; H, 5.14; N, 7.41; C, 75.96; H, 4.75; N, 7.16.

trans-3-(6-Benzoyl-2-methyl-1H-indol-3-yl)-1-(4-pyridinyl)-2-propen-1-one (compound 31)

In a dried 100 mL round bottom flask under argon, compound 29 (50 mg, 0.19 mmol) was dissolved in anhydrous methanol (3 mL). 4-Acetyl-pyridine (21 μL, 0.19 mmol) and piperidine (19 μL, 0.19 mmol) were added and the reaction was refluxed. After 24 hours, the reaction was cooled, filtered and rinsed with cold hexanes and dried under vacuum, yielding 52 mg (74%) of pure yellow solid. 1H NMR (600 MHz, d6-DMSO): δ 12.350 (s, 1H, N—H), 8.832-8.222 (d, J=6.0, 2H, pyr-2,6H), 8.255-8.241 (d, J=8.4, 1H, indole-4H), 8.125-8.099 (d, J=15.6, 1H, C=CH), 8.008-7.999 (d, J=5.4, 2H, pyr-3,5H), 7.801 (s, 1H, indole-7H), 7.766-7.754 (d, J=7.2, 2 H, phenyl-2,6H), 7.683-7.642 (m, 2H, phenyl-4H, indole-5H), 7.585-7.563 (m, 3H, C=CH, phenyl-3,5H), 2.659 (s, 3H, methyl). 13C NMR (150 MHz, d6-DMSO): δ 195.5, 188.2, 150.6, 148.5, 144.6, 138.7, 138.2, 135.4, 132.0, 130.6, 129.4, 129.2, 128.4, 123.1, 121.5, 119.9, 114.5, 114.1, 109.6, 12.3. Melting point: 267-270° C. TLC (ethyl acetate:hexanes 4:1) Rf=0.29. Elemental analysis calculated for C24H18N2O2_0.05 H2O: C, 78.48; H, 4.97; N, 7.63. found: C, 78.08; H, 5.01; N, 7.50.

2-Methyl-5-nitro-1H-indole (compound 32)

In a 250 mL round bottom flask, 2.62 grams of 2-methyl-indole (20 mmol) was dissolved in 20 mL of H2SO4 after vigorous stirring. In a separate flask, 1.87 grams of NaNO3 (1.1×, 22 mmol, 84.99 MW) was dissolved in 20 mL of H2SO4, also after vigorous stirring, and added dropwise via addition funnel to the indole. After addition, the reaction was stirred for another 10 minutes, and then poured into 400 mL of ice-water, precipitating a yellow product. The product was isolated via filtration and washed with cold water. After 12 hours of drying under vacuum, 3.35 grams of yellow product was isolated (95%). 1H NMR (600 MHz, d6-DMSO): δ 11.703 (s, 1H, N—H), 8.4003-8.400 (d, J=1.8, 1H, indole-4H), 7.916-7.898 (dd, J1=9.0, J2=1.8, 1H, indole-6H), 7.422-7.407 (d, 1H, J=9.0, 1H, indole-7H), 6.408 (s, 1H, indole-3H), 2.419 (s, 1H, methyl). 13C NMR (150 MHz, d6-DMSO): δ 140.5, 140.0, 139.4, 128.0, 115.9, 115.7, 110.7, 101.6, 13.4. 1-D nOe: irradiation of peak at δ 7.422-7.407 (C7-H): nOe signal enhancement seen at δ 11.690 (N—H) and 7.916-7.897 (C6-H). Irradiation of peak at 11.690 (N—H): nOe signal enhancement seen at δ 7.422-7.407 (C7-H) and 2.419 (C2-CH3) (nOe observed between the C—H proton with ortho coupling and N—H proton, thus proving NO2 inserted at indole C-5 vs. C-6). Melting point: 166-169° C. TLC (in 1:1 ethyl acetate:hexanes) Rf=0.38. Elemental analysis calculated for C9H8N2O2: C, 61.36; H, 4.58; N, 15.90. found: C, 61.54; H, 4.63; N, 15.89.

2-Methyl-5-amino-1H-indole (compound 33)

Compound 32 (1.00 grams, 5.68 mmol) was dissolved in 75 mL ethanol. 10% Pd/C was added (200 mg) and the mixture was subjected to H2 (38 psi) using a Parr hydrogenator for 3.5 hours. The mixture was filtered over celite, which was washed with methanol. After concentration and drying under vacuum, 801 mg of a brown powder (97%) was isolated. 1H NMR (600 MHz, d6-DMSO): δ 10.370 (s, 1H, N—H), 6.943-6.929 (d, J=8.4, 1H, indole-7H), 6.552-6.549 (d, J=1.8, 1H, indole-4H), 6.373-6.355 (dd, J1=8.4, J2=2.4, 1H), 5.815 (s, 1H, indole-6H), 4.436 (bs, 2H, NH2), 2.288 (s, 3H, methyl). 13C NMR (150 MHz, d6-DMSO): δ 140.8, 135.0, 129.9, 129.6, 110.5, 110.3, 102.9, 98.0, 13.5. Melting point: 147-150° C. TLC (in 3:1 ethyl acetate:hexanes) Rf=0.30; (in 1:1 ethyl acetate:hexanes) Rf=0.16. Elemental analysis calculated for C9H10N2_0.05 C2H6O: C, 73.61; H, 6.99; N, 18.87. found: C, 73.48; H, 6.77; N, 18.81.

2-Methyl-5-azido-1H-indole (compound 34)

In an oven dried, 250 mL round bottom flask flushed with argon, compound 33 (400 mg, 2.74 mmol, 146.19 MW) was dissolved in 90% AcOH (20 mL). After complete solvation, the reaction was placed at 0° C. and protected from light with foil. NaNO2 (1.1×, 3.01 mmol, 208 mg, 69.00 MW) dissolved in cold H2O (2 mL) was added dropwise and stirred for ten minutes. NaN3 (1.1×, 3.01 mmol, 196 mg, 65.01 MW) dissolved in cold H2O (2 mL) was added dropwise. After one hour the reaction was poured into water (40 mL), which was extracted 3 times with CH2Cl2 (40 mL each). The extracts were washed with sodium bicarbonate and brine (100 mL each), dried with sodium sulfate, filtered and concentrated. Purification by silica flash chromatography (100% CH2Cl2) yielded the azide as a light brown solid (310 mg, 66%). 1H NMR (600 MHz, d6-DMSO): δ 11.025 (s, 1H, N—H), 7.295-7.281 (d, J=8.4, 1H, indole-7H), 7.131-7.127 (d, J=2.4, 1H, indole-4H), 6.737-6.719 (dd, J1=8.4, J2=2.4, 1H, indole-6H), 6.108-6.106 (d, J=1.2, 1H, indole-3H), 2.369 (s, 1H, methyl). 13C NMR (150 MHz, d6-DMSO): δ 137.5, 133.9, 130.0, 129.5, 111.7, 111.6, 108.5, 99.0, 13.4. Melting point: 57-60° C. TLC (in 1:1 ethyl acetate:hexanes) Rf=0.56. IR (film): 3409 cm.−1, 2111 (aryl-azide). Elemental analysis calculated for C9H8N4: C, 62.78; H, 4.68; N, 32.54. found: C, 62.95; H, 4.68; N, 32.53.

2-Methyl-3-carboxaldehyde-5-azido-1H-indole (compound 35)

In an oven dried, 100 mL round bottom flask purged with argon, POCl3 (1.5×, 3.14 mmol, 291 µL) was added to anhydrous DMF (2.0 mL) at 0° C. Compound 34 (dissolved in DMF, 2 mL) was added dropwise. The stirred reaction was slowly warmed to RT. 1N NaOH (25 mL) and water (25 mL) was added, forming a precipitate which was filtered and rinsed with cold water. The resulting white solid was dried under vacuum, affording 369 mg (88%). 1H NMR (600 MHz, d6-DMSO): δ 12.078 (s, 1H, N—H), 10.031 (s, 1H, CHO), 7.754-7.751 (d, J=1.8, 1H, indole-4H), 7.423-7.409 (d, J=8.4, 1H, indole-7H), 6.913-6.896 (dd, J1=8.4, J2=1.8, 1H, indole-6H), 2.676 (s, 3H, methyl). 13C NMR (150 MHz, d6-DMSO): δ 184.3, 149.7, 133.4, 133.0, 126.6, 114.4, 113.4, 112.8, 109.4, 11.5. Melting point: degradation ca. 150° C. TLC (in 1:1 ethyl acetate:hexanes) Rf=0.19. Elemental analysis calculated for C10H8N4O: C, 59.99; H, 4.03; N, 27.99. found: C, 60.03; H, 4.07; N, 27.96.

trans-3-(5-Azido-2-methyl-1H-indol-3-yl)-1-(4-pyridinyl)-2-propen-1-one (compound 36)

In a dried, 100 mL round bottom flask under argon and protected from light, compound 35 (80 mg, 0.40 mmol) was partially dissolved in anhydrous methanol (5 mL). 4-Acetyl-pyridine (1.5 equiv., 66 µL, 0.60 mmol) and piperidine (40 µL, 0.40 mmol) were added and the reaction was stirred at 40° C. After 24 hours, the reaction was cooled to RT and the yellow precipitate was isolated via filtration and rinsed with cold methanol. A crude 1H NMR of this product showed a ca. 1:3 ratio of product to the indole starting material. This crude product was redissolved in anhydrousmethanol (5 mL) along with the concentrated filtrate, and another equivalent of 4-acetyl-pyridine (44 µL, 2.5 equiv. total) and five equivalents of piperidine (200 µL, 6 equiv. total) were added. The stirred reaction was heated at 40° C. After 12 hours, a yellow precipitate was filtered and rinsed with cold methanol and dried under vacuum, affording 47 mg (39%) of pure product. 1H NMR (600 MHz, d6-DMSO): δ 12.105 (s, 1H, N—H), 8.816-8.806 (dd, J1=4.8, J2=1.8, 2H, pyr-2,6H), 8.066-8.041 (d, J=15, 1H, C=CH), 7.956-7.945 (dd, J1=4.8, J2=1.8, 2H, pyr-3,5H), 7.661-7.657 (d, J=2.4, 1H, indole-4H), 7.455-7.441 (d, J=8.4, 1H, indole-7H), 7.401-7.375 J=15.6, 1H, C=CH), 7.001-6.984 (dd, J1=8.4, J2=1.8, indole-6H), 2.587

(s, 3H, methyl). 13C NMR (150 MHz, d6-DMSO): δ 188.2, 150.6, 146.5, 144.9, 139.0, 133.9, 132.9, 126.8, 121.5, 113.9, 113.8, 113.0, 110.3, 109.2, 12.2. Melting point: decomposes ca. 190° C. TLC (in 4:1 ethyl acetate:hexanes) Rf=0.21. Elemental analysis calculated for C17H13N5O: C, 67.32; H, 4.32; N, 23.09. found: C, 67.37; H, 4.33; N, 23.12.

2-Methyl-5-methoxy-6-nitro-1H-indole (compound 37)

In a 100 mL round bottom flask, 2-methyl-5-methoxyindole (370 mg, 2.30 mmol) was dissolved in H2SO4 (4 mL) after vigorous stirring, then placed at 0° C. In a separate flask, 1.87 grams of NaNO3 (214 mg, 2.52 mmol) was dissolved in H2SO4, (4 mL) also after vigorous stirring, chilled to 0° C., and added dropwise to the indole. After addition, the reaction was stirred for another 10 minutes, and then poured into ice-water (200 mL), precipitating a yellow product, which was extracted with ethyl acetate (3×100 mL). Extracts were washed with sat. NaHCO3 and brine, dried with Na2SO4, filtered and concentrated. Purification by column chromatography (ethyl acetate:hexane 2:3-3:2) yielded 296 mg of pure product (62%), (followed by 73 mg of 4-nitrated product, 15%; 4:1 regioselectivity). 1H NMR (600 MHz, CDCl3): δ 8.350 (s, 1H, N—H), 7.983 (s, 1H, indole-7H), 7.066 (s, 1H, indole-4H), 6.211 (s, 1H, indole-3H), 3.958 (s, 3H, o-methyl), 2.477 (s, 3H, c-methyl). 13C NMR (150 MHz, CDCl3): δ 148.7, 142.8, 134.7, 134.2, 129.1, 109.2, 102.7, 101.3, 57.1, 14.2. Melting point: 134-138° C. TLC (in 1:1 ethyl acetate: hexanes) Rf=0.37 (4-nitro product Rf=0.25). Elemental analysis calculated for C10H10N2O3_0.1 C6H14: C, 59.27; H, 5.35; N, 13.04. found: C, 59.33; H, 5.10; N, 12.98.

2-Methyl-5-methoxy-6-amino-1H-indole (compound 38)

In a hydrogenation flask, compound 37 (270 mg, 1.31 mmol) was dissolved in 100% EtOH (35 mL) and 10% Pd/C (40 mg) was added. The mixture was hydrogenated on a Parr hydrogenator at 40 p.s.i. for 45 minutes. The red-pink solution was filtered over celite and rinsed with MeOH, concentrated and dried under vacuum, yielding 230 mg of pure product (99%). 1H NMR (400 MHz, CDCl3): δ 7.516 (s, 1H, N—H), 6.907 (s, 1H), 6.607 (s, 1H), 6.052 (s, 1H, indole-3H), 3.873 (s, 3H, o-methyl), 3.733 (bs, 2H, NH2), 2.365 (s, 3H, c-methyl). 13C NMR (150 MHz, d6-DMSO): δ 142.8, 132.9, 131.5, 131.4, 119.5, 100.5, 98.7, 95.7, 55.6, 13.5 Melting point: 144-148° C. TLC (in 3:1 ethyl acetate:hexanes) Rf=0.33. Elemental analysis calculated for C10H10N2O3_0.1 C6H14: C, 59.27; H, 5.35; N, 13.04. found: C, 59.33; H, 5.10; N, 12.98.

2-Methyl-5-methoxy-6-azido-1H-indole (compound 39)

In a dried, 100 mL round bottom flask under argon, compound 38 (227 mg, 1.29 mmol) was dissolved in 90% AcOH (10 mL) and placed at 0° C. The flask was covered with foil and the reaction was conducted in low light. NaNO2 (98 mg, 1.43 mmol, 1.1 equiv) dissolved in H2O (1 mL) was added dropwise, and the mixture stirred for 10 minutes. $NaN_3$ (92 mg, 1.43 mmol, 1.1 equiv.) dissolved in H2O (1 mL) was added dropwise. After 45 minutes, the mixture was slowly poured into H2O (25 mL) and sat. K2CO3 (19 mL) to form a neutral pH. This was extracted with ethyl acetate (4×50 mL), washed with brine, dried with Na2SO4, filtered and concentrated. The crude product was purified by column chromatography (ethyl acetate:hexanes 1:4), yielding 139 mg of pure oil (53 To). 1H NMR (600 MHz, CDCl3): δ 7.782 (s, 1H, N—H), 7.007 (s, 1H), 6.883 (s, 1H), 6.145 (s, 1H, indole-3H), 3.890 (s, 3H, o-methyl), 2.388 (s, 3H, c-methyl). 13C NMR (150 MHz, CDCl3): δ 147.0, 136.1, 130.7, 126.5, 123.1, 102.4, 102.0, 100.4, 56.5, 13.7. TLC (in 1:1 ethyl acetate:hexanes) Rf=0.60.

2-Methyl-3-carboxaldehyde-5-methoxy-6-azido-1H-indole (compound 40)

In an oven dried, 100 mL round bottom flask, purged with argon and protected from light with foil, POCl3 (84 μL, 0.90 mmol, 1.5 equiv.) was added to anhydrous DMF (1.0 mL) at 0° C. and stirred for 5 minutes. Next, compound 39 (dissolved in DMF, 1 mL) was added dropwise. The stirred reaction was slowly warmed to RT. 1N NaOH (10 mL) and water (10 mL) were added, and this was extracted with CH2Cl2 (3×20 mL). Extracts were washed with brine, dried with Na2SO4, filtered, concentrated and dried overnight under vacuum, producing 95 mg pure product (69%). 1H NMR (600 MHz, d6-DMSO): δ 11.865 (s, 1H, N—H), 10.004 (s, 1H, CHO), 7.645 (s, 1H, indole-4H), 7.032 (s, 1H, indole-7H), 3.857 (s, 3H, o-methyl), 2.645 (s, 3H, c-methyl). 13C NMR (150 MHz, d6-DMSO): δ 184.8, 149.5, 149.4, 130.3, 124.1, 124.0, 114.4, 104.2, 103.5, 56.9, 12.2. TLC (in 1:1 ethyl acetate: hexanes) Rf=0.12.

trans-3-(6-Azido-5-methoxy-2-methyl-1H-indol-3-yl)-1-(4-pyridinyl)-2-propen-1-one (compound 41)

In a dried, 100 mL round bottom flask under argon and protected from light, compound 40 (70 mg, 0.30 mmol) was partially dissolved in anhydrous methanol (5 mL). 4-Acetylpyridine (50 μL, 0.45 mmol, 1.5 equiv.) and piperidine (148 μL, 1.5 mmol, 5 equiv.) were added and the reaction was stirred at 40° C. After 7 hours, the reaction was cooled to RT and the precipitate was isolated via filtration and rinsed with cold methanol. A crude 1H NMR of this product showed a mixture of aldehyde with trace product. This mixture was redissolved in the filtrate and more 4-acetylpyridine (165 μL, 5 equiv.) and piperidine (148 μL, 5 equiv.) was added and the mixture was set to react at 40° C. After 48 hours, although starting materials are still seen on TLC, the crude reaction mixture was dry loaded onto silica and purified by column chromatography (ethyl acetate:hexane 3:1), eluting first the aldehyde, followed by the ketone and finally the product as a yellow solid (39 mg, 39%). 1H NMR (600 MHz, d6-DMSO): δ 11.784 (s, 1H, N—H), 8.815-8.805 (dd, J1=4.2, J2=1.8, 2H, pyr-2,6H), 8.073-8.047 (d, J=15.6, 1H, C═CH), 7.957-7.947 (dd, J1=4.2, J2=1.8, 2H, pyr-3,5H), 7.538 (s, 1H, indole-4H), 7.410-7.384 (d, J=15.6, 1H, indole C═CH), 7.051 (s, 1H, indole-7H), 3.982 (s, 3H, o-methyl), 2.569 (s, 3H, c-methyl). 13C NMR (150 MHz, d6-DMSO): δ 188.2, 150.6, 148.5, 145.6, 145.0, 139.1, 130.6, 123.6, 123.3, 121.5, 113.5, 109.5, 103.8, 103.7, 56.9, 12.3. Melting point: degrades to black substance ca. 160° C. TLC (in 4:1 ethyl acetate:hexanes) Rf=0.15. Elemental analysis calculated for C18H15N5O2_C4H8O2 (trace ethyl acetate): C, 64.72; H, 4.60; N, 20.74. found: C, 65.11; H, 4.71; N, 20.39.

While the invention has been described with reference to various and preferred embodiments, it should be understood by those skilled in the art that various changes can be made and equivalents can be substituted for elements thereof without departing from the essential scope of the invention. In addition, many modifications can be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated by reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A compound having the structure of Formula I:

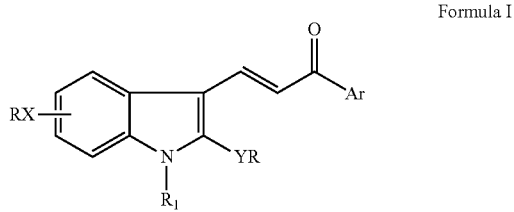

Formula I wherein X and Y are independently absent or halogen, oxygen, azide, nitrogen, (CO)O, O(CO), O(CO)O, (CO)N, NH(CO), NH(CO)N, NH(CO)O, or O(CO)N;
wherein when X or Y is halogen or azide, then R is absent, and
wherein when X or Y is nitrogen, (CO)N, O(CO)N, or NH(CO)N, then two R groups are present;
wherein each R is independently hydrogen, alkyl, alkenyl, alkynyl, aryl, or aralkyl;
wherein $R_1$ is hydrogen, alkyl, alkenyl, or alkynyl;
wherein Ar is heteroaryl;
wherein when XR is hydrogen and Y is absent, then R is not hydrogen or methyl; and
wherein when XR is halide and Y is absent, then R is not hydrogen;
and pharmaceutically acceptable salts, hydrates, and optical isomers thereof.

2. The compound of claim 1, wherein XR is methoxy bound at the 5 position, YR is methyl, and $R_1$ is hydrogen.

3. A compound of claim 2, wherein Ar is 4-pyridyl.

4. The compound of claim 1, which is capable of inducing methuosis.

5. A method of inducing cell death in at least one cell, comprising introducing a compound of claim 1 to at least one cell and inducing cell death.

6. A method of claim 5, wherein the at least one cell is a mammalian cell.

7. A method of claim 5, wherein the at least one cell is drug-resistant.

8. A method of claim 5, wherein the at least one cell is apoptosis-resistant.

9. A method of claim 5, wherein the at least one cell is a cancer cell.

10. A method of claim 5, wherein the at least one cell is a cancer stem cell.

11. A method of claim 5, wherein the at least one cell is a human cell.

12. A method of inducing cell death in a mammal in need of such induction, comprising administering to a subject a pharmacologically effective amount of a compound of claim 1.

13. The method of claim 12, wherein the mammal is selected from the group consisting of: mouse; rat; guinea pig; rabbit; cat; dog; monkey; goat; cow; horse; and human.

14. A method of ameliorating the effects of cancer in a mammal in need of such amelioration, comprising administering to a subject a pharmacologically effective amount of a compound of claim 1.

15. A method of claim 14, wherein the cancer is selected from the group consisting of: brain, lung, pancreas, bone, bladder, colon, stomach, breast, prostate, ovary, central nervous system, or skin.

16. The method of claim 14, wherein the mammal is selected from the group consisting of: mouse; rat; guinea pig; rabbit; cat; dog; monkey; goat; cow; horse; and human.

17. The method of claim 14, wherein the method further comprises administering a second compound, adjuvant or additional therapeutic to the mammal.

18. A composition of matter comprising a compound of claim 1 and a cancer therapeutic.

19. A composition of claim 18, wherein the cancer therapeutic is selected from the group consisting of chemotherapeutic drug; toxin; immunological response modifier; enzyme; and radioisotope.

20. The method of claim 14, wherein the cancer is resistant to therapeutic agents that cause cells to die by apoptosis or other methods.

21. A compound of claim 1 selected from the group consisting of:
trans-3-(2-Methyl-1H-indol-3-yl)-1-(4-pyridinyl)-2-propen-1-one;
trans-3-(1H-Indol-3-yl)-1-(2-pyridinyl)-2-propen-1-one;
trans-3-(1H-Indol-3-yl)-1-(3-pyridinyl)-2-propen-1-one;
trans-3-(1H-Indol-3-yl)-1-(4-pyridinyl)-2-propen-1-one;
trans-3-(5-Methoxy-1H-indol-3-yl)-1-(4-pyridinyl)-2-propen-1-one;
trans-3-(5-Phenylmethoxy-1H-indol-3-yl)-1-(4-pyridinyl)-2-propen-1-one;
trans-3-(5-Hydroxy-1H-Indol-3-yl)-1-(4-pyridinyl)-2-propen-1-one;
trans-3-(5-Methoxy-1H-indol-3-yl)-1-(3-pyridinyl)-2-propen-1-one;
trans-3-(5-Methoxy-1H-indol-3-yl)-1-(pyrazine)-2-propen-1-one;
trans-3-(5-Methoxy-2-methyl-1H-indol-3-yl)-1-(4-pyridinyl)-2-propen-1-one;
trans-3-(5-Methoxy-1-methyl-Indol-3-yl)-1-(4-pyridinyl)-2-propen-1-one;
trans-3-(5-Hydroxy-1H-Indol-3-yl)-1-(4-pyridinyl)-2-propen-1-one;
trans-3-[5-((4-Methylbenzoate)methoxy)-1H-Indol-3-yl)]-1-(4-pyridinyl)-2-propen-1-one;
trans-3-[5-((4-Carboxyphenyl)-methoxy)-1H-Indol-3-yl)]-1-(4-pyridinyl)-2-propen-1-one;
and pharmaceutically acceptable salts, hydrates, and optical isomers thereof.

22. A compound of claim 21, wherein the compound consists essentially of trans-3-(5-Methoxy-2-methyl-1H-indol-3-yl)-1-(4-pyridinyl)-2-propen-1-one.

23. The method of claim 14, wherein Ar is 4-pyridyl and the cancer is resistant to therapeutic agents that cause cells to die by apoptosis or other methods.

* * * * *